(12) United States Patent
Flanagan et al.

(10) Patent No.: US 6,777,536 B1
(45) Date of Patent: Aug. 17, 2004

(54) EPH RECEPTOR LIGANDS, AND USES RELATED THERETO

(75) Inventors: John G. Flanagan, Newton, MA (US); Hwai-Jong Cheng, Boston, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 08/393,462

(22) Filed: Feb. 27, 1995

Related U.S. Application Data

(63) Continuation-in-part of application No. 08/308,814, filed on Sep. 19, 1994, now abandoned.

(51) Int. Cl.[7] .................. C07K 14/00; C12N 15/12; C12N 15/63; C12N 5/00; G01N 33/53
(52) U.S. Cl. .............. 530/350; 536/23.1; 536/23.5; 435/7.1; 435/69.1; 435/252.3; 435/320.1
(58) Field of Search .................. 530/350; 536/23.1, 536/23.5; 435/7.1, 69.1, 252.3, 320.1

(56) References Cited

U.S. PATENT DOCUMENTS 6,268,482 B1 * 7/2001 Cerretti ................ 530/351

OTHER PUBLICATIONS

Voet et al. Biochemistry. 1990. John Wiley and Sons, Inc. pp. 126–128 and 228–334.*

Mikayama T. Molecular cloning and funtional expression of a cDNA encoding glycosylation–inhibiting factor. Proc. Natl. Acad. Sci. USA vol. 90, pp. 10056–10060, 1993.*

Voet et al. Biochemistry. 1990. John Wiley & Sons, Inc., pp. 126–128 and 228–234.*

Flanagan et al (1994) cell 79: 157–168.*

Flanagan et al, (1995) cell) 82:371–381.*

* cited by examiner

*Primary Examiner*—Yvonne Eyler
*Assistant Examiner*—Joseph F. Murphy
(74) *Attorney, Agent, or Firm*—Foley Hoag LLP

(57) ABSTRACT

The present invention relates to the discovery of a novel EPH receptor ligand, referred to hereinafter as "Elf-1", which protein has apparently broad involvement in the formation and maintenance of ordered spatial arrangements of differentiated tissues in vertebrates, and can be used to generate and/or maintain an array of different vertebrate tissue both in vitro and in vivo.

14 Claims, 12 Drawing Sheets

```
     M   A   P   A   Q   R   P   L   L   P   L   L   L   L   L   P              17
     accgggccatggcgccccgcgagcccgctgctgccgctgctgctgctgccg                         60
     L   R   A ▽ R   N   E   D   P   A   R   A   N   A   D   R   Y   A   V   Y   W    37
     ctgcgtgcgcgcaacgaggacccggcccggccaacgctgaccgcagtctactgg                      120
     N   R   S   N   P   R   F   Q   V   S   A   V   G   D   G   G   G   Y   T   V    57
     aaccgtagcaacccagtttcaggtgagcgtgtgggtgatggcggctataccgtg                      180
                                   *
     E   V   S   I   N   D   Y   L   D   I   Y   C   P   H   Y   G   A   P   L   P    77
     gaggtgagcatcaacgactacctggatatctactgcccacactacggggcccctgccc                  240
     P   A   E   R   M   E   R   Y   I   L   Y   M   V   N   G   E   G   H   A   S    97
     ccggctgagcgcatgagcggtacatcctgtacatgtgaatgtgaggccacgcctcc                    300
     *
     C   D   H   R   Q   R   G   F   K   R   W   E   C   N   R   P   A   A   P   G   117
     tgtgaccaccggcagcgaggcttcaagcgctggaatgcaaccggcccgcagcgccccggg                360
     G   P   L   K   F   S   E   K   F   Q   L   F   T   P   F   S   L   G   F   E   137
     ggacccctcaagttctcagagaagttccaactcttcacccctttccctggctttgag                   420
     F   R   P   G   H   E   Y   Y   Y   I   S   A   T   P   P   N   L   V   D   R   157
     ttccggcctggccacgaatactactacatctctgccacacctccaacctcgtggacga                  480
                                                         ○
     P   C   L   R   L   K   V   Y   V   R   P   T   N   E   T   L   Y   E   A   P   177
     ccctgcctgcgactcaaagtttatgtgcgtccaaccaatgagaccctgtatgaggctcca                540
                                     *
     E   P   I   F   T   S   N   S   S   C   S   G   L   G   G   C   H   L   F   L   197
     gagcccatcttcaccagtaacagctcctgcagcggcctgggtggctgccacctcttcctc                600
                     ○                                 *
```

FIG. 2A (1)

```
T  T  P  V  L  W  S  L  L  G  S                                                  209
accaccgtccctgtgctgtggtccttctggctcctagtgtcaggccggagaacaccag                        660
cccacctggagaccccgtgacctttgccctctgacctgccacgcgccacctccgagacaaaa                   720
tccttgctgctctcttcatggtgctgtcccgcgtcccgtccatccgtccctg                             780
ggatgcaacatggggtcccaatgcctgaggagaagaccccccaaggctgactcgctt                        840
tcaccaggccaccaggccatccatccagtgttgttaattacagtcgaaagacttaaggttt                    900
ttcttttaattttattccctgacattgctgtgactgggaagacactgggaagaacaagccac                   960
agggatgaggtgaagccatctctgtccttcctggaataccggagatccaggggcctccag                    1020
ctgctcctctcttcctgtcctgttatttggtcccagatggagcccgcgcaggcctgc                       1080
cttgcattcctcaggccaagccaagcctgagcgcagaaagggcacgtgccagccccctct                    1140
cggggactctggggtgccatccccccagcctcttcctccagccaactcgggccccactccc                   1200
acatcatctcagaaaacctcagcccgggccagccggacgttgtcggttatttctgtaaatagaaaccagc          1260
acaaccatcccggggccagccggacgttgtcggttatttctgtaaatagaaaccagc                        1320
aagtgtatactgtgatttttccgaccttcaattcttaaggacagaatgaaattcttaaaa                    1380
aaaatttttttttccgacctcaagggtcatttatttggtgggggagtggggt                            1440
ggacttttaggatagaagcaacactttgcaatacttttttttgttccgttga                            1500
gccctcccccttgatcatgtgacctagtaatgtttataacaaaaaaaaaa                              1555
```

FIG. 2A (2)

```
ChElf-1: MPRWEARALLAAIVGXCVWSDDPGKVIS**DRYXVYWNRSNPRFHR
MuElf-1: MAPAQRPLLPLLLLLLPLRARNEDPARANADRYAVYWNRSNPRFQV
Degen:                                 DRYXVYWNRSNPRFXX

*GD*YTVEVSINDYLDIYCPHYEEPLP*AERMERYVLYMVNYEGHAS
SAVGDGGGYTVEVSINDYLDIYCPHYGAPLPPAERMERYILYMVNGEGHAS
XXXGDXXXYTVEVSINDYLDIYCPHYXXPLPXAERMERYXLYMVNXEGHAS

CDHRQKGFKRWECNRPDSPSGPLKFSEKFQLFTPFSLGFEFRPGHEYYYIS
CDHRQRGFKRWECNRPAAPGGPLKFSEKFQLFTPFSLGFEFRPGHEYYYIS
CDHRQXGFKRWECNRPXXPXGPLKFSEKFQLFTPFSLGFEFRPGHEYYYIS

ASPPNVVDRPCLKLKVYVRPTNDSLYESPEPIFTSNNSCCSLAVPRAVLVA
ATPPNLVDRPCLRLKVYVRPTNETLYEAPEPIFTSNSSCSGLGGCHLFLTT
AXPPNXVDRPCLXLKVYVRPTNXXLYEXPEPIFTSNXSCXXLXXXXXXLXX

APVFWTLLGS   (SEQ ID No: 4)
VPVLWSLLGS   (SEQ ID No: 2)
XPVXWXLLGS   (SEQ ID No: 5)
```

EPH RECEPTOR LIGANDS, AND USES RELATED THERETO

REFERENCE TO RELATED APPLICATIONS

This application in a continuation-in-part of U.S. Ser. No. 08/308,814, filed Sep. 19, 1994, now abandoned, and entitled "EPH Receptor Ligands, and Uses Related Thereto". The disclosure of U.S. Ser. No. 08/308,814 is incorporated by reference.

GOVERNMENT FUNDING

Work described herein was supported by National Institutes of Health Grants DK45580 and HD29417. The United States Government has certain rights in the invention.

BACKGROUND OF THE INVENTION

Pattern formation is the activity by which embryonic cells form ordered spatial arrangements of differentiated tissues. The physical complexity of higher organisms arises during embryogenesis through the interplay of cell-intrinsic lineage and cell-extrinsic signaling. Inductive interactions are essential to embryonic patterning in vertebrate development from the earliest establishment of the body plan, to the patterning of the organ systems, to the generation of diversive cell types during tissue differentiation (Davidson, E., (1990) *Development* 108: 365–389; Gurdon, J. B., (1992) *Cell* 68: 185–199; Jessell, T. M. et al., (1992) *Cell* 68: 257–270). The effects of developmental cell interactions are varied. Typically, responding cells are diverted from one route of cell differentiation to another by inducing cells that differ from both the uninduced and induced states of the responding cells (inductions). Sometimes cells induce their neighbors to differentiate like themselves (homoiogenetic induction); in other cases a cell inhibits its neighbors from differentiating like itself. Cell interactions in early development may be sequential, such that an initial induction between two cell types leads to a progressive amplification of diversity. Moreover, inductive interactions occur not only in embryos, but in adult cells as well, and can act to establish and maintain morphogenetic patterns as well as induce differentiation (J.B. Gurdon (1992) *Cell* 68:185–199).

Many types of communication take place among animal cells during embryogenesis, as well as in the maintenance of tissue in adult animals. These vary from long-range effects, such as those of rather stable hormones circulating in the blood and acting on any cells in the body that possess the appropriate receptors, however distant they are, to the fleeting effects of very unstable neurotransmitters operating over distances of only a few microns. Of particular importance in development is the class of cell interactions referred to above as embryonic induction; this includes influences operating between adjacent cells or in some cases over greater than 10 cell diameters (Saxen et al. (1989) *Int J Dev Biol* 33:21–48; and Gurdon et al. (1987) *Development* 99:285–306). Embryonic induction is defined as in interaction between one (inducing) and another (responding) tissue or cell, as a result of which the responding cells undergo a change in the direction of differentiation. This interaction is often considered one of the most important mechanism in vertebrate development leading to differences between cells and to the organization of cells into tissues and organs.

Receptor tyrosine kinases are apparently involved in many different process including cellular differentiation, proliferation, embryonic development and, in some cases, neoplastic growth. High affinity binding of specfic soluble or matrix-associated growth factor ligands can cause the activated receptor to associate with a specific repertoire of cytoplasmic singnalling molecules that can lead to a cascade of intracellular signalling resulting in, for example, activation or inactivation of cellular gene programs involved in differentiation and/or growth. Accordingly, peptide growth factors that are ligands for such receptor tyrosine kinases are excellent candidates for intercellular signaling molecules with important developmental roles. Indeed, these ligands are known to have potent effects on a wide variety of cell activities in vitro, including survival, proliferation, differentiation, adhesion, migration and axon guidance. The powerful signaling effects of these molecules are further emphasized by the ability of both the ligands and the receptors, when activated by mutation or overexpression, to become potent oncogenes and cause drastic cellular transformation (reviewed by Cantley et al. (1991) *Cell* 64:281–302; Schlessinger and Ullrich (1992) *Neuron* 9:383–391; and Fantl et al. (1993)*Annu Rev Biochem* 62:453–481).

To illustrate, specific developmental roles have been demonstrated for some growth factors or their tyrosine kinase receptors. For example, the c-kit receptor tyrosine kinase, encoded at the mouse W locus (Chabot et al. (1988) *Nature* 335:88–89; and Geissler et al. (1988) *Cell* 55:185–192) and its ligand KL, encoded at the mouse SI locus (Flanagan and Leder (1990) *Cell* 63:185–194; Copeland et al. (1990) *Cell* 63:175–183; Huang et al. (1990) *Cell* 63:225–233; and Zsebo et al. (1990) *Cell* 63:213–224), determine the proliferation, survival, and/or migration of primordial germ cells, hematopoietic stem cells, and neural crest progenitor cells. Other examples are the trk family ligands and receptors, with highly specific functions in the developing mammalian nervous system (Klein et al. (1993) *Cell* 75:113–122; and Jones et al. (1994) *Cell* 76:989–999) and the FGF receptor, implicated in Xenopus mesoderm induction (Amaya et al. (1991) *Cell* 66:257–270). In invertebrates, too, receptor tyrosine kinases and ligands such as sevenless, boss, torso, breathless and let-23 are known to play key roles in processes that range from setting up the primary embryonic axes to specifying the fate of a single cell in the ommatidium (Greenwald and Rubin (1992) *Cell* 68:271–281; Shilo (1992) *Faseb J* 6:2915–2922; and Zipursky et al. (1992) *Cold Spring Harbor Symp Quant Biol* 57:381–389). Taken together, the emerging picture of the developmental functions of receptor tyrosine kinases and their ligands is striking in that these molecules play key roles at all stages of embryonic development, and in a remarkable range of different types of patterning process.

The receptor tyrosine kinases can be divided into families based on structural homology and, in at least some cases, obvious shared functional characteristics (Fantl et al. (1993) *Annu Rev Biochem* 62:453481). The family with by far the largest number of known members is the EPH family. Since the description of the prototype, the EPH receptor (Hirai et al. (1987) *Science* 238:1717–1720), sequences have been reported for at least ten members of this family, not counting apparently orthologous receptors found in more than one species. Additional partial sequences, and the rate at which new members are still being reported, suggest the family is even larger (Maisonpierre et al. (1993) *Oncogene* 8:3277–3288; Andres et al. (1994) *Oncogene* 9:1461–1467; Henkemeyer et al. (1994) *Oncogene* 9:1001–1014; Ruiz et al. (1994) *Mech Dev* 46:87–100; Xu et al. (1994) *Development* 120:287–299; Zhou et al. (1994) *J Neurosci Res* 37:129–143; and references in Tuzi and Gullick (1994) *Br J Cancer* 69:417–421). Remarkably, despite the large number of members in the EPH family, all of these molecules were identified as orphan receptors without known ligands.

SUMMARY OF THE INVENTION

The present invention relates to the discovery of a novel EPH receptor ligand, referred to hereinafter as "Elf-1", which protein has apparently broad involvement in the formation and maintenance of ordered spatial arrangements of differentiated tissues in vertebrates, and can be used to generate and/or maintain an array of different vertebrate tissue both in vitro and in vivo.

In general, the invention features an Elf-1 polypeptide, preferably a substantially pure preparation of an Elf-1 polypeptide, or a recombinant Elf-1 polypeptide. In preferred embodiments the polypeptide has a biological activity associated with its binding to an EPH receptor, e.g., it retains the ability to bind to a hek-related or sek-related receptor, though it may be able to either agnoize or antagonize signal transduction by the EPH receptor. The polypeptide can be identical to the mammalian Elf-1 polypeptide (muElf-1) shown in SEQ ID No: 2, or it can merely be homologous to that sequence. Likewise, the polypeptide can be identical to the avian Elf-1 polypeptide (chElf-1) shown in SEQ ID No: 4, or it can merely be homologous to that sequence. For instance, the polypeptide preferably has an amino acid sequence at least 70% homologous to the amino acid sequence in either or both of SEQ ID Nos: 2 and 4, though higher sequence homologies of, for example, 80%, 85%, 90% or 95% are also contemplated. The polypeptide can comprise the full length protein represented in SEQ ID No: 2 or 4, or it can comprise a fragment of that protein, which fragment may be, for instance, at least 5, 10, 20, 50 or 100 amino acids in length. A preferred Elf-1 polypeptide includes a $Cys_4$ motif, such as the polypeptide between and including Cys-69 through Cys-159 of SEQ ID No: 2, or a sequence homologous thereto, such as residues 61–150 of SEQ ID No: 4 or residues 39–129 of SEQ ID No: 5. Yet another preferred Elf-1 polypeptide includes a core sequence motif, such as a polypeptide including residues 35–166 of SEQ ID No. 2, residues 33–157 of SEQ ID No. 4, or residues 5–136 of SEQ ID No. 5.

The polypeptide can be glycosylated, or, by virtue of the expression system in which it is produced, or by modification of the protein sequence to preclude glycosylation, reduced carbohydrate analogs can be provided. Likewise, Elf-1 polypeptides can be generated which lack an endogenous signal sequence (though this is typically cleaved off even if present in the pro-form of the protein), or which lack a phosphatidylinositol linkage site to preclude addition of phosphatidylinositol. In the instance of the latter, the removal of the C-terminus may result in a soluble form of the protein. In particular, polypeptides which lack at least the last 15 amino acid residues (the equivalent of muElf-1 truncated at Leu-195) are preferred, though polypeptides which are truncated anywhere between the equivalent of Thr-182 to Leu-195 of SEQ ID No: 2 are also contemplated.

Furthermore, the Elf-1 polypeptide can include a secretion signal sequence, such as residues Met-1 to Ala-20 of SEQ ID No. 2, though mature Elf-1 polypeptides are also provided, such as the exemplary full length mature polypeptide represented by residues Arg-21 to Ser-209.

Moreover, as described below, the polypeptide can be either an agonist (e.g. mimics), or alternatively, an antagonist of a biological activity of a naturally occuring form of the protein, e.g., the polypeptide is able to modulate growth and/or differentiation of a cell which expresses an EPH receptor.

In a preferred embodiment, a peptide having at least one biological activity of the subject polypepide may differ in amino acid sequence from the sequence in SEQ ID No: 2 or 4, but such differences result in a modified protein which functions in the same or similar manner as a native Elf-1 protein or which has the same or similar characteristics of a native Elf-1 protein. However, homologs of the naturally occuring protein are contemplated which are antagonistic of the normal physiological role of the naturally occurring protein. For example, the homolog may be capable of interfering with the ability of naturally-occurring forms of Elf-1 to modulate gene expression, e.g. of developmentally or growth regulated genes. Exemplary Elf-1 homologs are represented in the general formula:

---

D-R-Y-X (1) -V-Y-W-N-R-S-N-P-R-F-X (2) -X (3) -X (4) -X (5) - X (6) -G-D-X (7) -X (8) -X (9) -Y-T-V-E-V-S-I-N-D-Y-L-D-I-Y-C- P-H-Y-X (10) -X (11) -P-L-P-X (12) -A-E-R-M-E-R-Y-X (13) -L-Y- M-V-N-X (14) -E-G-H-A-S-C-D-H-R-Q-X (15) -G-F-K-R-W-E-C-N- R-P-X (16) -X (17) -P-X (18) -G-P-L-K-F-S-E-K-F-Q-L-F-T-P-F- S-L-G-F-E-F-R-P-G-H-E-Y-Y-Y-I-S-A-X (19) -P-P-N-X (20) -V- D-R-P-C-L-X (21) -L-K-V-Y-V-R-P-T-N-X (22) -X (23) -L-Y-E- X (24) -P-E-P-I-F-T-S-N-X (25) -S-C-X (26) -X (27) -L-X (28) - X (29) -X (30) -X (31) -X (32) -X (33) -L-X (34) -X (35) -X (36)-P-V- X (37) -W-X (38) -L-L-G-S    (SEQ ID No: 5)

---

In yet other preferred embodiments, the Elf-1 protein is a recombinant fusion protein which includes a second polypeptide portion, e.g., a second polypeptide having an amino acid sequence unrelated to Elf-1, e.g. the second polypeptide portion is glutathione-S-transferase, e.g. the second polypeptide portion is an enzymatic activity such as alkaline phosphatase, and is a reagent for detecting Elf-1 receptors.

Yet another aspect of the present invention concerns an immunogen comprising a Elf-1 polypeptide in an immunogenic preparation, the immunogen being capable of eliciting an immune response specific for an Elf-1 polypeptide; e.g. a humoral response, e.g. an antibody response; e.g. a cellular response. In preferred embodiments, the immunogen comprising an antigenic determinant, e.g. a unique determinant, from a protein represented by SEQ ID No. 2 or SEQ ID No. 4.

A still further aspect of the present invention features an antibody preparation specifically reactive with an epitope of the Elf-1 immunogen.

Another aspect of the present invention provides a substantially isolated nucleic acid having a nucleotide sequence which encodes an Elf-1 polypeptide. In preferred embodiments: the encoded polypeptide specifically binds an EPH receptor protein and/or is able to either agnoize or antagonize signal transduction events mediated by the EPH receptor. The coding sequence of the nucleic acid can comprise a sequence which can be identical to the cDNA shown in SEQ ID No: 1 or SEQ ID No: 3, or it can merely be homologous to that sequence. For instance, the Elf-1 encoding sequence preferably has a sequence at least 70% homologous to a nucleotide sequence of one or both of SEQ ID Nos: 1 and 3, though higher sequence homologies of, for example, 80%, 90% or 95% are also contemplated. The polypeptide encoded by the nucleic acid can comprise the amino acid sequence represented in SEQ ID No: 2 or 4, which is the full length protein, or it can comprise a fragment of that nucleic acid, which fragment may be, for instance, at least 5, 10, 20, 50 or 100 amino acids in length. The polypeptide encoded by the nucleic acid can be either an agonist (e.g. mimics), or alternatively, an antagonist of a biological activity of a naturally occuring form of the protein.

Furthermore, in certain preferred embodiments, the subject Elf-1 nucleic acid will include a transcriptional regulatory sequence, e.g. at least one of a transcriptional promoter or transcriptional enhancer sequence, which regulatory sequence is operably linked to the Elf-1 gene sequence. Such regulatory sequences can be used in to render the Elf-1 gene sequence suitable for use as an expression vector.

In a further preferred embodiment, the nucleic acid hybridizes under stringent conditions to a nucleic acid probe corresponding to at least 12 consecutive nucleotides of SEQ ID No: 1; preferably to at least 20 consecutive nucleotides of SEQ ID No: 1; more preferably to at least 40 consecutive nucleotides of SEQ ID No: 1.

In yet a further preferred embodiment, the nucleic acid hybridizes under stringent conditions to a nucleic acid probe corresponding to at least 12 consecutive nucleotides of SEQ ID No: 3; preferably to at least 20 consecutive nucleotides of SEQ ID No: 3; more preferably to at least 40 consecutive nucleotides of SEQ ID No: 3.

The invention also features transgenic non-human animals, e.g. mice, rats, rabbits, chickens, frogs or pigs, having a transgene, e.g., animals which include (and preferably express) a heterologous form of an Elf-1 gene described herein, or which misexpress an endogenous Elf-1 gene, e.g., an animal in which expression of the subject Elf-1 protein is disrupted. Such a transgenic animal can serve as an animal model for studying cellular and tissue disorders comprising mutated or mis-expressed Elf-1 alleles or for use in drug screening.

The invention also provides a probe/primer comprising a substantially purified oligonucleotide, wherein the oligonucleotide comprises a region of nucleotide sequence which hybridizes under stringent conditions to at least 10 consecutive nucleotides of sense or antisense sequence of SEQ ID No: 1 and/or 3, or naturally occurring mutants thereof. In preferred embodiments, the probe/primer further includes a label group attached thereto and able to be detected. The label group can be selected, e.g., from a group consisting of radioisotopes, fluorescent compounds, enzymes, and enzyme co-factors. Probes of the invention can be used as a part of a diagnostic test kit for identifying transformed cells, such as for detecting in a sample of cells isolated from a patient, a level of a nucleic acid encoding the subject Elf-1 proteins; e.g. measuring the Elf-1 mRNA level in a cell, or determining whether the genomic Elf-1 gene has been mutated or deleted. Preferably, the oligonucleotide is at least 10 nucleotides in length, though primers of, for example, 20, 30, 50, 100, or 150 nucleotides in length are also contemplated.

In yet another aspect, the invention provides an assay for screening test compounds for inhibitors, or alternatively, potentiators, of an interaction between Elf-1 and an EPH receptor. An exemplary method includes the steps of (i) combining an EPH receptor, an Elf-1 polypeptide, and a test compound, e.g., under conditions wherein, but for the test compound, the Elf-1 protein and the EPH receptor are able to interact; and (ii) detecting the formation of a complex which includes the Elf-1 protein and the receptor. A statistically significant change, such as a decrease, in the formation of the complex in the presence of a test compound (relative to what is seen in the absence of the test compound) is indicative of a modulation, e.g., inhibition, of the interaction between Elf-1 and the receptor. For example, primary screens are provided in which the Elf-1 protein and the receptor protein are combined in a cell-free system and contacted with the test compound; i.e. the cell-free system is selected from a group consisting of a cell lysate and a reconstituted protein mixture.

Another aspect of the present invention relates to a method of inducing and/or maintaining a differentiated state, causing proliferation, and/or enhancing survival of a cell responsive to a Elf-1 protein, by contacting the cells with an Elf-1 agonist or an Elf-1 antagonist. For example, the present method is applicable to cell culture technique, such as in the culturing of neuronal and other cells whose survival or differentiative state is dependent on Elf-1 function. Moreover, Elf-1 agonists and antagonists can be used for therapeutic intervention, such as to enhance survival and maintenance of neurons and other neural cells in both the central nervous system and the peripheral nervous system, as well as to influence other vertebrate organogenic pathways, such as other ectodermal patterning, as well as certain mesodermal and endodermal differentiation processes.

Another aspect of the present invention provides a method of determining if a subject, e.g. a human patient, is at risk for a disorder characterized by unwanted cell proliferation or abherent control of differentiation. The method includes detecting, in a tissue of the subject, the presence or absence of a genetic lesion characterized by at least one of (i) a mutation of a gene encoding an Elf-1 protein, e.g. represented in SEQ ID No: 2 or 4, or a homolog thereof; or (ii) the mis-expression of an Elf-1 gene. In preferred embodiments, detecting the genetic lesion includes ascertaining the existence of at least one of: a deletion of one or more nucleotides from an Elf-1 gene; an addition of one or more nucleotides to the gene, a substitution of one or more nuclcotides of the gene, a gross chromosomal rearrangement of the gene; an alteration in the level of a messenger RNA transcript of the gene; the presence of a non-wild type splicing pattern of a messenger RNA transcript of the gene; or a non-wild type level of the protein.

For example, detecting the genetic lesion can include (i) providing a probe/primer including an oligonucleotide containing a region of nucleotide sequence which hybridizes to a sense or antisense sequence of an Elf-1 gene, e.g. the nucleic acid represented in SEQ ID No: 1 or 3, or naturally occurring mutants thereof or 5' or 3' flanking sequences naturally associated with the Elf-1 gene; (ii) exposing the probe/primer to nucleic acid of the tissue; and (iii) detecting, by hybridization of the probe/primer to the nucleic acid, the presence or absence of the genetic lesion; e.g. wherein detecting the lesion comprises utilizing the probe/primer to determine the nucleotide sequence of the Elf-1 gene and, optionally, of the flanking nucleic acid sequences. For instance, the probe/primer can be employed in a polymerase chain reaction (PCR) or in a ligation chain reaction (LCR). In alternate embodiments, the level of Elf-1 protein is detected in an immunoassay using an antibody which is specifically immunoreactive with an Elf-1 protein.

Yet another aspect of the invention relates to a novel in situ assay for detecting receptors or their ligands in tissue samples and while organisms. In general, the "RAP-in situ" assay (for Receptor Affinity Probe) of the present invention comprises (i) providing a hybrid molecule (the affinity probe) including a receptor, or a receptor ligand, covalently bonded to an enzymatically active tag, preferably for which chromogenic substrates exist, (ii) contacting the tissue or organism with the affinity probe to form complexes between the probe and a cognate receptor or ligand in the sample, removing unbound probe, and (iii) detecting the affinity complex using a chromogenic substrate for the enzymatic acitivity associated with the affinity probe. In preferred embodiments, an alkaline phosphatase provides an enzymatic tag, though such enzymes horseradish peroxidase, β-galactosidase, malate dehydrogenase, yeast alcohol dehydrogenase, α-glycerophosphate dehydrogenase, triose phosphate isomerase, asparaginase, glucose oxidase, and urease are also useful. The method can be used, for example, to detect patterns of expression for particular receptors and their ligands, for measuring the affinity of receptor/ligand interactions in tissue samples, as well as for generating drug screening assays in tissue samples. Moreover, the affinity probe can also be used in diagnostic screening to determine whether a receptor, e.g. an EPH receptor, or its ligand, e.g. Elf-1 or B61 or LERK proteins, are misexpressed.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual,* 2nd Ed., ed. by Sambrook, Fritsch and Maniatis (Cold Spring Harbor Laboratory Press: 1989); *DNA Cloning,* Volumes I and II (D. N. Glover ed., 1985); *Oligonucleotide Synthesis* (M. J. Gait ed., 1984); Mullis et al. U.S. Pat. No: 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology,* Vols. 154 and 155 (Wu et al. eds.), *Immunochemical Methods In Cell And Molecular Biology* (Mayer and Walker, eds., Academic Press, London, 1987); *Handbook Of Experimental Immunology,* Volumes I–IV (D. M. Weir and C. C. Blackwell, eds., 1986); *Manipulating the Mouse Embryo,* (Cold Spring Harbor Laboratory Press, Cold Spring Harbor, N.Y., 1986).

Other features and advantages of the invention will be apparent from the following detailed description, and from the claims.

DESCRIPTION OF THE DRAWINGS

FIG. 2A is the nucleic acid sequence of an Elf-1 cDNA clone (SEQ ID No. 1), and the virtual amino acid sequence (SEQ ID No. 2). The deduced amino acid sequence is shown in single-letter code above the nucleotide sequence. Cysteine residues are marked with asterisks, potential N-linked glycosylation sites are indicated by small filled circles, and a probable endpoint for the secretion signal sequence is indicated by an open triangle. A polyadenylation signal in the 3' untranslated sequence is underlined.

(FIGS. 3A and 3D) Cells were treated with saturating amounts of mek4-AP or sek-AP, or with AP, each at 500 OD/hr/ml. Columns show the average of two binding determinations, and error bars indicate the difference between the two. (FIGS. 3B–C and 3E–F) show the Scatchard analyses of binding. (FIGS. 3A–3C illsutrate binding to COS cells transfected with Elf-1, and FIGS. 3D–F show endogenous ligand expression by the BRL-3A cell line). Binding characteristics calculated for the experiments shown are as follows: for mek4-AP with Elf-1 in COS cells, $1.7 \times 10^5$ sites average per cell with $KD=1.8 \times 10^{-9}M$; with BRL-3A cells $5 \times 10^4$ sites per cell with $KD=1.3 \times 10^{-9}$ M. For sek-AP with Elf-1 in COS cells, $1.0 \times 10^5$ sites average per cell with $KD=1.8 \times 10^{-8}$ M; with BRL-3A cells, $3 \times 10^4$ sites per cell with $KD=0.67 \times 10^{-8}M$.

FIG. 4 is a sequence alignment of the mouse and chicken Elf-1 polypeptides ("muElf-1" and "chElf-1", respectively). A degenerate consensus sequence ("degen") is provided from the sequence comparision.

DETAILED DESCRIPTION OF THE INVENTION

Figure 1A:
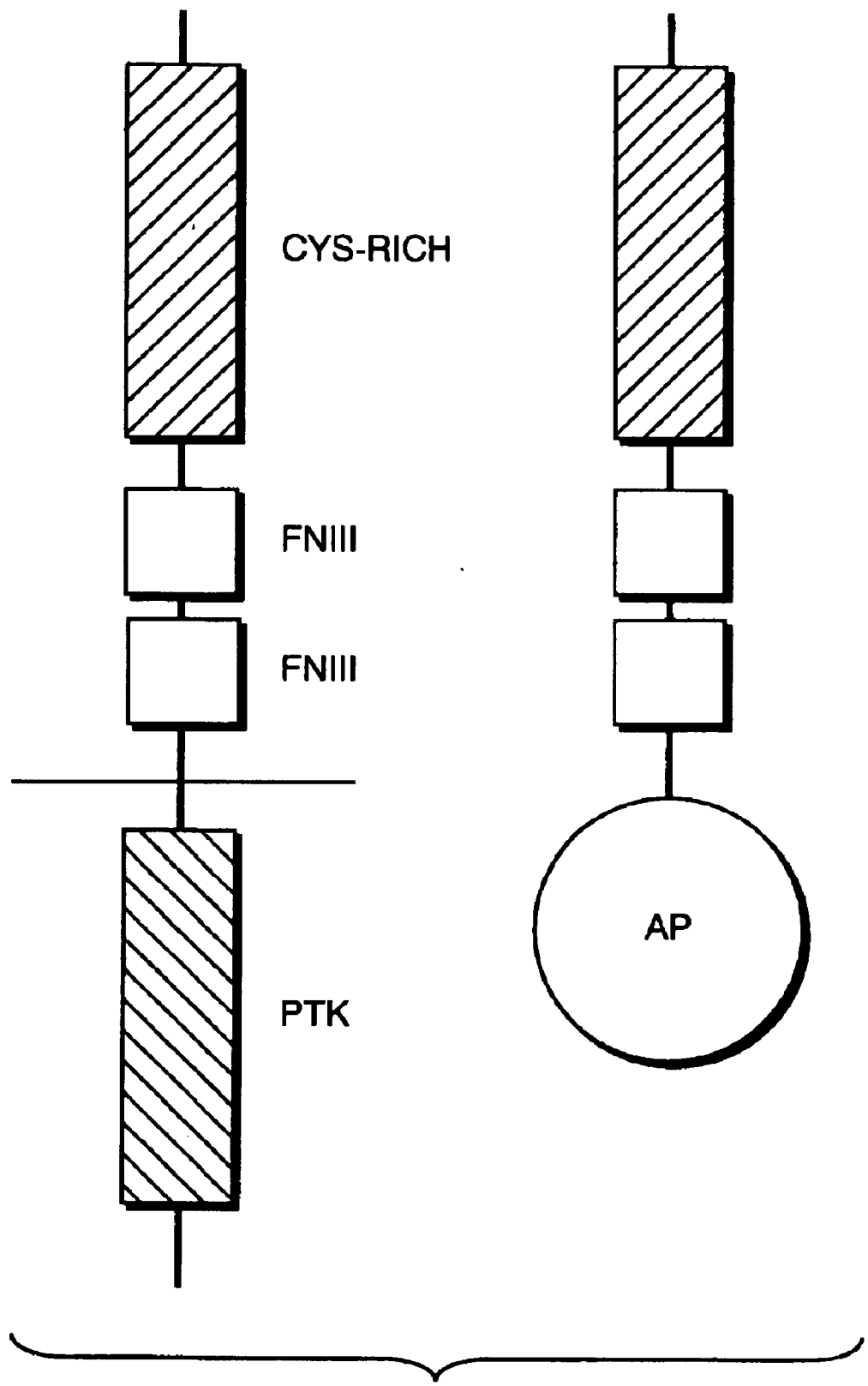
FIG. 1A graphically illustrates the Mek4-AP and Sek-AP soluble receptor affinity reagents. The Mek4 and Sek receptor tyrosine kinases are illustrated on the left. Like other members of the Eph family, each has a cysteine-rich domain with a characteristic spacing of cysteine residues (hatched box) followed by two fibronectin III motifs (open boxes) a single transmembrane domain and an intracellular tyrosine kinase domain (filled box). The diagram to the right illustrates the structure of the Mek4-AP and Sek-AP soluble receptor affinity reagents, each of which consists of the receptor extracellular domain fused to a placental alkaline phosphatase tag.

Growth factors that are ligands for receptor tyrosine kinases control a wide variety of cellular activities. Virtually all of these ligands that have been characterized are known to have important functions in development and/or physiology and, in at least some cases, to be useful clinically. The existence of many additional, hitherto unidentified ligands is implied by the discovery over the last few years of a large number of tyrosine kinases that appear by their structure to be cell surface receptors, yet have no known ligand. The rapid discovery of these orphan receptors has been possible mostly through the application of techniques such as polymerase chain reaction that take advantage of the strong sequence conservation of the kinase catalytic domain. However, in contrast, identification of the ligands for the orphan receptor tyrosine kinases has been more problematic.

It is also generally accepted that intercellular signaling plays a key role throughout vertebrate development. A great deal of progress has been made in understanding signals that mediate some of the earliest patterning events. However, little is known about the signals that regulate many of the important events that unfold as gastrulation and early orgaonogenesis proceed, particularly the cell-cell signaling molecules that control the expression of gene programs. Protein tyrosine kinases, such as members of the EPH family, have been especially intriguing in this regard, particularly because the expression domains for several of these receptors include these stages of development.

The expression patterns determined for some of the EPH family receptors have implied important roles for these molecules in early vertebrate development. In particular, the timing and pattern of expression of sek, mek4 and some of the other receptors during the phase of gastrulation and early organogenesis has suggested functions for these receptors in the important cellular interactions involved in patterning the embryo at this stage (Gilardi-Hebenstreit et al. (1992) *Oncogene* 7:2499–2506; Nieto et al. (1992) *Development* 116:1137–1150; Henkemeyer et al., supra; Ruiz et al., supra; and Xu et al., supra). Sek, for example, shows a notable early expression in the two areas of the mouse embryo that show obvious segmentation, namely the somites in the mesoderm and the rhombomeres of the hindbrain; hence the name sek, for segmentally expressed kinase (Gilardi-Hebenstreit et al., supra; Nieto et al., supra). As in Drosophila, these segmental structures of the mammalian embryo are implicated as important elements in establishing the body plan. The observation that Sek expression precedes the appearance of morphological segmentation suggests a role for sek in forming these segmental structures, or in determining segment-specific cell properties such as lineage compartmentation (Nieto et al., supra). Moreover, EPH receptors have been implicated, by their pattern of expression, in the development and maintenance of nearly every tissue in the embryonic and adult body. For instance, EPH receptors have been detected throughout the nervous system, the testes, the cartilaginous model of the skeleton, tooth primordia, the infundibular component of the pituitary, various epithelia tissues, lung, pancreas, liver and kidney tissues. Observations such as this have been indicative of important and unique roles for EPH family kinases in development and physiology, but further progress in understanding their action has been severely limited by the lack of information on their ligands.

However, as described in the appended examples, we have utilized soluble Mek4-AP (AP=alkaline phosphatase) and Sek-AP fusion proteins in a unique screening assay to clone a novel EPH receptor ligand termed herein "Elf-1". In addition to identifying this novel ligand and homologs thereof, we have characterized the spatial distribution of expression of the protein in a number of different species (mammalian a dn non-mammalian), and find that it is likely to be of central importance in development. Given the apparent role of the Elf-1 protein in mediating inductive signals between tissues, the present data suggests that this protein is an important therapeutic target for modulating growth and developmental gene programs. For example, binding of an Elf-1 polypeptide of the present invention with an EPH receptor can be important for initiating and establishing diverse programs of differentiation; as well as for providing a mechanism to ensure developmentally coordinated tissue patterning. Moreover, it is suggested that certain EPH receptors, e.g. the hek receptor, may also play a role in tumorogenesis. Consequently, the interaction of an EPH receptor with the subject Elf-1 polypeptides may be significant in the modulation of cellular homeostasis, in the control of organogenesis, or in the maintenance of differentiated tissues, as well as in the development of lymphocytic leukemias and other neoplastic disorders.

Accordingly, certain aspects of the present invention relate to diagnostic and therapeutic assays and reagents for detecting and treating disorders involving abherent expression of Elf-1. Moreover, drug discovery assays are provided for identifying agents which can modulate the binding of Elf-1 with EPH receptors. Such agents can be useful therapeutically to alter the growth and/or differentiation of a cell.

Other aspects of the invention are described below or will be apparent to those skilled in the art in light of the present disclosure.

For convience, certain terms employed in the specfication, examples, and appended claims are collected here.

The term "Elf-1 polypeptide" refers to a family of polypeptides characterized at least in part by being identical or sharing a degree of sequence homology with all or a portion of the polypeptides represented in SEQ ID No. 2 and SEQ ID No. 4. The Elf-1 polypeptides can be cloned or purified from any of a number of eukaryotic organisms, especially vertebrates, and particularly mammals. Moreover, other Elf-1 polypeptides can be generated according to the present invention, which polypeptides do not ordinarily exist in nature, but rather are generated by non-natural mutagenic techniques. For example, the polypeptides represented by the general formula of SEQ ID No. 5 include non-naturally occurring Elf-1 polypeptides.

As described in the appended examples, a number of features of this family of proteins can be observed from comparison of various Elf-1 polypeptides with each other and with other EPH receptor ligands. In particular, we have noted that four cysteine residues are apparently conserved with approximately the same characteristic spacing within the primary sequence of each of the known EPH receptor ligands. This conserved "motif" containing these four cysteines, referred to herein as a "$Cys_4$ motif", may represent a fragment which retains certain biological activities of the full length (mature) protein, such as, for example, the ability to bind an EPH receptor. In exemplary Elf-1 polypeptides, the $Cys_4$ motif is represented by residues 69–159 of SEQ ID No. 2 (muElf-1), by residues 61–150 of SEQ ID No. 4 (chElf-1), and residues 39–129of SEQ ID No. 5. Those skilled in the art, in light of the present invention, will be able to easily ascertain the equivalent $Cys_4$ motifs in other Elf-1 polypeptides.

Furthermore, we have observed that a "core sequence motif" within the EPH receptor ligands, slightly larger that the $Cys_4$ motif, is suggested by higher sequence homologies over a portion of the protein sequences relative to the full-length, mature protein (see Table 1, Example 10). Similar to the $Cys_4$ motif, the core sequence motif presumably represents a fragment which is likely to be essential for the activity of the mature protein, with the exception of a secretion signal sequence and a glycosyl-phosphatidylinositol attachment sequence. The core sequence motif of Elf-1 is approximately defined by residues 35–166 of SEQ ID No. 2, residues 33–157 of SEQ ID No. 4, and residues 5–136 of SEQ ID No. 5, with analogous core sequence motifs for other Elf-1 polypeptides readily ascertainable by comparison with these sequences.

Finally, co- and post-translational modifications of Elf-1 polypeptides have been observed. A "mature" Elf-1 polypeptide refers to an Elf-1 polypeptide which lacks a signal sequence (e.g., a peptidyl portion which causes extracellular secretion of at least a portion of the protein). An exemplary mature Elf-1 polypeptide is represented by residues Arg-21 to Ser-209.

A "phosphatidylinositol-linked" or "glycosyl phosphatidylinositol-linked" Elf-1 polypeptide is an Elf-1 polypeptide which includes a C-terminal glyocsyl phosphatidylinositol ("GPI") chain. GPI membrane anchor attachment is apparently directed by a carboxy-terminal signal that is proteolytically removed and replaced with a preformed GPI anchor. Accordingly, removal of the last 15 to 20 amino acids at the carboxy-terminal end of the prepro-Elf-1 protein can result in GPI-lacking variants of Elf-1.

A "glycosylated" Elf-1 polypeptide is an Elf-1 polypeptide having a covalent linkage with a glycosyl group (e.g. a derivatized with a carbohydrate). For instance, the exemplary muElf-1 and chELf-1 proteins contain three potential N-linked glycosylation sites. To generate an unglycosylated Elf-1 polypeptide, the polypeptide can be expressed in a system which is defective for glycosylation, such as a bacterial cell. Alternatively, an existing glycosylation site, such as Asn-38, Asn-170 and Asn-184 of muElf-1 or the equivalent, can be mutated to preclude carbohydrate attachment. Likewise, new glycosylation sites, such as for N-linked or O-linked glycosylation, can be added by recombinant techniques.

As used herein, the terms "EPH receptor" or "EPH-type receptor" refer to a class of receptor tyrosine kinases, comprising at least eleven paralogous genes, though many more orthologs exist within this class, e.g. homologs from different species. EPH receptors, in general, are a discrete group of receptors related by homology and easily reconizable, e.g., they are typically characterized by an extracellular domain containing a characteristic spacing of cysteine residues near the N-terminus and two fibronectin type III repeats (Hirai et al. (1987) *Science* 238:1717–1720; Lindberg et al. (1990) *Mol Cell Biol* 10:6316–6324; Chan et al. (1991) *Oncogene* 6:1057–1061; Maisonpierre ct al. (1993) *Oncogene* 8:3277–3288; Andres et al. (1994) *Oncogene* 9:1461–1467; Henkemeyer et al. (1994) *Oncogene* 9:1001–1014; Ruiz et al. (1994) *Mech Dev* 46:87–100; Xu et al. (1994) *Development* 120:287–299; Zhou et al. (1994) *J Neurosci Res* 37:129–143; and references in Tuzi and Gullick (1994) *Br J Cancer* 69:417–421). Exemplary EPH receptors include the eph, elk, eck, sek, mek4, hek, hek2, eek, erk, tyrol, tyro4, tyro5, tyro6, tyroll, cek4, cek5, cek6, cek7, cek8, cek9, cek10, bsk, rtk1, rtk2, rtk3, myk1, myk2, ehk1, ehk2, pagliaccio, htk, erk and nuk receptors. The term "EPH receptor" refers to the membrane form of the receptor protein, as well as soluble extracellular fragments which retain the ability to bind the ligand of the present invention. Furthermore, "mek4/sek type receptors" refers to a closely related subgroup of the EPH receptor family, which subgroup includes: the "mek4-related receptors" such as mek4, cek4, hek and tyro4; the "sek-related receptors" such as sek, cek8, pagliaccio, tyrol and rtk1; as well as other phylogentically related homologs such as eek, bsk, ehk1, ehk2, and cek7. The term "ortholog" refers to genes or proteins which are homologs via speciation, e.g., closely related and assumed to have common descent based on structural and functional considerations. Orthologous proteins function as recognizably the same activity in different species. The term "paralog" refers to genes or proteins which are homologs via gene duplication, e.g., duplicated variants of a gene within a genome. See also, Fritch, WM (1970) *Syst Zool* 19:99–113.

The phrases "modifies cellular activities" and "modulates cellular activities", with respect to the biological activity of the subject Elf-1 polypeptides, refers to changes which occur in a cell due to activation of intracellular signals, e.g., primary or secondary, by Elf-1 interaction with other cellular proteins. For example, such cellular activities which may be affected by Elf-1 include proliferation, differentiation or survival of a cell, as well as cell-cell adhesion and other alterations in phenotype. In one aspect, the cellular activities which can be modified by an Elf-1 polypeptide pertain to maintenance of neuronal connections. In general, the cellular modifications can be the relatively-direct biochemical consequence of signal transduction events, or can be caused more indirectly, such as Elf-1 dependent activation or inactivation of particular genes or gene programs. An Elf-1 polypeptide which "modifies" cellular activities can refer to homologs which either mimic or inhibit the normal response of a cell to the wild-type form of the protein.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

As used herein, the term "gene" or "recombinant gene" refers to a nucleic acid comprising an open reading frame encoding an Elf-1 polypeptide of the present invention, including both exon and (optionally) intron sequences. A "recombinant gene" refers to nucleic acid encoding an Elf-1 polypeptide and comprising Elf-1-encoding exon sequences, though it may optionally include intron sequences which are either derived from a chromosomal Elf-1 gene or from an unrelated chromosomal gene. An exemplary recombinant gene encoding a subject Elf-1 polypeptide is represented by SEQ ID No: 1; yet another is represented by SEQ ID No: 3. The term "intron" refers to a DNA sequence present in a given Elf-1 gene which is not translated into protein and is generally found between exons.

As used herein, the term "transfection" means the introduction of a nucleic acid, e.g., an expression vector, into a recipient cell by nucleic acid-mediated gene transfer. "Transformation", as used herein, refers to a process in which a cell's genotype is changed as a result of the cellular uptake of exogenous DNA or RNA, and, for example, the transformed cell expresses a recombinant form of an Elf-1 polypeptide or, where anti-sense expression occurs from the transferred gene, the expression of a naturally-occurring form of the. Elf-1 protein is disrupted.

As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

"Transcriptional regulatory sequence" is a generic term used throughout the specification to refer to DNA sequences, such as initiation signals, enhancers, and promoters, which induce or control transcription of protein coding sequences with which they are operably linked. In preferred embodiments, transcription of a recombinant Elf-1 gene is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring form of the Elf-1 protein.

As used herein, the term "tissue-specific promoter" means a DNA sequence that serves as a promoter, i.e., regulates expression of a selected DNA sequence operably linked to the promoter, and which effects expression of the selected DNA sequence in specific cells of a tissue, such as cells of neural origin, e.g. neuronal cells. The term also covers so-called "leaky" promoters, which regulate expression of a selected DNA primarily in one tissue, but cause expression in other tissues as well.

As used herein, a "transgenic animal" is any animal, preferably a non-human mammal, bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical crossbreeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant form of the subject Elf-1 protein, e.g. either agonistic or antagonistic forms. However, transgenic animals in which the recombinant Elf-1 gene is silent are also contemplated, as for example, the FLP or CRE recombinase dependent constructs described below. The "non-human animals" of the invention include vertebrates such as rodents, non-human primates, sheep, dog, cow, chickens, amphibians, reptiles, etc. Preferred non-human animals are selected from the rodent family including rat and mouse, most preferably mouse, though transgenic amphibians, such as members of the Xenopus genus, and transgenic chickens can also provide important tools for understanding, for example, embryogenesis. The term "chimeric animal" is used herein to refer to animals in which the recombinant gene is found, or in which the recombinant is expressed in some but not all cells of the animal. The term "tissue-specific chimeric animal" indicates that the recombinant Elf-1 gene is present and/or expressed in some tissues but not others.

As used herein, the term "transgene" means a nucleic acid sequence (encoding, e.g., an Elf-1 polypeptide), which is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can include one or more transcriptional regulatory sequences and any other nucleic acid, such as introns, that may be necessary for optimal expression of a selected nucleic acid.

As is well known, genes for a particular polypeptide may exist in single or multiple copies within the genome of an individual. Such duplicate genes may be identical or may have certain modifications, including nucleotide substitutions, additions or deletions, which all still code for polypeptides having substantially the same activity. The term "DNA sequence encoding an Elf-1 polypeptide" may thus refer to one or more genes within a particular individual. Moreover, certain differences in nucleotide sequences may exist between individual organisms, which are called alleles. Such allelic differences may or may not result in differences in amino acid sequence of the encoded polypeptide yet still encode a protein with the same biological activity.

"Homology" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 10 percent identity, though preferably less than 5 percent identity, with an Elf-1 sequence of the present invention.

"Cells,""host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A "chimeric protein" or "fusion protein" is a fusion of a first amino acid sequence encoding the subject Elf-1 polypeptide with a second amino acid sequence defining a domain foreign to and not substantially homologous with any domain of the Elf-1 protein. A chimeric protein may present a foreign domain which is found (albeit in a different protein) in an organism which also expresses the first protein, or it may be an "interspecies", "intergenic", etc. fusion of protein structures expressed by different kinds of organisms. In general, a fusion protein can be represented by the general formula X-elf-Y, wherein elf represents a portion of the protein which is derived from an Elf-1 protein, and X and Y are independently absent or represent amino acid sequences which are not related to an Elf-1 sequence.

The term "evolutionarily related to", with respect to nucleic acid sequences encoding an Elf-1 polypeptide, refers to nucleic acid sequences which have arisen naturally in an organism, including naturally occurring mutants. The term also refers to nucleic acid sequences which, while derived from a naturally occurring Elf-1 gene, have been altered by mutagenesis, as for example, the combinatorial mutagenic techniques described below, yet still encode polypeptides which have at least one activity of an Elf-1 polypeptide.

The term "isolated" as also used herein with respect to nucleic acids, such as DNA or RNA, refers to molecules separated from other DNAs, or RNAs, respectively, that are present in the natural source of the macromolecule. For example, an isolated nucleic acid encoding the subject Elf-1 polypeptides preferably includes no more than 10 kilobases (kb) of nucleic acid sequence which naturally immediately flanks the Elf-1 gene in genomic DNA, more preferably no more than 5 kb of such naturally occurring flanking sequences, and most preferably less than 1.5 kb of such naturally occurring flanking sequence. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state.

As described below, one aspect of the invention pertains to an isolated nucleic acid comprising the nucleotide sequence encoding an Elf-1 polypeptide, and/or equivalents of such nucleic acids. The term nucleic acid as used herein is intended to include fragments as equivalents. The term equivalent is understood to include nucleotide sequences encoding functionally equivalent Elf-1 polypeptides or functionally equivalent peptides which, for example, retain the ability to bind to an tyrosine kinase receptor of the EPH family, e.g. to the mek4-related and/or sek-related receptors. Equivalent nucleotide sequences will include sequences that differ by one or more nucleotide substitutions, additions or deletions, such as allelic variants; and will, therefore, include sequences that differ from the nucleotide sequence of the Elf-1 genes shown in SEQ ID Nos: 1 or 3 due to the degeneracy of the genetic code. Equivalents will also include nucleotide sequences that hybridize under stringent conditions (i.e., equivalent to about 20–27° C. below the melting temperature ($T_m$) of the DNA duplex formed in about 1M salt) to a nucleotide sequence represented by SEQ ID No: 1 and/or 3. In preferred embodiments, equivalents includes nucleic acid sequences derived from and evolutionarily related to, a nucleotide sequences shown in any of SEQ ID No: 1 or 3.

Moreover, it will be generally appreciated that, under certain circumstances, it may be advantageous to provide, homologs of the subject Elf-1 polypeptide which function in a limited capacity as one of either an Elf-1 agonist or an Elf-1 antagonist, in order to promote or inhibit only a subset of the biological activities of the naturally-occurring form of the protein. Thus, specific biological effects can be elicited by treatment with a homolog of limited function, and with fewer side effects relative to treatment with agonists or antagonists which are directed to all of the biological activities of naturally occuring forms of the Elf-1 protein. For instance, Elf-1 homologs can be generated which interfere with the ability of the wild-type protein in forming complexes with either the mek4 or sek receptor proteins, but which do not substantially interfere with the formation of complexes between the Elf-1 polypeptide and other members of the EPH receptor family, such as may be involved in other signal transduction mechanisms.

Homologs of the subject Elf-1 protein can be generated by mutagenesis, such as by discrete point mutation(s), or by truncation. For instance, mutation can give rise to homologs which retain substantially the same, or merely a subset, of the biological activity of the Elf-1 polypeptide from which it was derived. Alternatively, antagonistic forms of the protein can be generated which are able to inhibit the function of the naturally occurring form of the protein, such as by competitively binding to an EPH receptor, e.g. mek4 or sek.

A protein has Elf-1 polypeptide biological activity if it has one or more of the following properties: the ability to modulate proliferation, survival and/or differentiation of a cell which expresses an EPH receptor, such as a hek-related or sek-related receptor; the ability to modulate proliferation, survival and/or differentiation of mesodermally-derived tissue, such as tissue derived from dorsal mesoderm; the ability to modulate proliferation, survival and/or differentiation of ectodermally-derived tissue, such as tissue derived from the neural tube, neural crest, or head mesenchyme; the ability to modulate proliferation, survival and/or differentiation of endodermally-derived tissue, such as tissue derived from the primitive gut. In general, the ability to bind an EPH receptor protein, e.g. a mek4, hek, tyro4, cek4, sek cek8, or tyro1 receptor, is sufficient to characterize the polypeptide as an Elf-1 polypeptide of the present invention. Thus, according to the present invention, a polypeptide has biological activity if it is a specific agonist or antagonist of a naturally-occurring form of a Elf-1 protein.

Preferred nucleic acids encode an Elf-1 polypeptide comprising an amino acid sequence at least 70% homologous, more preferably 80% homologous and most preferably 85% homologous with an amino acid sequence shown in one of SEQ ID No: 2 or 4. Nucleic acids which encode polypeptides having an activity of an Elf-1 polypeptide and having an amino acid sequence at least about 90%, more preferably at least about 95%, and most preferably at least about 98–99% homology with a sequence shown in one of SEQ ID No: 2 or 4 are also within the scope of the invention. In one embodiment, the nucleic acid is a cDNA encoding a peptide having at least one activity of the subject Elf-1 polypeptide. Preferably, the nucleic acid is a cDNA molecule comprising at least a portion of the nucleotide sequence represented in SEQ ID No: 1 or 3. A preferred portion of this cDNA molecules includes the coding region of the gene.

Another aspect of the invention provides a nucleic acid which hybridizes under high or low stringency conditions to a nucleic acid which encodes a peptide having all or a portion of an amino acid sequence shown in SEQ ID No: 2 or 4. Appropriate stringency conditions which promote DNA hybridization, for example, 6.0 ×sodium chloride/sodium citrate (SSC) at about 45° C., followed by a wash of 2.0 ×SSC at 50° C., are known to those skilled in the art or can be found in *Current Protocols in Molecular Biology*, John Wiley & Sons, N.Y. (1989), 6.3.1–6.3.6. For example, the salt concentration in the wash step can be selected from a low stringency of about 2.0 ×SSC at 50° C. to a high stringency of about 0.2 ×SSC at 50° C. In addition, the temperature in the wash step can be increased from low stringency conditions at room temperature, about 22° C., to high stringency conditions at about 65° C.

Nucleic acids, having a sequence that differs from the nucleotide sequence shown in SEQ ID No: 1 or 3 due to degeneracy in the genetic code are also within the scope of the invention. Such nucleic acids encode functionally equivalent peptides (i.e., a peptide having a biological activity of an Elf-1 polypeptide) but differ in sequence from the sequence shown in the sequence listing due to degeneracy in the genetic code. For example, a number of amino acids are designated by more than one triplet. Codons that specify the same amino acid, or synonyms (for example, CAU and CAC each encode histidine) may result in "silent" mutations which do not affect the amino acid sequence of the Elf-1 polypeptide. However, it is expected that DNA sequence polymorphisms that do lead to changes in the amino acid sequences of the subject Elf-1 polypeptides will exist among vertebrates. One skilled in the art will appreciate that these variations in one or more nucleotides (up to about 3–5% of the nucleotides) of the nucleic acids encoding polypeptides having an activity of an Elf-1 polypeptide may exist among individuals of a given species due to natural allelic variation. Any and all such nucleotide variations and resulting amino acid polymorphisms are within the scope of this invention.

Fragments of the nucleic acids encoding an active portion of the Elf-1 protein are also within the scope of the invention. As used herein, a fragment of the nucleic acid encoding the active portion of an Elf-1 polypeptide refers to a nucleic acid having fewer nucleotides than the nucleotide sequence encoding the entire amino acid sequence of the Elf-1 protein represented in SEQ ID No: 2 or 4, but which nevertheless encodes a peptide having an Elf-1 polypeptide biological activity, e.g. the fragment retains the ability to bind to an EPH receptor such as mek4 or sek. For instance, Elf-1 polypeptides can be provided which lack an endogenous signal sequence or a phosphatidylinositol attachement site. Nucleic acid fragments -within the scope of the present invention include those capable of hybridizing under high or low stringency conditions with nucleic acids from other species for use in screening protocols to detect Elf-1 homologs, as well as those capable of hybridizing with nucleic acids from human specimens for use in detecting the presence of a nucleic acid encoding the subject Elf-1 protein, including alternate isoforms, e.g. mRNA splicing variants. Nucleic acids within the scope of the invention may also contain linker sequences, modified restriction endonuclease sites and other sequences useful for molecular cloning, expression or purification of recombinant forms of the subject Elf-1 polypeptides.

As indicated by the examples set out below, a nucleic acid encoding a peptide having an activity of an Elf-1 polypeptide may be obtained from mRNA present in any of a number of eukaryotic cells. It should also be possible to obtain nucleic acids encoding Elf-1 polypeptides of the present invention from genomic DNA obtained from both adults and embryos. For example, a gene encoding an Elf-1 protein can be cloned from either a cDNA or a genomic library in accordance with protocols described herein, as well as those generally known to persons skilled in the art. A cDNA encoding an Elf-1 protein can be obtained by isolating total mRNA from a cell, e.g. a mammalian cell, e.g. a human cell, including embryonic cells. Double stranded cDNAs can then be prepared from the total mRNA, and subsequently inserted into a suitable plasmid or bacteriophage vector using any one of a number of known techniques. The gene encoding the Elf-1 protein can also be cloned using established polymerase chain reaction techniques in accordance with the nucleotide sequence information provided by the invention. The nucleic acid of the invention can be DNA or RNA. A preferred nucleic acid is a cDNA represented by a nucleotide sequence shown in SEQ ID No: 1 or 3.

Another aspect of the invention relates to the use of the isolated nucleic acid in "antisense" therapy. As used herein, "antisense" therapy refers to administration or in situ generation of oligonucleotide probes or their derivatives which specifically hybridizes (e.g. binds) under cellular conditions, with the cellular mRNA and/or genomic DNA encoding an Elf-1 protein so as to inhibit expression of that protein, e.g. by inhibiting transcription and/or translation. The binding may be by conventional base pair complementarity, or, for example, in the case of binding to DNA duplexes, through specific interactions in the major groove of the double helix. In general, "antisense" therapy refers to the range of techniques generally employed in the art, and includes any therapy which relies on specific binding to oligonucleotide sequences.

An antisense construct of the present invention can be delivered, for example, as an expression plasmid which, when transcribed in the cell, produces RNA which is complementary to at least a unique portion of the cellular mRNA which encodes an Elf-1 protein. Alternatively, the antisense construct is an oligonucleotide probe which is generated ex vivo and which, when introduced into the cell causes inhibition of expression by hybridizing with the mRNA and/or genomic sequences of am Elf-1 gene. Such oligonucleotide probes are preferably modified oligonucleotide which are resistant to endogenous nucleases, e.g. exonucleases and/or endonucleases, and is therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by van der krol et al. (1988) *Biotechniques* 6:958–976; and Stein et al. (1988) *Cancer Res* 48:2659–2668.

Accordingly, the modified oligomers of the invention are useful in therapeutic, diagnostic, and research contexts. In therapeutic applications, the oligomers are utilized in a manner appropriate for antisense therapy in general. For such therapy, the oligomers of the invention can be formulated for a variety of loads of administration, including systemic and topical or localized administration. Techniques and formulations generally may be found in *Remmington's Pharmaceutical Sciences,* Meade Publishing Co., Easton, Pa. For systemic administration, injection is preferred, including intramuscular, intravenous, intraperitoneal, and subcutaneuos for injection, the oligomers of the invention can be formulated in liquid solutions, preferably in physiologically compatible buffers such as Hank's solution or Ringer's solution. In addition, the oligomers may be formulated in solid form and redissolved or suspended immediately prior to use. Lyophilized forms are also included.

Systemic administration can also be by transmucosal or transdermal means, or the compounds can be administered orally. For transmucosal or transdermal administration, penetrants appropriate to the barrier to be permeated- are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For oral administration, the oligomers are formulated into conventional oral administration forms such as capsules, tablets, and tonics. For topical administration, the oligomers of the invention are formulated into ointments, salves, gels, or creams as generally known in the art.

In addition to use in therapy, the oligomers of the invention may be used as diagnostic reagents to detect the presence or absence of the target DNA or RNA sequences to which they specifically bind. Such diagnostic tests are described in further detail below.

Likewise, the antisense constructs of the present invention, by antagonizing the normal biological activity of Elf-1, can be used in the manipulation of tissue, e.g. tissue differentiation, both in vivo and in ex vivo tissue cultures.

This invention also provides expression vectors containing a nucleic acid encoding an Elf-1 polypeptide, operably linked to at least one transcriptional regulatory sequence. Operably linked is intended to mean that the nucleotide sequence is linked to a regulatory sequence in a manner which allows expression of the nucleotide sequence. Regulatory sequences are art-recognized and are selected to direct expression of the subject Elf-1 proteins. Accordingly, the term transcriptional regulatory sequence includes promoters, enhancers and other expression control elements. Such regulatory sequences are described in Goeddel; *Gene Expression Technology: Methods in Enzymology* 185, Academic Press, San Diego, Calif. (1990). For instance, any of a wide variety of expression control sequences—sequences that control the expression of a DNA sequence when operatively linked to it may be used in these vectors to express DNA sequences encoding the Elf-1 polypeptides of this invention. Such useful expression control sequences, include, for example, a viral LTR, such as the LTR of the Moloney murine leukemia virus, the early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage λ, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other 'sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other proteins encoded by the vector, such as antibiotic markers, should also be considered. In one embodiment, the expression vector includes a recombinant gene encoding a peptide having an agonistic activity of a subject Elf-1 polypeptide, or alternatively, encoding a peptide which is an antagonistic form of the Elf-1 protein. Such expression vectors can be used to transfect cells and thereby produce proteins or peptides, including fusion proteins or peptides, encoded by nucleic acids as described herein.

Moreover, the gene constructs of the present invention can also be used as a part of a gene therapy protocol to deliver nucleic acids encoding either an agonistic or antagonistic form of the subject Elf-1 protein. Thus, another aspect of the invention features expression vectors for in vivo transfection and expression of an Elf-1 polypeptide in particular cell types so as to reconstitute the function of, or alternatively, abrogate the function of Elf-1 in a tissue in which Elf-1 is misexpressed; or to deliver a form of the protein which alters differentiation of tissue, or which inhibits neoplastic transformation, by modulating the biological function of an EPH receptor (e.g., the mek4 or sek receptors).

Expression constructs of the subject Elf-1 polypeptide, and mutants thereof, may be administered in any biologically effective carrier, e.g. any formulation or composition capable of effectively delivering the Elf-1 gene to cells in vivo. Approaches include insertion of the subject gene in viral vectors including recombinant retroviruses, adenovirus, adeno-associated virus, and herpes simplex virus- 1, or recombinant bacterial or eukaryotic plasmids. Viral vectors transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or $CaPO_4$ precipitation carried out in vivo. It will be appreciated that because transduction of appropriate target cells represents the critical first step in gene therapy, choice of the particular gene delivery system will depend on such factors as the phenotype of the intended target and the route of administration, e.g. locally or systemically. Furthermore, it will be recognized that the particular gene construct provided for in vivo transduction of Elf-1 expression are also useful for in vitro transduction of cells, such as for use in the ex vivo tissue culture systems described below.

A preferred approach for in vivo introduction of nucleic acid into a cell is by use of a viral vector containing nucleic acid, e.g. a cDNA, encoding the particular form of the Elf-1 polypeptide desired. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors are generally understood to be the recombinant gene delivery system of choice for the transfer of exogenous genes in vivo, particularly into humans. These vectors provide efficient delivery of genes into cells, and the transferred nucleic acids are stably integrated into the chromosomal DNA of the host. A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller, A.D. (1990) *Blood* 76:271). Thus, recombinant retrovirus can be constructed in which part of the retroviral coding sequence (gag, pol, env) has been replaced by nucleic acid encoding one of the subject receptors rendering the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in *Current Protocols in Molecular Biology,* Ausubel, F.M. et al. (eds.) Greene Publishing Associates, (1989), Sections 9.10–9.14 and other standard laboratory manuals. Examples of suitable retroviruses include pLJ, pZIP, pWE and pEM which are well known to those skilled in the art. Examples of suitable packaging virus lines for preparing both ecotropic and amphotropic retroviral systems include ψCrip, ψCre, ψ2 and ψAm. Retroviruses have been used to introduce a variety of genes into many different cell types, including neuronal cells, in vitro and/or in vivo (see for example Eglitis, et al. (1985) *Science* 230:1395–1398; Danos and Mulligan (1988) *Proc. Natl. Acad. Sci.* USA 85:6460–6464; Wilson et al. (1988) *Proc. Natl. Acad. Sci.* USA 85:3014–3018; Armentano et al. (1990) *Proc. Natl. Acad Sci.* USA 87:6141–6145; Huber et al. (1991) *Proc. Natl. Acad Sci.* USA 88:8039–8043; Ferry et al. (1991) *Proc. Natl. Acad. Sci.* USA 88:8377–8381; Chowdhury et al. (1991) *Science* 254:1802–1805; van Beusechem et al. (1992) *Proc. Natl. Acad Sci.* USA 89:7640–7644; Kay et al. (1992) *Human Gene Therapy* 3:641–647; Dai et al. (1992) *Proc. Natl. Acad Sci.* USA 89:10892–10895; Hwu et al. (1993) *J Immunol.* 150:4104–4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

Furthermore, it has been shown that it is possible to limit the infection spectrum of retroviruses and consequently of retroviral-based vectors, by modifying the viral packaging proteins on the surface of the viral particle (see, for example PCT publications W093/25234 and W094/06920). For instance, strategies for the modification of the infection spectrum of retroviral vectors include: coupling antibodies specific for cell surface antigens to the viral env protein (Roux et al. (1989) *PNAS* 86:9079–9083; Julan et al. (1992) *J. Gen Virol* 73:3251–3255; and Goud et al. (1983) *Virology* 163:251–254); or coupling cell surface receptor ligands to the viral env proteins (Neda et al. (1991) *J Biol Chem* 266:14143–14146). Coupling can be in the form of the chemical cross-linking with a protein or other variety (e.g. lactose to convert the env protein to an asialoglycoprotein), as well as by generating fusion proteins (e.g. single-chain antibody/env fusion proteins). This technique, while useful to limit or otherwise direct the infection to certain tissue types, can also be used to convert an ecotropic vector in to an amphotropic vector.

Moreover, use of retroviral gene delivery can be further enhanced by the use of tissue-or cell-specific transcriptional regulatory sequences which control expression of the Elf-1 gene of the retroviral vector.

Another viral gene delivery system useful in the present invention utilizes adenovirus-derived vectors. The genome of an adenovirus can be manipulated such that it encodes and expresses a gene product of interest but is inactivated in terms of its ability to replicate in a normal lytic viral life cycle. See for example Berkner et al. (1988) *BioTechniques* 6:616; Rosenfeld et al. (1991) *Science* 252:431–434; and Rosenfeld et al. (1992) *Cell* 68:143–155. Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses can be advantageous in certain circumstances in that they are not capable of infecting nondividing cells and can be used to infect a wide variety of cell types, including epithelial cells (Rosenfeld et al. (1992) cited supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) *J. Virol.* 57:267). Most replication-defective adenoviral vectors currently in use and therefore favored by the present invention are deleted for all or parts of the viral E1 and E3 genes but retain as much as 80% of the adenoviral genetic material (see, e.g., Jones et al. (1979) *Cell* 16:683; Berkner et al., supra; and Graham et al. in *Methods in Molecular Biology*, E. J. Murray, Ed. (Hurnana, Clifton, N.J., 1991) vol. 7. pp. 109–127). Expression of the inserted Elf-1 gene can be under control of, for example, the E1A promoter, the major late promoter (MLP) and associated leader sequences, the E3 promoter, or exogenously added promoter sequences.

Yet another viral vector system useful for delivery of the subject Elf-1 gene is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al. *Curr. Topics in Micro. and Immunol.* (1992) 158:97–129). It is also one of the few viruses that may integrate its DNA into non-dividing cells, and exhibits a high frequency of stable integration (see for example Flotte et al. (1992) *Am. J Respir. Cell. Mol. Biol.* 7:349–356; Samulski et al. (1989) *J. Virol.* 63:3822–3828; and McLaughlin et al. (1989) *J. Virol.* 62:1963–1973). Vectors containing as little as 300 base pairs of AAV can be packaged and can integrate. Space for exogenous DNA is limited to about 4.5 kb. An AAV vector such as that described in Tratschin et al. (1985) *Mol. Cell. Biol.* 5:3251–3260 can be used to introduce DNA into cells. A variety of nucleic acids have been introduced into different cell types using AAV vectors (see for example Hermonat et al. (1984) *Proc. Natl. Acad Sci.* USA 81:6466–6470; Tratschin et al. (1985) *Mol. Cell. Biol.* 4:2072–2081; Wondisford et al. (1988) *Mol. Endocrinol.* 2:32–39; Tratschin et al. (1984) *J. Virol.* 51:611–619; and Flotte et al. (1993) *J. Biol. Chem.* 268:3781–3790).

In addition to viral transfer methods, such as those illustrated above, non-viral methods can also be employed to cause expression of an Elf-1 polypeptide in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the subject Elf-1 polypeptide gene by the targeted cell. Exemplary gene delivery systems of this type include liposomal derived systems, poly-lysine conjugates, and artificial viral envelopes.

In a representative embodiment, a gene encoding one of the subject Elf-1 polypeptides can be entrapped in liposomes bearing positive charges on their surface (e.g., lipofectins) and (optionally) which are tagged with antibodies against cell surface antigens of the target tissue (Mizuno et al. (1992) *No Shinkei Geka* 20:547–551; PCT publication W091/06309; Japanese patent application 1047381; and European patent publication EP-A-43075). For example, lipofection of cells can be carried out using liposomes tagged with monoclonal antibodies against any cell surface antigen present on the tumor cells, as for example, the CD20 antigen which has been detected on the lymphoblastic cell line LK63/CD20+which also expresses the hek receptor (Wicks et al. (1992) *PNAS* 89:1611–1615).

In clinical settings, the gene delivery systems for the therapeutic Elf-1 gene can be introduced into a patient by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al. (1994) *PNAS* 91: 3054–3057).

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced intact from recombinant cells, e.g. retroviral vectors, the pharmaceutical preparation can comprise one or more cells which produce the gene delivery system.

Another aspect of the present invention concerns recombinant forms of the subject Elf-1 protein which are encoded by genes derived from eukaryotic organisms such as mammals, e.g. humans. Recombinant proteins preferred by the present invention, in addition to native Elf-1 polypeptides, are at least 70% homologous, more preferably at least 80% homologous and most preferably at least 85% homologous with an amino acid sequence shown in either or both of SEQ ID No: 2 or 4. Polypeptides having an activity of the subject Elf-1 polypeptides (i.e. either agonistic or antagonistic) and having at least about 90%, more preferably at least about 95%, and most preferably at least about 98–99% homology with a polypeptide sequence in SEQ ID No: 2 or 4 are also within the scope of the invention.

The term "recombinant protein" refers to a polypeptide of the present invention which is produced by recombinant DNA techniques, wherein generally DNA encoding an Elf-1 polypeptide is inserted into a suitable expression vector which is in turn used to transform a host cell to produce the heterologous protein. Moreover, the phrase "derived from", with respect to a recombinant Elf-1 gene, is meant to include within the meaning of "recombinant protein" those proteins having an amino acid sequence of a native Elf-1polypeptide, or an amino acid sequence similar thereto which is generated by mutations including substitutions and deletions (including truncation) of a naturally occurring form of an Elf-1 protein. For instance, N-glycosylation sites in the Elf-1 protein can be modified (e.g. mutated) to preclude glycosylation, allowing expression of a more homogenous, reduced carbohydrate analog in mammalian, insect and yeast expression systems. The wild-type protein contains three potential N-linked glycosylation sites which can be mutated: e.g., Asn-38, Asn-170 and Asn-184 of muElf-1.

Likewise, Elf-1 polypeptides can be generated which lack an endogenous signal sequence (though this is typically cleaved off even if present in the pro-form of the protein), or which lack a glycosyl-phosphatidylinositol (gpi) linkage site to preclude addition of gpi moieties to the polypeptide. In the instance of the latter, the removal of the C-terminus may result in a soluble form of the protein. In particular, polypeptides which lack at least the last 15 amino acid residues (e.g. equivalent to muElf-1 truncated at Leu-195) are preferred as soluble forms of the protein, though polypeptides which are truncated anywhere between the equivalent of Thr-182 to Leu-195 of the muElf-1 protein are also contemplated.

Furthermore, comparison of the subject protein with the other EPH receptor ligands known, namely B61 (Bartley et al. (1994) *Nature* 368:558–561; and Holzman et al. (1990) *Mol Cell Biol* 10:5830–5838) and LERK-2 (Beckmann et al. (1994) *EMBO J*13:3757–3762; PCT Publication W095/ 11384), suggests that the biological activity of the molecule resides largely in the region of the protein containing the four cysteines whose spacing is apparently conserved so as to suggest an important motif, referred to herein as a "$Cys_4$ motif". Consequently, a preferred Elf-1 polypeptide comprises Cys-69 through Cys-159 of SEQ ID No. 2, or a sequence homologous thereto. Other exemplary $Cys_4$ motifs are bounded by residues 61–150 of SEQ ID No. 4, or represented by residues 39–129 of SEQ ID No. 5. Truncated forms of the subject Elf-1 polypeptides, therefore, may be cropped at or in the vicinity of the C-terminus of the $Cys_4$ motif.

In similar fashion, a "core sequence motif" within the EPH receptor ligands is also recognized. This core sequence motif, slightly larger that the $Cys_4$ motif, is suggested by higher sequence homologies over a portion of the protein sequences relative to the full-length, mature protein (see Table 1, Example 10). Similar to the $Cys_4$ motif, the core sequence motif presumably represents a fragment which retains at least a portion of the activity of the mature protein, with the exception of a phosphatidylinositol attachment sequence. The core sequence motif of Elf-1 is defined by residues 35–166 of SEQ ID No. 2, residues 33–157 of SEQ ID No. 4, and residues 5–136 of SEQ ID No. 5, with analogous core sequence motifs for other Elf-1 polypeptides readily ascertainable by comparison with these sequences. Accordingly, truncated forms of the subject Elf-1 polypeptides may be truncated at or in the vicinity of the C-terminus of the core sequence motif.

The present invention further pertains to recombinant forms of the subject Elf-1 polypeptides which are encoded by genes derived from a vertebrate organism, particularly a mammal (e.g. a human), and which have amino acid sequences evolutionarily related to the Elf-1 proteins represented in SEQ ID No: 2 or 4. Such recombinant Elf-1 polypeptides are preferably capable of functioning in one of either role of an agonist or antagonist of at least one biological activity of the Elf-1 polypeptide of the appended sequence listing. The term "evolutionarily related to", with respect to amino acid sequences of the present recombinant Elf-1 polypeptides, refers to Elf-1 polypeptides having amino acid sequences which have arisen naturally, and also to mutational variants of Elf-1 polypeptides which are derived, for example, by combinatorial mutagenesis. Such evolutionarily derived Elf-1 polypeptides preferred by the present invention are at least 70% homologous, more preferably at least 80% homologous and most preferably at least 85% homologous with an amino acid sequence shown in SEQ ID No: 2 and/or 4. Polypeptides having at least about 90%, more preferably at least about 95%, and most preferably at least about 98–99% homology with a sequence shown in SEQ ID No: 2, 4 or 5 are also within the scope of the invention.

The present invention further pertains to methods of producing the subject Elf-1 polypeptides. For example, a host cell transfected with a nucleic acid vector directing expression of a nucleotide sequence encoding the subject Elf-1 polypeptide can be cultured under appropriate conditions to allow expression of the peptide to occur. The peptide may be secreted and isolated from a mixture of cells and medium containing the recombinant Elf-1 polypeptide. Alternatively, the peptide may be retained cytoplasmically by removing the signal peptide sequence from the recombinant Elf-1 gene and the cells harvested, lysed and the protein isolated. A cell culture includes host cells, media and other byproducts. Suitable media for cell culture are well known in the art. The recombinant Elf-1 polypeptide peptide can be isolated from cell culture medium, host cells, or both using techniques known in the art for purifying proteins including ion-exchange chromatography, gel filtration chromatography, ultrafiltration, electrophoresis, and immunoaffinity purification with antibodies specific for such peptide. In a preferred embodiment, the recombinant Elf-1 polypeptide is a fusion protein containing a domain which facilitates its purification, such as an Elf-1/GST fusion protein.

This invention also pertains to a host cell transfected to express a recombinant form of the subject Elf-1 polypeptides. The host cell may be any prokaryotic or eukaryotic cell, and the choice can be based at least in part on the desirablity of such post-translation modifications as glycosylation and/or addition of phosphatidylinositol. Thus, a nucleotide sequence derived from the cloning of Elf-1, encoding all or a selected portion of the full-length protein, can be used to produce a recombinant form of an Elf-1 polypeptide via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial cells), are standard procedures used in producing other well-known proteins, e.g. insulin, interferons, human growth hormone, IL-1, IL-2, and the like. Similar procedures, or modifications thereof, can be employed to prepare recombinant Elf-1 polypeptides by microbial means or tissue-culture technology in accord with the subject invention.

The recombinant Elf-1 gene can be produced by ligating nucleic acid encoding the subject Elf-1 protein, or a portion thereof, into a vector suitable for expression in either prokaryotic cells, eukaryotic cells, or both. Expression vectors for production of recombinant forms of the subject Elf-1 polypeptides include plasmids and other vectors. For instance, suitable vectors for the expression of an Elf-1 polypeptide include plasmids of the types: pBR322-derived plasmids, pEMBL-derived plasmids, pEX-derived plasmids, pBTac-derived plasmids and pUC-derived plasmids for expression in prokaryotic cells, such as E. coli.

A number of vectors exist for the expression of recombinant proteins in yeast. For instance, YEP24, YIP5, YEP51, YEP52, pYES2, and YRP17 are cloning and expression vehicles useful in the introduction of genetic constructs into S. cerevisiae (see, for example, Broach et al. (1983) in Experimental Manipulation of Gene Expression, ed. M. Inouye Academic Press, p. 83, incorporated by reference herein). These vectors can replicate in E. coli due the presence of the pBR322 ori, and in S. cerevisiae due to the replication determinant of the yeast 2 micron plasmid. In addition, drug resistance markers such as ampicillin can be used. In an illustrative embodiment, an Elf-1 polypeptide is produced recombinantly utilizing an expression vector generated by sub-cloning the coding sequence of an Elf-1 gene represented in SEQ ID NO. 1 or 3.

The preferred mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papillomavirus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see Molecular Cloning A Laboratory Manual, 2nd Ed., ed. by Sambrook, Fritsch and Maniatis (Cold Spring Harbor Laboratory Press: 1989) Chapters 16 and 17. In some instances, it may be desirable to express the recombinant Elf-1 polypeptide by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

When it is desirable to express only a portion of an Elf-1 protein, such as a form lacking a portion of the N-terminus, i.e. a trunction mutant which lacks the signal peptide, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from E. coli (Ben-Bassat et al. (1987) J. Bacteriol. 169:751–XX57) and Salmonella typhimurium and its in vitro activity has been demonstrated on recombinant proteins (Miller et al. (1987) PNAS 84:2718–1722). Therefore, removal of an N-terminal methionine, if desired, can be achieved either in vivo by expressing Elf-1-derived polypeptides in a host which produces MAP (e.g., E. coli or CM89 or S. cerevisiae), or in vitro by use of purified MAP (e.g., procedure of Miller et al., supra).

Alternatively, the coding sequences for the polypeptide can be incorporated as a part of a fusion gene including a nucleotide sequence encoding a different polypeptide. This type of expression system can be useful under conditions where it is desirable to produce an immunogenic fragment of an Elf-1 protein. For example, the VP6 capsid protein of rotavirus can be used as an immunologic carrier protein for portions of the Elf-1 polypeptide, either in the monomeric form or in the form of a viral particle. The nucleic acid sequences corresponding to the portion of a subject Elf-1 protein to which antibodies are to be raised can be incorporated into a fusion gene construct which includes coding sequences for a late vaccinia virus structural protein to produce a set of recombinant viruses expressing fusion proteins comprising Elf-1 epitopes as part of the virion. It has been demonstrated with the use of immunogenic fusion proteins utilizing the Hepatitis B surface antigen fusion proteins that recombinant Hepatitis B virions can be utilized in this role as well. Similarly, chimeric constructs coding for fusion proteins containing a portion of an Elf-1 protein and the poliovirus capsid protein can be created to enhance immunogenicity of the set of polypeptide antigens (see, for example, EP Publication No: 0259149; and Evans et al. (1989) Nature 339:385; Huang et al. (1988) J. Virol. 62:3855; and Schlienger et al. (1992) J. Virol. 66:2).

The Multiple Antigen Peptide system for peptide-based immunization can also be utilized to generate an immunogen, wherein a desired portion of an Elf-1 polypeptide is obtained directly from organo-chemical synthesis of the peptide onto an oligomeric branching lysine core (see, for example, Posnett et al. (1988) JBC 263:1719 and Nardelli et al. (1992) J. Immunol. 148:914). Antigenic determinants of Elf-1 proteins can also be expressed and presented by bacterial cells.

In addition to utilizing fusion proteins to enhance immunogenicity, it is widely appreciated that fusion proteins can also facilitate the expression of proteins, including the Elf-1 polypeptides of the present invention. For example, an Elf-1 polypeptide can be generated as a glutathione-S-transferase (GST-fusion protein). Such GST-fusion proteins can enable easy purification of the Elf-1 polypeptide, as for example by the use of glutathione-derivatized matrices (see, for example, Current Protocols in Molecular Biology, eds. Ausubel et al. (N.Y.: John Wiley & Sons, 1991)). In another embodiment, a fusion gene coding for a purification leader sequence, such as a poly-(His)/enterokinase cleavage site sequence, can be used to replace the signal sequence which naturally occurs at N-terminus the Elf-1 protein, in order to permit purification of the poly-(His)-Elf-1 protein by affinity chromatography using a $Ni^{2+}$metal resin. The purification leader sequence can then be subsequently removed by treatment with enterokinase (e.g., see Hochuli et al. (1987) J. Chromatography 411:177; and Janknecht et al. PNAS 88:8972).

Furthermore, the generation of Elf-1 fusion proteins can be utilized as means for facilitating clustering, e.g., oligomerization, of Elf-1 proteins to enhance certain activities associated with, for example, receptor cross-linking. The Elf-1/alkaline phosphatase fusion protein described herein may provide such a function, relying on the ability of alkaline phosphatase domains to promote complex formation between two or more Elf-1/AP proteins. Moreover, it may be desirable to provide multiple Elf-1 domains in the same molecule, rather than rely on intermolecular complementation for oligomerization. For instance, an unstructured polypeptide linker region can be introduced between two Elf-1 portions of the fusion protein. This linker can facilitate enhanced flexibility of the fusion protein, allowing the Elf-1 domains to freely interact through intramolecular association, e.g., because of reduced steric hindrance between the two fragments, as well as permit appropriate folding of each fragment to occur. The linker can be of natural origin, such as a sequence determined to exist in random coil between two domains of a protein. Alternatively, the linker can be of synthetic origin. For instance, the sequence $(Gly_4Ser)_3$ can be used as a synthetic unstructured linker. Linkers of this type are described in Huston et al. (1988) *PNAS* 85:4879; and U.S. Pat. No. 5,091,513, both incorporated by reference herein.

Techniques for making fusion genes are known to those skilled in the art. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al. John Wiley & Sons: 1992).

The Elf-1 polypeptide may also be chemically modified to create Elf-1 derivatives by forming covalent or aggregrative conjugates with other chemical moieties, such as glycosyl groups, lipids, phosphate, acetyl groups and the like. Covalent derivatives of Elf-1 can be prepared by linking the chemical moeities to functional groups on Elf-1 amino acid sidechains or at the N-terminus or at the C-terminus of the polypeptide. For instance, an Elf-1 protein can generated which includes a moiety, other than sequences naturally associated with the Elf-1 protein, that binds a component of the extracellular matrix and enhances localization of the Elf-1 analog to cell surfaces. For example, sequences derived from the fibronectin "type-III repeat", such as a tetrapeptide sequence R-G-D-S (Pierschbacher et al. (1984) *Nature* 309:30–3; and Komblihtt et al. (1985) *EMBO* 4:1755–9) can be added to the Elf-1 polypepyide to support attachment of the chimeric molecule to a cell through binding ECM components (Ruoslahti et al. (1987) *Science* 238:491–497; Pierschbacheret al. (1987) *J. Biol. Chem.* 262:17294–8.; Hynes (1987) *Cell* 48:549–54; and Hynes (1992) *Cell* 69:11–25) particularly where the Elf-1 polypeptide lacks a C-terminal phosphatidylinositol.

The present invention also makes available isolated Elf-1 polypeptides which are isolated from, or otherwise substantially free of other cellular and extracellular proteins, especially EPH receptor proteins or other extracellular factors, normally associated with the Elf-1 polypeptide. The term "substantially free of other cellular or extracellular proteins" (also referred to herein as "contaminating proteins") or "substantially pure or purified preparations" are defined as encompassing preparations of Elf-1 polypeptides having less than 20% (by dry weight) contaminating protein, and preferably having less than 5% contaminating protein. Functional forms of the subject Elf-1 polypeptides can be prepared, for the first time, as purified preparations by using a cloned gene as described herein. Alternatively, the subject Elf-1 polypeptides can be isolated by affinity purification using, for example, matrix bound EPH receptor protein. By "purified", it is meant, when referring to a peptide or DNA or RNA sequence, that the indicated molecule is present in the substantial absence of other biological macromolecules, such as other proteins. The term "purified" as used herein preferably means at least 80% by dry weight, more preferably in the range of 95–99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above. "Isolated" and "purified" do not encompass either natural materials in their native state or natural materials that have been separated into components (e.g., in an acrylamide gel) but not obtained either as pure (e.g. lacking contaminating proteins, or chromatography reagents such as denaturing agents and polymers, e.g. acrylamide or agarose) substances or solutions.

As described above for recombinant polypeptides, isolated Elf-1 polypeptides can include all or a portion of an amino acid sequence represented in SEQ ID No. 2, 4 or 5, or homologous sequence thereto. Exemplary derivatives of that sequence include proteins which lack N-glycosylation sites (e.g. to produce an unglycosylated protein), or which lack an N-terminus and or/C-terminus sequence, e.g. an Elf-1 polypeptide which consists essentially of (with respect to receptor binding) a $Cys_4$ motif or a core sequence motif, or a sequence homologous thereto.

Furthermore, isolated peptidyl portions of Elf-1 proteins can also be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, an Elf-1 polypeptide of the present invention may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of an Elf-1 polypeptide activity, such as by in vivo competition assays or in vitro protein binding assays with EPH receptors.

It will also be possible to modify the structure of the subject Elf-1 polypeptides for such purposes as enhancing therapeutic or prophylactic efficacy, or stability (e.g., ex vivo shelf life and resistance to proteolytic degradation in vivo). Such modified peptides, when designed to retain at least one activity of the naturally-occurring form of the protein, are considered functional equivalents of the Elf-1 polypeptide described in more detail herein. Such modified peptide can be produced, for instance, by amino acid substitution, deletion, or addition.

For example, it is reasonable to expect that an isolated replacement of a leucine with an isoleucine or valine, an aspartate with a glutamate, a threonine with a serine, or a similar replacement of an amino acid with a structurally related amino acid (i.e. conservative mutations) will not have a major effect on the biological activity of the resulting molecule. Conservative replacements are those that take place within a family of amino acids that are related in their side chains. Genetically encoded amino acids are can be divided into four families: (1) acidic=aspartate, glutamate; (2) basic=lysine, arginine, histidine; (3) nonpolar =alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan, and tyrosine are sometimes classified jointly as aromatic amino acids. In similar fashion, the amino acid repertoire can be grouped as (1) acidic=aspartate, glutamate; (2) basic=lysine, arginine histidine, (3) aliphatic= glycine, alanine, valine, leucine, isoleucine, serine, threonine, with serine and threonine optionally be grouped separately as aliphatic-hydroxyl; (4) aromatic= phenylalanine, tyrosine, tryptophan; (5) amide=asparagine, glutamine; and (6) sulfur -containing=cysteine and methionine. (see, for example, *Biochemistry,* 2nd ed., Ed. by L. Stryer, WH Freeman and Co.: 1981). Whether a change in the amino acid sequence of a peptide results in a functional Elf-1 homolog (e.g. functional in the sense that it acts to mimic or antagonize the wild-type form) can be readily determined by assessing the ability of the variant peptide to produce a response in cells in a fashion similar to the wild-type Elf-1 protein or competitively inhibit such a response. Peptides in which more than one replacement has taken place can readily be tested in the same manner.

Accordingly, the present invention contemplates a method of generating sets of combinatorial mutants of the presently disclosed novel Elf-1 polypeptides, as well as truncation and fragmentation mutants, and is especially useful for identifying potential variant sequences which are functional in binding to an EPH receptor. One purpose for screening such combinatorial libraries is, for example, to isolate novel Elf-1 homologs which function as one of either an agonist or antagonist of the biological activities of the wild-type ("authentic") protein, or alternatively, which possess novel activities all together. To illustrate, Elf-1 homologs can be engineered by the present method to provide proteins which bind an EPH receptor, such as mek4/cek4/hek/tyro4 or sek/cek8/tyrol receptors, yet which block receptor-mediated gene transcription resulting from signal transduction pathways normally associated with activation of that receptor. Such proteins, when expressed from recombinant DNA constructs, can be used in gene therapy protocols, or can be formulated as pharmaceutical preparations and delivered in such manner.

Likewise, mutagenesis can give rise to Elf-1 homologs which have extracellular half-lives dramatically different than the corresponding wild-type protein. For example, the altered protein can be rendered either more stable or less stable to proteolytic degradation or other extracellular process which result in destruction of, or otherwise inactivation of, an Elf-1 polypeptide. Such Elf-1 homologs can be utilized to alter the envelope of bioavailabilty for a recombinant Elf-1 protein by modulating, for example, the plasma half-life of the protein. For instance, a short half-life can give rise to more transient biological effects associated with a particular recombinant Elf-1 polypeptide and can therefore allow tighter control of protein levels within or around a particular tissue. As above, such proteins, and particularly their recombinant nucleic acid constructs, can be used in gene therapy protocols as well as formulated into pharmaceutical preparations.

In an illustrative embodiment of this method, the amino acid sequences for a population of Elf-1 homologs or other related proteins are aligned, preferably to promote the highest homology possible. Such a population of variants can include, for example, Elf-1 homologs from one or more species, e.g. murine and chicken, or Elf-1 homologs from the same species but which differ due to mutation. Amino acids which appear at each position of the aligned sequences are selected to create a degenerate set of combinatorial sequences. In a preferred embodiment, the variegated library of Elf-1 variants is generated by combinatorial mutagenesis at the nucleic acid level, and is encoded by a variegated gene library. For instance, a mixture of synthetic oligonucleotides can be enzymatically ligated into gene sequences such that the degenerate set of potential Elf-1 sequences are expressible as individual polypeptides, or alternatively, as a set of larger fusion proteins (e.g. for phage display) containing the set of Elf-1 sequences therein.

As illustrated in FIG. 4, to analyze the sequences of a population of variants, the amino acid sequences of interest can be aligned relative to sequence homology. The presence or absence of amino acids from an aligned sequence of a particular variant is relative to a chosen consensus length of a reference sequence, which can be real or artificial. In order to maintain the highest homology in alignment of sequences, deletions in the sequence of a variant relative to the reference sequence can be represented by an amino acid space (*), while insertional mutations in the variant relative to the reference sequence can be disregarded and left out of the sequence of the variant when aligned. For instance, FIG. 4 includes the alignment of several cloned forms of Elf-1 from different species, e.g., a murine Elf-1 (muElf-1) and a chicken Elf-1 (chElf-1 ). Analysis of the alignment of the Elf-1 clones shown in FIG. 4 can give rise to the generation of a degenerate library of polypeptides comprising potential Elf-1 sequences.

In an illustrative embodiment, alignment of the muElf-1 and chElf-1 clones can produce a degenerate set of Elf-1 polypeptides represented by the general formula:

D-R-Y-X (1) -V-Y-W-N-R-S-N-P-R-F-X (2) -X (3) -X (4) -X (5) -X (6) -G-D-X (7) -X (8) -X (9) -Y-T-V-E-V-S-I-N-D-Y-L-D-I-Y-C-P-H-Y-X (10) -X (11) -P-L-P-X (12) -A-E-R-M-E-R-Y-X (13) -L-Y-M-V-N-X (14) -E-G-H-A-S-C-D-H-R-Q-X (15) -G-F-K-R-W-E-C-N-R-P-X (16) -X (17) -P-X (18) -G-P-L-K-F-S-E-K-F-Q-L-F-T-P-F-S-L-G-F-E-F-R-P-G-H-E-Y-Y-Y-I-S-A-X (19) -P-P-N-X (20) -V-D-R-P-C-L-X (21) -L-K-V-Y-V-R-P-T-N-X (22) -X (23) -L-Y-E-X (24) -P-E-P-I-F-T-S-N-X (25) -S-C-X (26) -X (27)-L-X (28) -X (29) -X (30) -X (31) -X (32) -X (33) -L-X (34) -X (35) -X (36) -P-V-X (37)-W-X (38) -L-L-G-S (SEQ ID NO: 5), wherein each of the degenerate positions "X" can be an amino acid which occurs in that position in one of the mouse or chicken Elf-1 clones, or, to expand the library, each X can also be selected from amongst amino acid residue which would be conservative substitutions for the amino acids which appear naturally in each of those positions. For instance, Xaa(1) represents Gly, Ala, Val, Leu, Ile, Ser or Thr; Xaa(2) represents Arg, His, Lys, Asn or Gln; Xaa(3) represents Gly, Ala, Val, Leu, Ile, Ser, Thr, Arg, Lys or His; Xaa(4) represents Gly, Ala, Val, Leu, Ile, Ser, Thr or an amino acid gap; Xaa(5) represents Gly, Ala, Val, Leu, Ile, Ser, Thr or an amino acid gap; Xaa(6) represents Gly, Ala, Val, Leu, Ile, Ser, Thr or an amino acid gap; Xaa(7) represents Gly, Ala, Val, Leu, Ile, Ser, Thr, Pro or an amino acid gap; Xaa(8) represents Gly, Ala, Val, Leu, Ile, Ser, Thr, Pro or an amino acid gap; Xaa(9) represents Gly, Ala, Val, Leu, Ile, Ser, Thr, Pro or an amino acid gap; Xaa(10 ) represents Gly, Ala, Val, Lcu, Ile, Ser, Thr, Asp or Glu;

Xaa(11) represents Gly, Ala, Val, Leu, Ile, Ser, Thr, Asp or Glu; Xaa(12) represents Gly, Ala, Val, Leu, Ile, Ser, Thr, Pro or an amino acid gap; Xaa(13) represents Gly, Ala, Val, Leu, Ile, Ser or Thr; Xaa(14) represents Gly, Ala, Val, Leu, lie, Ser, Thr, Phe, Tyr or Trp; Xaa(15) represents Arg, Lys or His; Xaa(16) represents Gly, Ala, Val, Leu, Ile, Ser, Thr, Asp or Glu; Xaa(17) represents Gly, Ala, Val, Leu, Ile, Ser or Thr; Xaa(18) represents Gly, Ala, Val, Leu, Ile, Ser or Thr; Xaa(19) represents Gly, Ala, Val, Leu, lie, Ser or Thr; Xaa(20) represents Gly, Ala, Val, Leu, Ile, Ser or Thr; Xaa(21) represents Arg, Lys or His; Xaa(22) represents Asp or Glu; Xaa(23) represents Gly, Ala, Val, Leu, Ile, Ser or Thr; Xaa(24) represents Gly, Ala, Val, Leu, Ile, Ser or Thr; Xaa(25) represents Gly, Ala, Val, Leu, Ile, Ser, Thr, Asn or Gln; Xaa(26) represents Gly, Ala, Val, Leu, Ile, Ser, Thr, Cys or Met; Xaa(27) represents Gly, Ala, Val, Leu, Ile, Ser or Thr; Xaa(28) represents Gly, Ala, Val, Leu, Ile, Ser or Thr; Xaa(29) represents Gly, Ala, Val, Leu, Ile, Ser or Thr; Xaa(30) represents Gly, Ala, Val, Leu, Ile, Ser, Thr, Pro, Cys, Met or an amino acid gap; Xaa(31) represents Arg, Lys or His; Xaa(32) represents Gly, Ala, Val, Leu, Ile, Ser or Thr; Xaa(33) represents Gly, Ala, Val, Leu, Ile, Ser, Thr, Phe, Tyr or Trp; Xaa(34) represents Gly, Ala, Val, Leu, Ile, Ser or Thr, Xaa(35) represents Gly, Ala, Val, Leu, Ile, Ser or Thr; Xaa(36) represents Gly, Ala, Val, Leu, Ile, Ser or Thr; Xaa(37) represents Gly, Ala, Val, Leu, Ile, Ser, Thr, Phe, Tyr or Trp; Xaa(38) represents Gly, Ala, Val, Leu, Ile, Ser or Thr. In an even more expansive library, each X can be selected from any amino acid residue type.

There are many ways by which the library of potential Elf-1 homologs can be generated from a degenerate oligonucleotide sequence. Chemical synthesis of a degenerate gene sequence can be carried out in an automatic DNA synthesizer, and the synthetic genes then ligated into an appropriate expression vector. The purpose of a degenerate set of genes is to provide, in one mixture, all of the sequences encoding the desired set of potential Elf-1 sequences. The synthesis of degenerate oligonucleotides is well known in the art (see for example, Narang, SA (1983) *Tetrahedron* 39:3; Itakura et al. (1981) *Recombinant DNA, Proc* 3*rd Cleveland Sympos. Macromolecules,* ed. AG Walton, Amsterdam: Elsevier pp273–289; Itakura et al. (1984) *Annu. Rev. Biochem.* 53:323; Itakura et al. (1984) *Science* 198:1056; Ike et al. (1983) *Nucleic Acid Res.* 11:477. Such techniques have been employed in the directed evolution of other proteins (see, for example, Scott et al. (1990) *Science* 249:386–390; Roberts et al. (1992) *PNAS* 89:2429–2433; Devlin et al. (1990) *Science* 249: 404–406; Cwirla et al. (1990) *PNAS* 87: 6378–6382; as well as U.S. Pat. Nos. 5,223,409, 5,198,346, and 5,096,815).

Alternatives to the above combinatorial mutagenesis also exist. For example, Elf-1 homologs (both agonist and antagonist forms) can be generated and isolated from a library by screening using, for example, alanine scanning mutagenesis and the like (Ruf et al. (1994) *Biochemistry* 33:1565–1572; Wang et al. (1994) *J. Biol. Chem.* 269:3095–3099; Balint et al. (1993) *Gene* 137:109–118; Grodberg et al. (1993) *Eur. J. Biochem.* 218:597–601; Nagashima et al. (1993) *J. Biol. Chem.* 268:2888–2892; Lowman et al. (1991) Biochemistry 30:10832–10838; and Cunningham et al. (1989) *Science* 244:1081–1085), by linker scanning mutagenesis (Gustin et al. (1993) *Virology* 193:653–660; Brown ct al. (1992) *Mol. Cell Biol.* 12:2644–2652; McKnight et al. (1982) *Science* 232:316); by saturation mutagenesis (Meyers et al. (1986) *Science* 232:613); by PCR mutagenesis (Leung et al. (1989) *Method Cell Mol Biol* 1:11–19); or by random mutagenesis (Miller et al. (1992) *A Short Course in Bacterial Genetics,* CSHL Press, Cold Spring Harbor, N.Y.; and Greener et al. (1994) *Strategies in Mol Biol* 7:32–34).

A wide range of techniques are known in the art for screening gene products of combinatorial libraries, and for screening cDNA libraries for gene products having a certain property. Such techniques will be generally adaptable for rapid screening of the gene libraries generated by the combinatorial mutagenesis of Elf-1 homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate Elf-1 sequences created by combinatorial mutagenesis techniques.

In one screening assay, the candidate Elf-1 polypeptides are displayed on the surface of a cell or viral particle, and the ability of particular cells or viral particles to bind an EPH receptor protein via this gene product is detected in a "panning assay". For instance, the gene library can be cloned into the gene for a surface membrane protein of a bacterial cell, and the resulting fusion protein detected by panning (Ladner et al., WO 88/06630; Fuchs et al. (1991) *Bio/Technology* 9:1370–1371; and Goward et al. (1992) *TIBS* 18:136–140). In a similar fashion, a detectably labeled EPH receptor can be used to score for potentially functional Elf-1 polypeptide homologs. For example, the AP-mek4 or Ap-sek fusion proteins described below, or the equivalent fluorescently labeled receptors, can be used to detect Elf-1 homolog which retain receptor-binding activity. In the application of fluorescently labeled receptor, cells can be visually inspected and separated under a fluorescence microscope, or, where the morphology of the cell permits, separated by a fluorescence-activated cell sorter.

In an alternate embodiment, the gene library is expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at very high concentrations, a large number of phage can be screened at one time. Second, since each infectious phage displays the combinatorial gene product on its surface, if a particular phage is recovered from an affinity matrix in low yield, the phage can be amplified by another round of infection. The group of almost identical *E. coli* filamentous phages M13, fd., and fl are most often used in phage display libraries, as either of the phage gIII or gVIII coat proteins can be used to generate fusion proteins without disrupting the ultimate packaging of the viral particle (Ladner et al. PCT publication WO 90/02909; Garrard et al., PCT publication WO 92/09690; Marks et al. (1992) *J. Biol. Chem.* 267:16007–16010; Griffiths et al. (1993) *EMBO J* 12:725–734; Clackson et al. (1991) *Nature* 352:624–628; and Barbas et al. (1992) *PNAS* 89:4457–4461).

In an illustrative embodiment, the recombinant phage antibody system (RPAS, Pharamacia Catalog number 27–9400–01) can be easily modified for use in expressing and screening Elf-1 combinatorial libraries. For instance, the pCANTAB 5 phagemid of the RPAS kit contains the gene which encodes the phage gIII coat protein. The Elf-1 combinatorial gene library, such as which may encode the $Cys_4$ motifs of the degenerate Elf-1 library described above, can be cloned into the phagemid adjacent to the gIII signal sequence such that it will be expressed as a gIII fusion protein. After ligation, the phagemid is used to transform competent E. coli TG1 cells. Transformed cells are subsequently infected with M13KO7 helper phage to rescue the phagemid and its candidate Elf-1 gene insert. The resulting recombinant phage contain phagemid DNA encoding a specific candidate Elf-1, and display one or more copies of the corresponding fusion coat protein. The phage-displayed candidate Elf-1 proteins which are capable of binding an Elf-1 receptor are selected or enriched by panning. For instance, the phage library can be on glutathione-immobilized EPH receptor/GST fusion proteins to enrich for Elf-1 homologs which retain an ability to bind an EPH receptor. The bound phage is then isolated, and if the recombinant phage express at least one copy of the wild type gill coat protein, they will retain their ability to infect E. coli. Thus, successive rounds of reinfection of E. coli, and panning will greatly enrich for Elf-1 homologs.

Each of these homologs can subsequently be screened for further biological activities in order to differentiate agonists and antagonists. For example, receptor-binding homologs isolated from the combinatorial library can be tested for their effect on cellular proliferation relative to the wild-type form of the protein. Alternatively, one could screen the homologs for agonists by detecting autophosphorylation of an EPH receptor in response to treatment with the homolog (see, for example, Millauer et al. (1993) *Cell* 72:835–846). In similar fashion, antagonists can be identified from the enriched fraction based on their ability to inhibit autophosphorylation of the receptor by wild-type Elf-1 protein.

In another embodiment, the combinatorial library is designed to be extracellularly presented (e.g. as it occurs naturally) and, though optionally, secreted (e.g. the polypeptides of the library all include a signal sequence but no phosphatidylinositol linkage). The gene can be used to transfect a eukaryotic cell that can be co-cultured with cells which express an functional EPH receptor, e.g. a hek-related receptor, and which are sensitive to treatment with the wild-type soluble form of Elf-1. Functional Elf-1 homologs secreted by the cells expressing the combinatorial library will diffuse to neighboring EPH+cells and induce a phenotypic change. Using, for example, antibodies directed to epitopes which are either created or destroyed in response to Elf-1 treatment, the pattern of detection of Elf-1 induction will resemble a gradient function, and will allow the isolation (generally after several repetitive rounds of selection) of cells producing active Elf-1 homologs. Likewise, Elf-1 antagonists can be selected in similar fashion by the ability of the cell producing a functional antagonist to protect neighboring cells from the effect of authentic Elf-1 added to the culture media.

To illustrate, target cells are cultured in 24-well microtitre plates. The target cells can be, for instance, cells which naturally express hek-related or sek-related receptors, such as NIH 3T3 cells, or cells which have been transfected with genes encoding such a receptor. COS cells are transfected with the combinatorial Elf-1 gene library and cultured (optionally) in a cell culture insert (e.g. Collaborative Biomedical Products, Catalog #40446) that are able to fit into the wells of the microtitre plate. The cell culture inserts are placed in the wells such that recombinant Elf-1 homologs secreted by the cells in the insert can diffuse through the porous bottom of the insert and contact the target cells in the microtitre plate wells. After a period of time sufficient for functional forms of Elf-1 to produce a measurable response in the target cells, the inserts are removed and the effect of any Elf-1 homologs on the target cells determined. Cells from the inserts corresponding to wells which score positive for activity can be split and re-cultured on several inserts, the process being repeated until the active clones are identified.

The invention also provides for reduction of the Elf-1 polypeptides to generate mimetics, e.g. peptide or non-peptide agents, which are able to disrupt binding of an Elf-1 polypeptide of the present invention with an EPH receptor. Accordingly, such mutagenic techniques as described above are also useful to map the determinants of the Elf-1 polypeptides which participate in protein-protein interactions involved in, for example, binding of the subject Elf-1 polypeptide to an EPH receptor or in causing oligomerization of receptors. To illustrate, the critical residues of a subject Elf-1 polypeptide which are involved in molecular recognition of an EPH receptor can be determined and used to generate Elf-1 polypeptide-derived peptidomimietics which competitively inhibit binding of the authentic Elf-1 protein with that receptor. By employing, for example, scanning mutagenesis to map the amino acid residues of the Elf-1 protein involved in binding the mek4 receptor, peptidomimetic compounds can be generated which mimic those residues in binding to the receptor and which consequently can inhibit binding of Elf-1 to the mek4 receptor and interfere with the function of the mek4 receptor. For instance, non-hydrolyzable peptide analogs of such residues can be generated using benzodiazepine (e.g., see Freidinger et al. in *Peptides: Chemistry and Biology,* G.R. Marshall ed., ESCOM Publisher: Leiden, Netherlands, 1988), azepine (e.g., see Huffman et al. in *Peptides: Chemistry and Biology,* G.R. Marshall ed., ESCOM Publisher: Leiden, Netherlands, 1988), substituted gama lactarn rings (Garvey et al. in *Peptides: Chemistry and Biology,* G.R. Marshall ed., ESCOM Publisher: Leiden, Netherlands, 1988), keto-methylene pseudopeptides (Ewenson et al. (1986) *J Med Chem* 29:295; and Ewenson et al. in *Peptides: Structure and Function* (Proceedings of the 9th American Peptide Symposium) Pierce Chemical Co. Rockland, Ill., 1985), β-turn dipeptide cores (Nagai et al. (1985) *Tetrahedron Lett* 26:647; and Sato et al. (1986) *J Chem Soc Perkin Trans* 1:1231), and β-aminoalcohols (Gordon et al. (1985) *Biochem Biophys Res Commun* 126:419; and Dann et al. (1986) *Biochem Biophys Res Commun* 134:71).

Another aspect of the invention pertains to an antibody specifically reactive with an Elf-1 protein. For example, by using immunogens derived from an Elf-1 protein, e.g. based on the cDNA sequences, anti-protein/anti-peptide antisera or monoclonal antibodies can be made by standard protocols (See, for example, *Antibodies: A Laboratory Manual* ed. by Harlow and Lane (Cold Spring Harbor Press: 1988)). A mammal, such as a mouse, a hamster or rabbit can be immunized with an immunogenic form of the peptide (e.g., an Elf-1 polypeptide or an antigenic fragment which is capable of eliciting an antibody response). Techniques for conferring immunogenicity on a protein or peptide include conjugation to carriers or other techniques well known in the art. An immunogenic portion of the Elf-1 protein can be administered in the presence of adjuvant. The progress of immunization can be monitored by detection of antibody titers in plasma or serum. Standard ELISA or other immunoassays can be used with the immunogen as antigen to assess the levels of antibodies. In a preferred embodiment, the subject antibodies are immunospecific for antigenic determinants of the Elf-1 protein of the present invention, e.g. antigenic determinants of a protein represented by SEQ ID No: 2 and/or SEQ ID No: 4, or a closely related human or non-human mammalian homolog (e.g. atleast 85 percent homologous, preferably atleast 90 percent homologous, and more preferably at least 95 percent homologous). In yet a further preferred embodiment of the present invention, the anti-Elf-1 polypeptide antibodies do not substantially cross react (i.e. does not react specifically) with a protein which is, for example, less than 85 percent homologous to SEQ ID No: 2; e.g. less than 95 percent homologous with one of SEQ ID No: 2; e.g. less than 98–99 percent homologous with one of SEQ ID No: 2; less than 85 percent homologous to SEQ ID No: 4; e.g. less than 95 percent homologous with one of SEQ ID No: 4; e.g. less than 98–99 percent homologous with one of SEQ ID No: 4. By "not substantially cross react", it is meant that the antibody has a binding affinity for a non-homologous protein (e.g. LERK or the B61 proteins) which is at least one order of magnitude, more preferably at least 2 orders of magnitude, and even more preferably at least 3 orders of magnitude less than the binding affinity of the antibody for the protein of SEQ ID No: 2 or SEQ ID No: 4.

Following immunization, anti-Elf-1 antisera can be obtained and, if desired, polyclonal anti-Elf-1 antibodies isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, an include, for example, the hybridoma technique (originally developed by Kohler and Milstein, (1975) *Nature*, 256: 495–497), the human B cell hybridoma technique (Kozbar et al., (1983) *Immunology Today*, 4: 72), and the EBV-hybridoma technique to produce human monoclonal antibodies (Cole et al., (1985) *Monoclonal Antibodies and Cancer Therapy*, Alan R. Liss, Inc. pp. 77–96). Hybridoma cells can be screened immunochemically for production of antibodies specifically reactive with an Elf-1 polypeptide of the present invention and monoclonal antibodies isolated from a culture comprising such hybridoma cells.

The term antibody as used herein is intended to include fragments thereof which are also specifically reactive with one of the subject Elf-1 polypeptide. Antibodies can be fragmented using conventional techniques and the fragments screened for utility in the same manner as described above for whole antibodies. For example, F(ab)$_2$ fragments can be generated by treating antibody with pepsin. The resulting F(ab)$_2$ fragment can be treated to reduce disulfide bridges to produce Fab fragments. The antibody of the present invention is further intended to include single chain, bispecific and chimeric molecules having an Elf-1 affinity conferred by at least one CDR region of the antibody.

Both monoclonal and polyclonal antibodies (Ab) directed against Elf-1 polypeptide or Elf-1 polypeptide variants, and antibody fragments such as Fab and F(ab)$_2$ can be used to block the action of Elf-1 and allow the study of the role of Elf-1 in, for example, embryogenesis and/or tumorogenesis. For example, purified monoclonal Abs can be injected directly into the limb buds of chick or mouse embryos. It is demonstrated in the examples below that Elf-1 is expressed in the limb buds of day 10.5 embryos. Thus, the use of anti-Elf-1 Abs during this developmental stage can allow assessment of the effect of Elf-1 on the formation of limbs in vivo. In a similar approach, hybridomas producing anti-Elf-1 monoclonal Abs, or biodegradable gels in which anti-Elf-1 Abs are suspended, can be implanted at a site proximal or within the area at which Elf-1 action is intended to be blocked. Experiments of this nature can aid in deciphering the role of this and other factors that may be involved in limb patterning and tissue formation.

Antibodies which specifically bind Elf-1 polypeptide epitopes can also be used in immunohistochemical staining of tissue samples in order to evaluate the abundance and pattern of expression of each of the subject Elf-1 polypeptides. Anti-Elf-1 antibodies can be used diagnostically in immuno-precipitation and immuno-blotting to detect and evaluate Elf-1 protein levels in tissue or bodily fluid as part of a clinical testing procedure. For instance, such measurements can be useful in predictive valuations of the onset or progression of neurological disorders, such as those marked by denervation-like or disuse-like symptoms. Likewise, the ability to monitor Elf-1 levels in an individual can allow determination of the efficacy of a given treatment regimen for an individual afflicted with such a disorder. The level of Elf-1 polypeptides can be measured in bodily fluid, such as in samples of cerebral spinal fluid, or can be measured in tissue, such as produced by biopsy. Diagnostic assays using anti-Elf-1 antibodies can include, for example, immunoassays designed to aid in early diagnosis of a neurodegenerative disorder, particularly ones which are manifest at birth. Diagnostic assays using anti-Elf-1 polypeptide antibodies can also include immunoassays designed to aid in early diagnosis and phenotyping of a neoplastic or hyperplastic disorder.

Another application of anti-Elf-1 antibodies of the present invention is in the immunological screening of cDNA libraries constructed in expression vectors such as λgt11, λgt8–23, λZAP, and λORF8. Messenger libraries of this type, having coding sequences inserted in the correct reading frame and orientation, can produce fusion proteins. For instance, λgt11 will produce fusion proteins whose amino termini consist of β-galactosidase amino acid sequences and whose carboxy termini consist of a foreign polypeptide. Antigenic epitopes of an Elf-1 protein can then be detected with antibodies, as, for example, reacting nitrocellulose filters lifted from infected plates with anti-Elf-1 antibodies. Positive phage detected by this assay can then be isolated from the infected plate. Thus, the presence of Elf-1 homologs (orthologs) can be detected and cloned from other animals, as can alternate isoforms (including splicing variants).

Moreover, the nucleotide sequence determined from the cloning of the Elf-1 gene will further allow for the generation of probes and primers designed for use in identifying and/or cloning Elf-1 homologs in other cell types, e.g. from other tissues, as well as Elf-1 homologs from other animals, e.g. humans. For instance, the present invention also provides a probe/primer comprising a substantially purified oligonucleotide, which oligonucleotide comprises a region of nucleotide sequence that hybridizes under stringent conditions to at least 10 consecutive nucleotides of sense or anti-sense sequence of SEQ ID No: 1 and/or SEQ ID No: 3, or naturally occurring mutants thereof For instance, primers based on the nucleic acids represented in SEQ ID No. 1 or 3 can be used in PCR reactions to clone Elf-1 homologs. Likewise, probes based on the Elf-1 gene sequences of SEQ ID No. 1 and 3 can be used to detect Elf-1 transcripts or genomic sequences. In preferred embodiments, the probe further comprises a label group attached thereto and able to be detected, e.g. the label group is selected from the group consisting of radioisotopes, fluorescent compounds, enzymes, and enzyme co-factors. Such probes can also be used as a part of a diagnostic test kit for identifying cells in which Elf-1 is misexpressed, such as by measuring a level of an Elf-1 encoding nucleic acid in a sample of cells from a patient; e.g. detecting Elf-1 mRNA levels or determining whether a genomic Elf-1 gene has been mutated or deleted.

To illustrate, nucleotide probes can be generated from the Elf-1 gene which facilitate histological screening of intact tissue and tissue samples for the presence of an Elf-1 polypeptide mRNA. Similar to the diagnostic uses of anti-Elf-1 polypeptide antibodies, the use of probes directed to Elf-1 messages, or to genomic Elf-1 sequences, can be used for both predictive and therapeutic evaluation of allelic mutations which might be manifest in, for example, neoplastic or hyperplastic disorders (e.g. unwanted cell growth) or abnormal differentiation of tissue. Used in conjunction with anti-Elf-1 immunoassays, the nucleotide probes can help facilitate the determination of the molecular basis for a developmental disorder which may involve some abnormality associated with expression (or lack thereof) of an Elf-1 polypeptide. For instance, variation in Elf-1 polypeptide synthesis can be differentiated from a mutation in the Elf-1 coding sequence.

Accordingly, the present method provides a method for determining if a subject is at risk for a disorder characterized by unwanted cell proliferation or abherent control of differentiation. In preferred embodiments, the subject method can be generally characterized as comprising detecting, in a tissue sample of the subject (e.g. a human patient), the presence or absence of a genetic lesion characterized by at least one of (i) a mutation of a gene encoding an Elf-1 polypeptide or (ii) the mis-expression of an Elf-1 gene. To illustrate, such genetic lesions can be detected by ascertaining the existence of at least one of (i) a deletion of one or more nucleotides from an Elf-1 gene, (ii) an addition of one or more nucleotides to such an Elf-1 gene, (iii) a substitution of one or more nucleotides of an Elf-1 gene, (iv) a gross chromosomal rearrangement of an Elf-1 genes, (v) a gross alteration in the level of a messenger RNA transcript of an Elf-1 gene, (vi) the presence of a non-wild type splicing pattern of a messenger RNA transcript of an Elf-1 gene, and (vii) a non-wild type level of an Elf-1 polypeptide. In one aspect of the invention there is provided a probe/primer comprising an oligonucleotide containing a region of nucleotide sequence which is capable of hybridizing to a sense or antisense sequence of SEQ ID No: 1 and/or SEQ ID No: 3, or naturally occurring mutants thereof, or 5' or 3' flanking sequences or intronic sequences naturally associated with an Elf-1 gene. The probe is exposed to nucleic acid of a tissue sample; and the hybridization of the probe to the sample nucleic acid is detected. In certain embodiments, detection of the lesion comprises utilizing the probe/primer in a polymerase chain reaction (PCR) (see, e.g., U.S. Pat. Nos: 4,683,195 and 4,683,202) or, alternatively, in a ligation chain reaction (LCR) (see, e.g., Landegran et al. (1988) Science, 241:1077–1080; and NaKazawa et al. (1944) PNAS 91:360–364) the later of which can be particularly useful for detecting point mutations in the Elf-1 gene. Alternatively, immunoassays can be employed to determine the level of Elf-1 protein, either soluble or membrane bound.

Also, the use of anti-sense techniques (e.g. microinjection of antisense molecules, or transfection with plasmids whose transcripts are anti-sense with regard to an Elf-1 mRNA or gene sequence) can be used to investigate role of Elf-1 in developmental events, as well as the normal cellular function of Elf-1 in adult tissue. Such techniques can be utilized in cell culture, but can also be used in the creation of transgenic animals.

Furthermore, by making available purified and recombinant Elf-1 polypeptides, the present invention facilitates the development of assays which can be used to screen for drugs, or for Elf-1 homologs, which are either agonists or antagonists of the normal cellular function of the subject Elf-1 polypeptides, or of their role in the pathogenesis of cellular proliferation and/or differentiation and disorders related thereto. In one embodiment, the assay evaluates the ability of a compound to modulate binding between an Elf-1 polypeptide and an EPH receptor. A variety of assay formats will suffice and, in light of the present inventions, will be comprehended by skilled artisan.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with receptor proteins. Accordingly, in an exemplary screening assay of the present invention, the compound of interest is contacted with an EPH receptor polypeptide which is ordinarily capable of binding an Elf-1 protein. To the mixture of the compound and receptor is then added a composition containing a Elf-1 polypeptide. Detection and quantification of receptor/Elf-1 complexes provides a means for determining the compound's efficacy at inhibiting (or potentiating) complex formation between the receptor protein and the Elf-1 polypeptide. The efficacy of the compound can be assessed by generating dose response curves from data obtained using various concentrations of the test compound. Moreover, a control assay can also be performed to provide a baseline for comparison. In the control assay, isolated and purified Elf-1 polypeptide is added to a composition containing the receptor protein, and the formation of receptor/Elf-1 complex is quantitated in the absence of the test compound.

Complex formation between the Elf-1 polypeptide and an EPH receptor may be detected by a variety of techniques. For instance, modulation of the formation of complexes can be quantitated using, for example, detectably labelled proteins such as radiolabelled, fluorescently labelled, or enzymatically labelled Elf-1 polypeptides, by immunoassay, or by chromatographic detection.

Typically, it will be desirable to immobilize either the EPH receptor or the Elf-1 polypeptide to facilitate separation of receptor/Elf-1 complexes from uncomplexed forms of one of the proteins, as well as to accomadate automation of the assay. In one embodiment, a fusion protein can be provided which adds a domain that allows the protein to be bound to a matrix. For example, glutathione-S-transferase/receptor (GST/receptor) fusion proteins can be adsorbed onto glutathione sepharose beads (Sigma Chemical, St. Louis, Mo.) or glutathione derivatized microtitre plates, which are then combined with the Elf-1 polypeptide, e.g. an $^{35}$S-labeled Elf-1 polypeptide, and the test compound and incubated under conditions conducive to complex formation, e.g. at physiological conditions for salt and pH, though slightly more stringent conditions may be desired, e.g., at 4° C. in a buffer containing 0.6M NaCl or a detergent such as 0.1% Triton X-100. Following incubation, the beads are washed to remove any unbound Elf-1 polypeptide, and the matrix bead-bound radiolabel determined directly (e.g.

beads placed in scintilant), or in the superntantant after the receptor/Elf-1 complexes are dissociated. Alternatively, the complexes can dissociated from the bead, separated by SDS-PAGE gel, and the level of Elf-1 polypeptide found in the bead fraction quantitated from the gel using standard electrophoretic techniques.

Other techniques for immobilizing proteins on matrices are also available for use in the subject assay. For instance, the EPH receptor protein can be immobilized utilizing conjugation of biotin and streptavidin. For instance, biotinylated receptor molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with the EPH receptor but which do not interfere with Elf-1 binding can be derivatized to the wells of the plate, and the receptor trapped in the wells by antibody conjugation. As above, preparations of an Elf-1 polypeptide and a test compound are incubated in the receptor-presenting wells of the plate, and the amount of receptor/Elf-1 complex trapped in the well can be quantitated. Exemplary methods for detecting such complexes, in addition to those described above for the GST-immobilized complexes, include immunodetection of complexes using antibodies reactive with the Elf-1 polypeptide, or which are reactive with the receptor protein and compete for binding with the Elf-1 polypeptide; as well as enzyme-linked assays which rely on detecting an enzymatic activity associated with the Elf-1 polypeptide. In the instance of the latter, the enzyme can be chemically conjugated or provided as a fusion protein with the Elf-1 polypeptide. To illustrate, the Elf-1 polypeptide can be chemically cross-linked or genetically fused with alkaline phosphatase, and the amount of Elf-1 polypeptide trapped in the complex can be assessed with a chromogenic substrate of the enzyme, e.g. paranitrophenylphosphate. Likewise, a fusion protein comprising the Elf-1 polypeptide and glutathione-S-transferase can be provided, and complex formation quantitated by detecting the GST activity using 1-chloro-2,4-dinitrobenzene (Habig et al (1974) *J Biol Chem* 249:7130).

For processes which rely on immunodetection for quantitating one of the proteins trapped in the complex, antibodies against the protein, such as the anti-Elf-1 antibodies described herein, can be used. Alternatively, the protein to be detected in the complex can be "epitope tagged" in the form of a fusion protein which includes, in addition to the Elf-1 polypeptide or EPH receptor sequence, a second polypeptide for which antibodies are readily available (e.g. from commercial sources). For instance, the GST fusion proteins described above can also be used for quantification of binding using antibodies against the GST moiety. Other useful epitope tags include myc-epitopes (e.g., see Ellison et al. (1991) *J Biol Chem* 266:21150–21157) which includes a 10-residue sequence from c-myc, as well as the pFLAG system (International Biotechnologies, Inc.) or the pEZZ-protein A system (Pharamacia, N.J.).

Another aspect of the present invention relates to a method of inducing and/or maintaining a differentiated state, enhancing survival, and/or promoting proliferation of a cell responsive to an Elf-1 protein, by contacting the cells with an Elf-1 agonist or an Elf-1 antagonist. For instance, it is contemplated by the invention that, in light of the present finding of an apparently broad involvement of Elf-1 proteins in the formation of ordered spatial arrangements of differentiated tissues in vertebrates, the subject method could be used to generate and/or maintain an array of different vertebrate tissue both in vitro and in vivo. The Elf-1 agent can be, as appropriate, any of the preparations described above, including isolated polypeptides, gene therapy constructs, antisense molecules, peptidomimetics or agents identified in the drug assays provided herein.

For example, the present method is applicable to cell culture technique. In vitro neuronal culture systems have proved to be fundamental and indispensable tools for the study of neural development, as well as the identification of neurotrophic factors such as nerve growth factor (NGF), ciliary trophic factors (CNTF), and brain derived neurotrophic factor (BDNF). Once a neuronal cell has become terminally-differentiated it typically will not change to another terminally differentiated cell-type. However, neuronal cells can nevertheless readily lose their differentiated state. This is commonly observed when they are grown in culture from adult tissue, and when they form a blastema during regeneration. The present method provides a means for ensuring an adequately restrictive environment in order to maintain neuronal cells at various stages of differentiation, and can be employed, for instance, in cell cultures designed to test the specific activities of other trophic factors. In such embodiments of the subject method, the cultured cells can be contacted with an Elf-1 polypeptide, or an agent identifed in the assays described above, in order to induce neuronal differentiation (e.g. of a stem cell), or to maintain the integrity of a culture of terminally-differentiated neuronal cells by preventing loss of differentiation. The source of Elf-1 in the culture can be derived from, for example, a purified or semi-purified protein composition added directly to the cell culture media, or alternatively, released from a polymeric device which supports the growth of various neuronal cells and which has been doped with a Elf-1 protein. The source of the Elf-1 can also be a cell that is co-cultured with the intended neuronal cell and which produces either a recombinant or natural form of an Elf-1 protein. Alternatively, the source can be the neuronal cell itself which as been engineered to produce a recombinant Elf-1. In an exemplary embodiment, a naive neuronal cell (e.g. a stem cell) is treated with a Elf-1 agonist in order to induce differentiation of the cells into, for example, sensory neurons or, alternatively, motorneurons. Such neuronal cultures can be used as convenient assay systems as well as sources of implantable cells for therapeutic treatments. For example, Elf-1 polypeptides may be useful in establishing and maintaining the olfactory neuron cultures described U.S. Pat. No. 5,318,907 and the like.

To further illustrate potential uses, it is noted that intracerebral grafting has emerged as an additional approach to central nervous system therapies. For example, one approach to repairing damaged brain tissues involves the transplantation of cells from fetal or neonatal animals into the adult brain (Dunnett et al. (1987) *J Exp Biol* 123:265–289; and Freund et al. (1985) *J Neurosci* 5:603–616). Fetal neurons from a variety of brain regions can be successfully incorporated into the adult brain, and such grafts can alleviate behavioral defects. For example, movement disorder induced by lesions of dopaminergic projections to the basal ganglia can be prevented by grafts of embryonic dopaminergic neurons. Complex cognitive functions that are impaired after lesions of the neocortex can also be partially restored by grafts of embryonic cortical cells. Thus, use of the present EPH receptor ligands for maintenance of neuronal cell cultures can help to provide a source of implantable neuronal tissue. The use of an Elf-1 polypeptide in the culture can be to prevent loss of differentiation, or where fetal tissue is used, especially neuronal stem cells, an Elf-1 polypeptide can be used to induce differentiation.

Stem cells useful in the present invention are generally known. For example, several neural crest cells have been identified, some of which are multipotent and likely represent uncommitted neural crest cells, and others of which can generate only one type of cell, such as sensory neurons, and likely represent committed progenitor cells. The role of an Elf-1 protein employed in the present method to culture such stem cells can be to induce differentiation of the uncommitted progenitor and thereby give rise to a committed progenitor cell, or to cause further restriction of the developmental fate of a committed progenitor cell towards becoming a terminally-differentiated neuronal cell. For example, the present method can be used in vitro to induce and/or maintain the differentiation of neural crest cells into glial cells, schwann cells, chromaffin cells, cholinergic sympathetic or parasympathetic neurons, as well as peptidergic and serotonergic neurons. The Elf-1 polypeptide can be used alone, or can be used in combination with other neurotrophic factors which act to more particularly enhance a particular differentiation fate of the neuronal progenitor cell. In the later instance, the Elf-1 polypeptide might be viewed as ensuring that the treated cell has achieved a particular phenotypic state such that the cell is poised along a certain developmental pathway so as to be properly induced upon contact with a secondary neurotrophic factor. In similar fashion, even relatively undifferentiated stem cells or primative neuroblasts can be maintained in culture and caused to differentiate with treatment of Elf-1 polypeptides. Exemplary primative cell cultures comprise cells harvested from the nueral plate or neural tube of an embryo even before much overt differentiation has occurred.

In addition to the implantation of cells cultured in the presence of a functional Elf-1 activity, yet another objective of the present invention concerns the therapeutic application of an Elf-1 polypeptide or mimetic to enhance survival of neurons and other neuronal cells in both the central nervous system and the peripheral nervous system. The ability of Elf-1 to regulate neuronal differentiation and survival during development of the nervous system and also presumably in the adult state indicates that Elf-1 can be reasonably expected to facilitate control of adult neurons with regard to maintenance, functional performance, and aging of normal cells; repair and regeneration processes in chemically or mechanically lesioned cells; and prevention of degeneration and premature death which result from loss of differentiation in certain pathological conditions. In light of this understanding, the present invention specifically contemplates applications of the subject proteins to the treatment of (prevention and/or reduction of the severity of) neurological conditions deriving from: (i) acute, subacute, or chronic injury to the nervous system, including traumatic injury, chemical injury, vasal injury and deficits (such as the ischemia resulting from stroke), together with infectious/inflammatory and tumor-induced injury; (ii) aging of the nervous system including Alzheimer's disease; (iii) chronic neurodegenerative diseases of the nervous system, including Parkinson's disease, Huntington's chorea, amylotrophic lateral sclerosis and the like, as well as spinocerebellar degenerations; (iv) chronic immunological diseases of the nervous system or affecting the nervous system, including multiple sclerosis; and (v) disorders of sensory neurons as well as degenerative diseases of the retina.

Many neurological disorders are associated with degeneration of discrete populations of neuronal elements and may be treatable with a therapeutic regimen which includes an Elf-1 polypeptide (or equivalent thereof). For example, Alzheimer's disease is associated with deficits in several neurotransmitter systems, both those that project to the neocortex and those that reside with the cortex. For instance, the nucleus basalis in patients with Alzheimer's disease were observed to have a profound (75%) loss of neurons compared to age-matched controls. Although Alzheimer's disease is by far the most common form of dementia, several other disorders can produce dementia. Several of these are degenerative diseases characterized by the death of neurons in various parts of the central nervous system, especially the cerebral cortex. However, some forms of dementia are associated with degeneration of the thalmus or the white matter underlying the cerebral cortex. Here, the cognitive dysfunction results from the isolation of cortical areas by the degeneration of efferents and afferents. Huntington's disease involves the degeneration of intrastraital and cortical cholinergic neurons and GABAergic neurons. Pick's disease is a severe neuronal degeneration in the neocortex of the frontal and anterior temporal lobes, sometimes accompanied by death of neurons in the striatum. Treatment of patients suffering from such degenerative conditions can include the application of Elf-1 polypeptides, or agents which mimic their effects, in order to manipulate, for example, the de-differentiation and apoptosis of neurons which give rise to loss of neurons. In preferred embodiments, a source of an Elf-1 agent is stereotactically provided within or proximate the area of degeneration.

In addition to degenerative-induced dementias, a pharmaceutical preparation of an Elf-1 homolog can be applied opportunely in the treatment of neurodegenerative disorders which have manifestations of tremors and involuntary movements. Parkinson's disease, for example, primarily affects subcortical structures and is characterized by degeneration of the nigrostriatal pathway, raphe nuclei, locus cereleus, and the motor nucleus of vagus. Ballism is typically associated with damage to the subthalmic nucleus, often due to acute vascular accident. Also included are neurogenic and myopathic diseases which ultimately affect the somatic division of the peripheral nervous system and are manifest as neuromuscular disorders. Examples include chronic atrophies such as amyotrophic lateral sclerosis, Guillain-Barre syndrome and chronic peripheral neuropathy, as well as other diseases which can be manifest as progressive bulbar palsies or spinal muscular atrophies. The present method is ammenable to the treatment of disorders of the cerebellum which result in hypotonia or ataxia, such as those lesions in the cerebellum which produce disorders in the limbs ipsilateral to the lesion. For instance, a preparation of an Elf-1 homolog can be used to treat a restricted form of cerebellar corical degeneration involving the anterior lobes (vermis and leg areas) such as is common in alcoholic patients.

In yet another embodiment, the subject method is used to treat amyotrophic lateral sclerosis. ALS is a name given to a complex of disorders that comprise upper and lower motor neurons. Patients may present with progressive spinal muscular atrophy, progressive bulbar palsy, primary lateral sclerosis, or a combination of these conditions. The major pathological adnomality is characterized by a selective and progressive degeneration of the lower motor neurons in the spinal cord and the upper motor neurons in the cerebral cortex. The therapeutic application of an Elf-1 therapeutic agent, such as a soluble form of a polypeptide represented in either of SEQ ID No: 2 or 4, or a peptidomimetic thereof, can be used alone or in conjunction with other neurotrophic factors such as CNTF, BDNF, or NGF to prevent and/or reverse motor neuron degeneration in ALS patients.

The Elf-1 polypeptides of the present invention can also be used in the treatment of autonomic disorders of the peripheral nervous system, which include disorders affecting the innervation of smooth muscle and endocrine tissue (such as glandular tissue). For instance, Elf-1 compositions may be useful to treat tachycardia or atrial cardiac arrythmias which may arise from a degenerative condition of the nerves innervating the striated muscle of the heart.

Furthermore, a potential role of Elf-1 which is apparent from the appended examples, namely the data respecting Elf-1 and its cognate receptors in retinal tissue and in the limb bud, concerns the role of Elf-1 in development and maintenance of dendritic processes of axonal neurons. In particular, as set forth in the examples below, Elf-1 is expressed in the midbrain. This region is where several different sense organs project and form a topographic representation of the outside world. For example, the retinal ganglion cells project onto the tectum (which is a part of the midbrain). Indeed, Elf-1 mRNA is expressed in the chick tectum in a gradient along the anteroposterior axis, and a gradient of ligand activity that matches the gradient of Elf-1 RNA is detectable in the tectum with soluble receptor reagents. The in situ data described below suggests that the sek and mek4 (a hek-related receptor) are expressed in the developing optic cup and possibly optic vesicle, with mek4 receptor RNA being expressed in a gradient along the nasotemporal axis in the retinal ganglion cells, where Sek is expressed uniformly. Moreover, it has been reported elsewhere that cek4 and cek8 are expressed in retinal tissue (Sajjadi et al. (1993) *Oncogene* 8:1807–1813). Accordingly, Elf-1 is therefore implicated in development of the retinotectal projection, and has properties. predicted of a molecule that may specify map topography in the projection of retinal axons onto a visual map in the tectum. Moreover, Elf-1 may further control projection of neurons from other sense organs onto the topographic maps of the brain (for review, see Holt et al. (1993) *J Neurobiol* 24:1400–1422). In addition to providing guidance for the axonal projections, Elf-1 may also promote the differentiation and/or maintenance of the innervating cells to their axonal processes.

Accordingly, compositions comprising Elf-1 homologs or other Elf-1 agents described herein may be employed to support, or alternatively, antagonize the survival and reprojection of several types of central and peripheral ganglionic neurons, sympathetic and sensory neurons, as well as motor neurons. In particular, such therapeutic compositions may be usefil in treatments designed to rescue, for example, retinal ganglia, inner ear and accoustical nerves, and motorneurons, from lesion-induced death as well as guiding reprojection of these neurons after such damage. Such diseases and conditions include but are not limited to CNS trauma, infarction, infection (such as viral infection with varicella-zoster), metabolic disease, nutritional deficiency, toxic agents (such as cisplatin treatment). Moreover, certain of the Elf-1 agents (probably antagonistic forms) may be useful in the selective ablation of sensory neurons, for example, in the treatment of chronic pain syndromes.

Elf-1 can be used in nerve prostheses for the repair of central and peripheral nerve damage. In particular, where a crushed or severed axon is entubulated by use of a prosthetic device, Elf-1 polypeptides can be added to the prosthetic device to increase the rate of growth and regeneration of the dendritic processes. Exemplary nerve guidance channels are described in U.S. Pat. Nos. 5,092,871 and 4,955,892. Accordingly, a severed axonal process can be directed toward the nerve ending from which it was severed by a prosthesis nerve guide which contains, e.g. a semi-solid formulation containing an Elf-1 polypeptide or mimetic, or which is derivatized along the inner walls with an Elf-1 protein.

Moreover, compositions of Elf-1 polypeptides may be useful in the treatment of retinal degeneration, e.g., to enhance survival and projection of retinal ganglion cells, as well as to possibly rescue retinal photoreceptor cells. Such therapeutic intervention could include administration of an Elf-1 composition alone or in conjunction with other survival/ growth factors. Corrective gene therapy with an Elf-1 gene construct described above may also be performed. Suitable implants for intraoccular delivery of Elf-1 preparations can be found in, for example, Park et al. (1993) *Int Rev Cytol* 146:49–74; Ben-Nun et al. (1989) *Aust N Z J Ophthalmol* 17:185–190; and U.S. Pat. No. 5,273,530.

In yet another embodiment, the subject Elf-1 polypeptides can be used in the treatment of neoplastic or hyperplastic transformations, particulary of the central nervous system and lymphatic system. For instance, certain Elf-1 homologs are likely to be capable of inducing differentiation of transformed neuronal cells to become post-mitotic or possibly apoptotic. Treatment with other Elf-1 homologs may involve disruption of autocrine loops, such as TGF-β or PDGF autostimulatory loops, believed to be involved in the neoplastic transformation of several neuronal tumors. Elf-1 homologs may, therefore, be of use in the treatment of, for example, malignant gliomas, medulloblastomas, neuroectodermal tumors, and ependymonas.

Likewise, the EPH receptor hek, which is the human ortholog of mek4, has been shown to be expressed on the surface of non-neuronal tumor cells, and its hyperexpression in tumor cells has been suggested to play a role in tumor induction. Accordingly, antagonist of Elf-1 (including antisense and gene therapy contructs) may be useful in the treatment of, for example, hematopoietic tumors and other tumors which express EPH receptors which bind Yet another aspect of the present invention concerns the application of the discovery that Elf-1 proteins are presumably induction signals involved in other vertebrate organogenic pathways in addition to neuronal differentiation as described above, having potential roles in other ectodermal patterning, as well as both mesodermal and endodermal differentiation processes. Thus, it is contemplated by the invention that compositions comprising Elf-1 proteins can also be utilized for both cell culture and therapeutic methods involving generation and maintenance of non-neuronal tissue, such as in controlling the development and maintenance of tissue from the digestive tract, liver, lungs, and other organs which derive from the primitive gut, as well as dorsal mesoderm-derived structures including muscular-skeletal tissues and connective tissue of the skin; intermediate mesoderm-derived structures, such as the kidney and other renal and urogenital tissues; and head mesenchymal and neural crest-derived tissue, such as cephalic connective tissue and skull and branchial cartilage, occular tissue, muscle and cardiac tissue. This should not be construed as a comprehensive list, and other tissues which may be affected by Elf-1 polypeptides are envisaged.

For example, Elf-1 polypeptides can be employed in the development and maintenance of an artificial liver which can have multiple metabolic functions of a normal liver. In an exemplary embodiment, Elf-1 agonists and/or antagonists can be used, optionally with other growth and differentiation factors, to cause differentiation of digestive tube stem cells to form hepatocyte cultures which can be used to populate extracellular matrices, or which can be encapsulated in biocompatible polymers, to form both implantable and extracorporeal artificial livers. Likewise, therapeutic compositions of certain of the subject Elf-1 polypeptides can be utilized in conjunction with transplantation of such artificial livers, as well as embryonic liver structures, to promote intraperitoneal implantation, vascularization, and in vivo differentiation and maintenance of the engrafted liver tissue, as well as to regulate such organs after physical, chemical or pathological insult.

Similarly, therapeutic compositions containing Elf-1 proteins can be used to promote regeneration of lung tissue in the treatment of emphysema and other degenerative conditions of the lung. For example, Elf-1 compositions may usefil in the treatment of degenerative disorders of lung tissue caused by, for instance, toxic injuries, as well as inflammatory and degenerative processes induced by viral infections. Tissue degeneration of the lung, and hence the therapeutic target for an Elf-1 composition, includes degenerative changes affecting the endothelial and epithelial cells, basal membrane, and mesenchymal and matrix structures.

In still another embodiment of the present invention, compositions comprising Elf-1 polypeptides of the present invention can be used in the in vitro generation of skeletal tissue such as from skeletogenic stem cells, as well as the in vivo treatment of skeletal tissue deficiencies. The present invention particularly contemplates the use of Elf-1 homologs which maintain a skeletal homeotic activity, such as an ability to induce chondrogenesis and/or osteogenesis. By "skeletal tissue deficiency", it is meant a deficiency in bone or other skeletal connective tissue at any site where it is desired to restore the bone or connective tissue, no matter how the deficiency originated, e.g. whether as a result of surgical intervention, removal of tumor, ulceration, implant, fracture, or other traumatic or degenerative conditions.

For instance, the present invention makes available effective therapeutic methods and compositions for restoring cartilage function to a connective tissue. Such Elf-1 compositions are useful in, for example, the repair of defects or lesions in cartilage tissue which is the result of degenerative wear such as that which results in arthritis, as well as other mechanical derangements which may be caused by trauma to the tissue, such as a displacement of torn meniscus tissue, meniscectomy, a Taxation of a joint by a torn ligament, malignrnent of joints, bone fracture, or by hereditary disease. The present reparative method is also useful for remodeling cartilage matrix, such as in plastic or reconstructive surgery, as well as periodontal surgery. The present method may also be applied to improving a previous reparative procedure, for example, following surgical repair of a meniscus, ligament, or cartilage. Furthermore, it may prevent the onset or exacerbation of degenerative disease if applied early enough after trauma In one embodiment of the present invention, the subject method comprises treating the afflicted connective tissue with a therapeutically sufficient amount of an Elf-1 polypeptide to generate a cartilage repair response in the connective tissue by stimulating the differentiation and/or proliferation of chondrocytes embedded in the tissue.

The present invention further contemplates the use of the subject method in the field of cartilage transplantation and prosthetic device therapies. For instance, the action of chondrogensis in the implanted tissue, as provided by the subject method, and the mechanical forces on the actively remodeling tissue can synergize to produce an improved implant more suitable for the new function to which it is to be put.

In similar fashion, the subject method can be applied to enhancing both the generation of prosthetic cartilage devices and to their implantation. The need for improved treatment has motivated research aimed at creating new cartilage that is based on collagen-glycosaminoglycan templates (Stone et al. (1990) *Clin Orthop Relat Red* 252:129), isolated chondrocytes (Grande et al. (1989) *J Orthop Res* 7:208; and Takigawa et al. (1987) *Bone Miner* 2:449), and chondrocytes attached to natural or synthetic polymers (Walitani et al. (1989) *J Bone Jt Surg* 71B:74; Vacanti et al. (1991) *Plast Reconstr Surg* 88:753; von Schroeder et al. (1991) *J Biomed Mater Res* 25:329; Freed et al. (1993) *J Biomed Mater Res* 27:11; and the Vacanti et al. U.S. Pat. No. 5,041,138). For example, chondrocytes can be grown in culture on biodegradable, biocompatible highly porous scaffolds formed from polymers such as polyglycolic acid, polylactic acid, agarose gel, or other polymers which degrade over time as function of hydrolysis of the polymer backbone into innocuous monomers. The matrices are designed to allow adequate nutrient and gas exchange to the cells until engraftment occurs. The cells can be cultured in vitro until adequate cell volume and density has developed for the cells to be implanted. One advantage of the matrices is that they can be cast or molded into a desired shape on an individual basis, so that the final product closely resembles the patient's own ear or nose (by way of example), or flexible matrices can be used which allow for manipulation at the time of implantation, as in a joint.

In one embodiment of the subject method, the implants are contacted with an Elf-1 polypeptide during the culturing process, such as an Elf-1 agonist, in order to induce and/or maintain differentiated chondrocytes in the culture so as to further stimulate cartilage matrix production within the implant. In such a manner, the cultured cells can be caused to maintain a phenotype typical of a chondrogenic cell (i.e. hypertrophic), and hence continue the population of the matrix and production of cartilage tissue.

In still further embodiments, the subject method can be employed for the generation of bone (osteogenesis) at a site in the animal where such skeletal tissue is deficient. Thus, preparations comprising Elf-1 polypeptides can be employed, for example, to induce endochondral ossification, at least so far as to facilitate the formation of cartilaginous tissue precursors to form the "model" for ossification. Therapeutic compositions of Elf-1 polypeptides can be supplemented, if required, with other osteoinductive factors, such as bone morphogenic proteins (and other TGF-β factors).

In yet another embodiment of the present invention, an Elf-1 antagonist can be used to inhibit spermatogenesis. Thus, in light of the past finding that the mek4 receptors are localized in testicular tissue, it is possible that Elf-1 proteins are involved in the differentiation and/or proliferation and maintenance of testicular germ cells. Accordingly, Elf-1 antagonist can be utilized to block the action of a naturally-occuring Elf-1 protein. In a preferred embodiment, the Elf-1 antagonist inhibits the biological activity of an authentic Elf-1 homolog in spermatogenesis by competitvely binding EPH receptors, such as mek4, in the testis. In similar fashion, Elf-1 agonists and antagonists are potentially useful for modulating normal ovarian function.

The Elf-1 polypeptides of the present invention, or pharmaceutically acceptable salts thereof, may be conveniently formulated for administration with a biologically acceptable medium, such as water, buffered saline, polyol (for example, glycerol, propylene glycol, liquid polyethylene glycol and the like) or suitable mixtures thereof. The optimum concentration of the active ingredient(s) in the chosen medium can be determined emperically, according to procedures well known to medicinal chemists. As used herein, "biologically acceptable medium" includes any and all solvents, dispersion media, and the like which may be appropriate for the desired route of administration of the pharmaceutical preparation. The use of such media for pharmaceutically active substances is known in the art. Except insofar as any conventional media or agent is incompatible with the activity of the Elf-1 polypeptide, its use in the pharmceutical preparation of the invention is contemplated. Suitable vehicles and their formulation inclusive of other proteins are described, for example, in the book *Remington's Pharmaceutical Sciences* (Remington's Pharmaceutical Sciences. Mack Publishing Company, Easton, Pa., USA 1985). These vehicles include injectable "deposit formulations". Based on the above, such pharmaceutical formulations include, although not exclusively, solutions or freeze-dried powders of an Elf-1 polypeptide in association with one or more pharmaceutically acceptable vehicles or diluents, and contained in buffered media at a suitable pH and isosmotic with physiological fluids. For illustrative purposes only and without being limited by the same, possible compositions or formulations which may be prepared in the form of solutions for the treatment of nervous sytem disorders with an Elf-1 polypeptide are given in U.S. Pat. No. 5,218,094. In the case of freeze-dried preparations, supporting excipients such as, but not exclusively, mannitol or glycine may be used and appropriate buffered solutions of the desired volume will be provided so as to obtain adequate isotonic buffered solutions of the desired pH. Similar solutions may also be used for the pharmaceutical compositions of Elf-1 polypeptides in isotonic solutions of the desired volume and include, but not exclusively, the use of buffered saline solutions with phosphate or citrate at suitable concentrations so as to obtain at all times isotonic pharmaceutical preparations of the desired pH, (for example, neutral pH).

Methods of introduction of exogenous Elf-1 polypeptides at the site of treatment include, but are not limited to, intradermal, intramuscular, intraperitoneal, intravenous, subcutaneous, oral, and intranasal. In addition, it may be desirable to introduce the pharmaceutical compositions of the invention into the central nervous system by any suitable route, including intraventricular and intrathecal injection. Intraventricular injection may be facilitated by an intraventricular catheter, for example, attached to a reservoir, such as an Ornmaya reservoir.

Methods of introduction may also be provided by rechargable or biodegradable devices, particularly where gradients of Elf-1 concentrations in a tissue is desired. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of an Elf-1 at a particular target site. Such embodiments of the present invention can be used for the delivery of an exogenously purified Elf-1 polypeptides, which has been incorporated in the polymeric device, or for the delivery of Elf-1 polypeptides produced by a cell encapsulated in the polymeric device. The generation of such implants is generally known in the art. See, for example, *Concise Encylopedia of Medical & Dental Materials,* ed. by David Williams (MIT Press: Cambridge, Mass., 1990); the Sabel et al. U.S. Pat. No. 4,883,666; Aebischer et al. U.S. Pat. No. 4,892,538; Aebischer et al. U.S. Pat. No. 5,106,627; Lim U.S. Pat. No. 4,391,909; and Sefton U.S. Pat. No. 4,353,888.

In yet another embodiment of the present invention, the pharmaceutical Elf-1 polypeptide can be administered as part of a combinatorial therapy with other agents. For example, the combinatorial therapy can include an Elf-1 protein with at least one trophic factor. Exemplary trophic factors include nerve growth factor, cilliary neurotrophic growth factor, schwanoma-derived growth factor, glial growth factor, stiatal-derived neuronotrophic factor, platelet-derived growth factor, and scatter factor (HGF-SF).

Another aspect of the invention features transgenic non-human animals which express a heterologous ELF-I gene of the present invention, or which have had one or more genomic Elf-1 gene(s) disrupted in at least one of the tissue or cell-types of the animal. Accordingly, the invention features an animal model for developmental diseases, which animal has an Elf-1 allele which is mis-expressed. For example, a mouse can be bred which has one or more Elf-1 alleles deleted or otherwise rendered inactive. Such a mouse model can then be used to study disorders arising from mis-expressed Elf-1 genes.

Another aspect of the present invention concerns transgenic animals which are comprised of cells (of that animal) which contain a transgene of the present invention and which preferably (though optionally) express an exogenous Elf-1 protein in one or more cells in the animal. The Elf-1 transgene can encode the wild-type form of the protein, or can encode homologs thereof, including both agonists and antagonists, as well as antisense constructs. In preferred embodiments, the expression of the transgene is restricted to specific subsets of cells, tissues or developmental stages utilizing, for example, cis-acting sequences that control expression in the desired pattern. In the present invention, such mosiac expression of the subject polypeptide can be essential for many forms of lineage analysis and can additionally provide a means to assess the effects of, for example, lack of Elf-1 expression which might grossly alter development in small patches of tissue within an otherwise normal embryo. Toward this and, tissue-specific regulatory sequences and conditional regulatory sequences can be used to control expression of the transgene in certain spatial patterns. Moreover, temporal patterns of expression can be provided by, for example, conditional recombination systems or prokaryotic transcriptional regulatory sequences.

Genetic techniques which allow for the expression of transgenes can be regulated via site-specific genetic manipulation in vivo are known to those skilled in the art. For instance, genetic systems are available which allow for the regulated expression of a recombinase that catalyzes the genetic recombination a target sequence. As used herein, the phrase "target sequence" refers to a nucleotide sequence that is genetically recombined by a recombinase. The target sequence is flanked by recombinase recognition sequences and is generally either excised or inverted in cells expressing recombinase activity. Recombinase catalyzed recombination events can be designed such that recombination of the target sequence results in either the activation or repression of expression of the subject Elf-1 polypeptide. For example, excision of a target sequence which interferes with the expression of a recombinent Elf-1 gene, such as one which encodes an antagonistic homolog, can be designed to activate expression of that gene. This interference with expression of the protein can result from a variety of mechanisms, such as spatial separation of the Elf-1 gene from the promoter element or an internal stop codon. Moreover, the transgene can be made wherein the coding sequence of the gene is flanked recombinase recognition sequences and is initially transfected into cells in a 3' to 5' orientation with respect to the promoter element. In such an instance, inversion of the target sequence will reorient the subject gene by placing the 5' end of the coding sequence in an orientation with respect to the promoter element which allow for promoter driven transcriptional activation.

In an illustrative embodiment, either the cre/loxP recombinase system of bacteriophage P1 (Lakso et al. (1992) *PNAS* 89:6232–6236; Orban et al. (1992) *PNAS* 89:6861–6865) or the FLP recombinase system of *Saccharomyces cerevisiae* (O'Gorman et al. (1991) *Science* 251:1351–1355; PCT publication WO 92/15694) can be used to generate in vivo site-specific genetic recombination systems. Cre recombinase catalyzes the site-specific recombination of an intervening target sequence located between loxP sequences. loxP sequences are 34 base pair nucleotide repeat sequences to which the Cre recombinase binds and are required for Cre recombinase mediated genetic recombination. The orientation of loxP sequences determines whether the intervening target sequence is excised or inverted when Cre recombinase is present (Abremski et al. (1984) *J. Biol. Chem.* 259:1509–1514); catalyzing the excision of the target sequence when the loxP sequences are oriented as direct repeats and catalyzes inversion of the target sequence when loxP sequences are oriented as inverted repeats.

Accordingly, genetic recombination of the target sequence is dependent on expression of the Cre recombinase. Expression of the recombinase can be regulated by promoter elements which are subject to regulatory control, e.g., tissue-specific, developmental stage-specific, inducible or repressible by externally added agents. This regulated control will result in genetic recombination of the target sequence only in cells where recombinase expression is mediated by the promoter element. Thus, the activation expression of the receombinant Elf-1 protein can be regulated via control of recombinase expression.

Use of the cre/loxP recombinase system to regulate expression of a recombinant Elf-1 I protein requires the construction of a transgenic animal containing transgenes encoding both the Cre recombinase and the subject protein. Animals containing both the Cre recombinase and a recombinant Elf-1 gene can be provided through the construction of "double" transgenic animals. A convenient method for providing such animals is to mate two transgenic animals each containing a transgene, e.g., an Elf-1 gene and recombinase gene.

One advantage derived from initially constructing transgenic animals containing a Elf-1 transgene in a recombinase-mediated expressible format, particularly derives from the likelihood that the subject protein will be deleterious upon expression in the transgenic animal. In such an instance, a founder population, in which the subject transgene is silent in all tissues, can be propagated and maintained. Individuals of this founder population can be crossed with animals expressing the recombinase in, for example, one or more tissues. Thus, the creation of a founder population in which, for example, an antagonistic Elf-1 transgene is silent will allow the study of progeny from that founder in which disruption of Elf-1 mediated induction in a particular tissue or at developmental stages would result in, for example, a lethal phenotype.

Similar conditional transgenes can be provided using prokaryotic promoter sequences which require prokaryotic proteins to be simultaneous expressed in order to facilitate expression of the transgene. Exemplary promoters and the corresponding trans-activating prokaryotic proteins are given in U.S. Pat. No. 4,833,080. Moreover, expression of the conditional transgenes can be induced by gene therapy-like methods wherein a gene encoding the trans-activating protein, e.g. a recombinase or a prokaryotic protein, is delivered to the tissue and caused to be expressed, such as in a cell-type specific manner. By this method, the Elf-1 transgene could remain silent into adulthood until "turned on" by the introduction of the trans-activator.

In an exemplary embodiment, the "transgenic non-human animals" of the invention are produced by introducing transgenes into the germline of the non-human animal. Embryonal target cells at various developmental stages can be used to introduce transgenes. Different methods are used depending on the stage of development of the embryonal target cell. The zygote is the best target for micro-injection. In the mouse, the male pronucleus reaches the size of approximately 20 micrometers in diameter which allows reproducible injection of 1–2pl of DNA solution. The use of zygotes as a target for gene transfer has a major advantage in that in most cases the injected DNA will be incorporated into the host gene before the first cleavage (Brinster et al. (1985) *PNAS* 82:4438–4442). As a consequence, all cells of the transgenic non-human animal will carry the incorporated transgene. This will in general also be reflected in the efficient transmission of the transgene to offspring of the founder since 50% of the germ cells will harbor the transgene. Microinjection of zygotes is the preferred method for incorporating transgenes in practicing the invention.

Retroviral infection can also be used to introduce transgene into a non-human animal. The developing non-human embryo can be cultured in vitro to the blastocyst stage. During this time, the blastomeres can be targets for retroviral infection (Jaenich, R. (1976) *PNAS* 13:1260–1264). Efficient infection of the blastomeres is obtained by enzymatic treatment to remove the zona pellucida (*Manipulating the Mouse Embryo,* Hogan eds. (Cold Spring Harbor Laboratory Press, Cold Spring Harbor, 1986). The viral vector system used to introduce the transgene is typically a replication-defective retrovirus carrying the transgene (Jahner et al. (1985) *PNAS* 82:6927–6931; Van der Putten et al. (1985) *PNAS* 82:6148–6152). Transfection is easily and efficiently obtained by culturing the blastomeres on a monolayer of virus-producing cells (Van der Putten, supra; Stewart et al. (1987) *EMBO J.* 6:383–388). Alternatively, infection can be performed at a later stage. Virus or virus-producing cells can be injected into the blastocoele (Jahner et al. (1982) *Nature* 298:623–628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al. (1982) supra).

A third type of target cell for transgene introduction is the embryonal stem cell (ES). ES cells are obtained from pre-implantation embryos cultured in vitro and fused with embryos (Evans et al. (1981) *Nature* 292:154–156; Bradley et al. (1984) *Nature* 309:255–258; Gossler et al. (1986) *PNAS* 83: 9065–9069; and Robertson et al. (1986) *Nature* 322:445–448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, R. (1988) *Science* 240:1468–1474.

Methods of making knock-out or disruption transgenic animals are also generally known. See, for example, *Manipulating the Mouse Embryo,* (Cold Spring Harbor Laboratory Press, Cold Spring Harbor, N.Y., 1986). Recombinase dependent knockouts can also be generated, e.g. by homologous recombination to insert recombinase target sequences flanking portions of an endogenous Elf-1 gene, such that tissue specific and/or temporal control of inactivation of an Elf-1 allele can be controlled as above.

Yet another aspect of the invention relates to the novel in situ assay for detecting receptors or their ligands in tissue samples and while organisms. In general, the RAP-in situ assay (for Receptor Affinity Probe) of the present invention comprises (i) providing a hybrid molecule (the affinity probe) including a receptor, or a receptor ligand, covalently bonded to an enzymatically active tag, preferably for which chromogenic substrates exist, (ii) contacting the tissue or organism with the affinity probe to form complexes between the probe and a cognate receptor or ligand in the sample, removing unbound probe, and (iii) detecting the affinity complex using a chromogenic substrate for the enzymatic acitivity associated with the affinity probe. In preferred embodiments, an alkaline phosphatase provides a tag that binds to commercially available antibodies, allowing co-imrnunoprecipitation procedures. More significantly, however, it has an intrinsic enzyme activity that can be traced quantitatively by simple chromogenic assays, without purification, radioactive labeling, or the use of secondary reagents. We find that detection using the enzyme activity of AP fusion proteins provides a sensitivity at least comparable to other approaches, such as the use of purified and $^{125}$I labeled reagents.

Other enzymes which can be used in place of alkaline phosphatase include horseradish peroxidase, β-galactosidase, malate dehydrogenase, yeast alcohol dehydrogenase, α-glycerophosphate dehydrogenase, triose phosphate isomerase, asparaginase, glucose oxidase, and urease. Other enzyme labels which are readily detectable by addition of a corresponding chromogenic substrate are known in the art. See also, Flanagan and Leder PCT Publication W092/06220. The enzyme label can be covalently attached to the receptor or receptor ligand by chemical cross-linking agents known in the art, such as succinimidyl 4-(N-maleimidomethyl)cyclohexane-1-carboxylate (SMCC), m-Maleimidobenzoyl-N -hydroxysuccinimide ester (MBS); N-succinimidyl(4-iodoacetyl) aminobenzoate (SIAB), succinimidyl 4-(p-maleimidophenyl) butyrate (SMPB), or 1-ethyl-3-(3-dimethylamino -propyl) carbodiimide hydrochloride (EDC). Alternatively, recombinant fusion proteins can be generated as described in the examples below.

The present method, unlike the prior art methods which had only been carried out on dispersed cell cultures, provides a means for probing non-dispersed and wholemount tissue and animal samples. The method can be used to detect patterns of expression for particular receptors and their ligands, for measuring the affinity of receptor/ligand interactions in tissue samples, as well as for generating drug screening assays in tissue samples. Moreover, the affinity probe can also be used in diagnostic screening to determine whether a receptor, e.g. an EPH receptor, or its ligand, e.g. Elf-1 or B61 or a LERK protein, are misexpressed.

Exemplification

The invention now being generally described, it will be more readily understood by reference to the following examples which are included merely for purposes of illustration of certain aspects and embodiments of the present invention, and are not intended to limit the invention.

We have previously reported the use of a soluble receptor-AP fusion protein to identify and characterize the ligand of the c-kit receptor (Flanagan and Leder, (1990) *Cell* 63: 185–194; Flanagan et al. (1991) *Cell* 64:1025–1035). Here we extend this approach and show that mek4-AP and sek-AP soluble receptor fusions can be used to localize sites of ligand binding directly in the mouse embryo, in a procedure we term RAP-in situ (for Receptor Affinity Probe). Using this spatial information, the mek4-AP and sek-AP reagents were then employed to identify a ligand clone in an expression library of cDNA from regions of the embryo found to express very high levels of ligand. The entire process of identifying and cloning a ligand by this procedure requires no purification or labeling of protein reagents, and can be rapid, simple and inexpensive.

A novel EPH receptor ligand, "Elf-1 " was identified by this method, and we show that it is a ligand that can bind to both mek4-AP and sek-AP. Elf-1 is an unusual tyrosine kinase ligand in being linked to the membrane through a phosphatidylinositol linkage, a feature that may help to understand some of the unique properties of the EPH family receptors. The sequence of Elf-1 shares some homology to two other EPH receptor ligands, B61 (Bartley et al. (1994) *Nature* 368:558–561; and Holzman et al. (1990) *Mol Cell Biol* 10:5830–5838) and LERK-2 (Beckmann et al. (1994) *EMBO J*13:3757–3762; PCT Publication WO95/11384).

The developmental expression of Elf-1 and its receptors mek4 and sek was compared, revealing complementary domains of expression that delineate potential roles for these molecules in patterning several developmental fields of the vertebrate embryo. The identification of Elf-1 has allowed us to initiate studies into its developmental function. RNA in situ hybridization indicated Elf-1 is expressed by day 8.5 of mouse development, soon after gastrulation. Earlier stages have not yet been examined, but will be of interest, particularly as an apparent homolog of the sek receptor was reported to be expressed in the zebrafish from the onset of gastrulation (Xu et al. (1994) *Development* 120:287–299). We find that Elf-1 and its receptors mek4 and sek are expressed together in several regions of the mouse embryo, including the neural tube, somites, limb buds, retina, and branchial arches. In each of these regions the expression of ligand and receptors is strikingly complementary, implying roles for their interaction.

In the developing neural folds and neural tube the expression of Elf-1, sek and mek4 in complementary patterns in the forebrain, midbrain and hindbrain supports roles in early patterning. In the hindbrain, expression of sek (Nieto et al. (1992) *Development* 116:1137–1150) as well as Elf-1 and mek4 appears to be correlated with the boundaries of the rhombomeres. These segmental structures, visible as morphological bulges, are known to act as cell lineage compartments as well as domains for the expression and action of control molecules such as the Hox genes (Guthrie and Lumsden, (1991) *Development* 112:221–229). The early expression of Elf-1, mek4 and sek in these structures of the hindbrain suggests ftmctions in the establishment or compartmentalization of these segmental structures, or in the activation of the specific molecular program of individual rhombomeres. Early expression of Elf-1, sek and mek4 in the somites similarly suggests roles in the establishment or subsequent fate specification of these metameric structures. It also implies the possibility of parallel molecular mechanisms operating in the rhombomeres and somites, the two major segmental structures of the vertebrate embryo.

The expression patterns in the limb bud are also intriguing. In each limb bud, Elf-1 RNA appears to be expressed in a diffuse central pattern, while sek is expressed in a defined band at the distal end, and mek4 is expressed in a posterior proximal region. It is interesting that this expression shows some correlation with the structures at the distal tip and posterior margin that are known known to play key roles in setting up the proximo-distal and anterior-posterior axes of this developmental field (Tabin, (1991) *Cell* 66:199–217). A similarly complemetary pattern of ligand and receptor expression is seen in the branchial arches. Moreover, the recent observation of mirror image duplications following Hoxa-2 deletion suggests that each branchial arch may be a morphogenetic field in some ways analogous to a limb bud (Gendron-Maguire et al. (1993) *Cell* 75:1317–31; Rijli et al. (1993) *Cell* 75:1333–1349). Patterning in these two areas could therefore involve similar molecular mechanisms. Accordingly, our observations set forth below delineate potential ftmctions for Elf-1 in several important areas of the vertebrate embryo.

Finally, Elf-1 is expressed in the midbrain. This region is where several different sense organs project and form a topographic representation of the outside world. For example, the retinal ganglion cells project onto the tectum (which is a part of the midbrain). The development of projection maps that maintain the spatial order of neuronal connections is a key element of the way the brain is assembled. However, little is known about the molecular mechanisms that control the development of such projections. The properties of Elf-1, and its receptors, described here implicate this molecule as having a role in development of the retinotectal map projection. In particular, the existence of a gradient of Elf-1 in the target field, and a complementary gradient of Mek4 in the field of projecting neurons, makes Elf-1 a strong candidate as a molecule carrying position-specific information that may specify map topography.

Studies of the morphogenetic mechanisms that translate the retinotectal position-specific information into a map suggest a combination of effects on axon guidance, as well as axon retraction and branching, synapse formation and neuronal survival (Walter et al. (1987) *Development* 101:685–696; Jacobson, M. (1991). Developmental Neurobiology. (New York, N.Y.: Plenum press); Simon et al. (1992) *Neuron* 9:977–989; Boxberg et al. (1993) *Neuron* 10:345–357; Goodman et al. (1993) *Cell* 72:77–98; Holt et al. *J. Neurobiol.* (1993) 24:1400–1422). Elf-1 may therefore affect one or more of these processes. Moreover, in addition to providing guidance for the axonal projections, it is quite plausible that Elf-1 could promote the differentiation and/or maintenance of the innervating cells to their axonal processes.

Regarding the receptors in the retina, further work will be required to predict the molecular nature of the signal resulting from receptor occupancy, particularly as two receptors are present, and because ligand binding by Eph family receptors does not necessarily result in receptor activation, and may even cause an inhibition of signaling. However, the expression in the retinal ganglion cells of at least two closely related receptors, Mek4 and Sek, both known to bind Elf-1, suggests models where the decoding of the position-specific information could involve heterodimerization, or differences in occupancy of the two receptors. Such models might help to explain how the axon tips may sense gradients that must be shallow at the level of their individual growth cones. Two-receptor models could also help to explain a critical feature of topographic mapping: that is, how a particular presynaptic cell could have a preference not just for one end of the target gradient, but for a particular location along the gradient.

Elf-1 may have additional roles in nervous system development. For example, tectal expression could provide a mechanism for the aligned development of the multiple visual, auditory, somatosensory and other spatial maps that overlap in precise register in the tectum and coordinate multimodal input and output according to its direction in external space (Udin et al. (1988) *Ann. Rev. Neurosci.* 11:289–327; Holt et al. *J. Neurobiol.* (1993) 24:1400–1422). The expression of Mek4 at the forebrain-midbrain junction in mice, but not in chicks, suggests a possible involvement in thalamocollicular or thalamocortical topographic projections that may have evolved newly in mammals (Udin et al. (1988) *Ann. Rev. Neurosci.* 11:289–327; Jacobson, M. (1991). Developmental Neurobiology. (New York, N.Y.: Plenum press)). In addition, the specific locations of Elf-1, Mek4 and Sek expression in the hindbrain and spinal cord, and in flanking regions such as the branchial arches and somites (see also Nieto et al. (1992) *Development* 116:1137–1150; Soans et al. (1994) *Oncogene* 9:3353–3361 suggest possible roles in patterning the developing cranial and spinal nerves.

The need to generate a complex three-dimensional pattern in development implies that key cellular communication molecules must be able to transmit accurate spatial information. This may explain why, although the first growth factors were identified as soluble molecules, it is increasingly becoming apparent that many, if not most, polypeptide growth factors can exist in forms that are not freely diffusible (Jessell and Melton, (1992) *Cell* 68:257–270; Massague and Pandiella, (1993) *Annu. Rev. Biochem.* 62:515–541). For instance, the known properties of Elf-1 and its receptors seem well suited to a role in transmitting accurate spatial information. The association of Elf-1 with cells of the tectum through a GPI anchor may be a critical feature ensuring that the spatial information it carries is stable and tightly localized. Also, the remarkably high concentrations of Elf-1 protein in the tectum may help in specifying a wide range of distinguishable position-specific values.

For several ligands of tyrosine kinases, this anchorage is mediated by the presence of a C-terminal transmembranc domain. In the case of the kit ligand/steel factor, genetic evidence indicates that -the presence of this transmembrane domain is essential for the molecule to fulfil its normal developmental function (Flanagan et al., supra; Brannan et al., (1991) *PNAS* 88:4671–4674). The precise biological roles of transmembrane anchorage are not clear, but may include tight localization of ligand activity, and may also be related to the ability of these ligands to mediate cell-cell adhesion and to promote cell migration. Still other tyrosine kinase ligands are anchored by interactions with proteoglycans or other molecules in the extracellular or pericellular matrix. These interactions not only localize the ligands, but can also have major effects on their biological activity (Bemfield et al., (1992) *Annu. Rev. Cell Biol.* 8:365–393; and Jessell and Melton, supra).

Like many of these other ligands for receptor tyrosine kinases, Elf-1 expressed in transfected cells is presented at the cell surface. However, the mechanism of this anchorage is unusual in that it apparently involves a linkage to the membrane via a C-terminal phosphatidylinositol glycan tail. This mode of anchorage exists both in cell lines, where cell surface ligand was released by PI-PLC treatment, and also in embryos, where all reactivity in RAP-in situ experiments with mek4-AP and sek-AP was removed by pretreatment with PI-PLC. Like Elf-1, the related polypeptide B61 also shows cell surface anchorage that is sensitive to PI-PLC (Holzman et al., supra; Bartley et al., supra). These findings suggest that phosphatidylinositol linkage may emerge as a general feature of the EPH receptor ligand family.

The presence of a phosphatidylinositol linkage on Elf-1 and B61 adds a novel dimension to the anchorage mechanisms of the ligands for receptor tyrosine kinases. One proposed function of this linkage is to ensure cell-cell interactions. For example, the establishment and compartmentalization of the rhombomeres clearly implies the existence of segment-specific cell-cell interactions. Spatially restricted cellular interactions such as these could well be mediated by the interaction of EPH family receptors with ligands such as Elf-1 anchored in the membranes of adjacent cells. An irnmunohistochemical study of the nuk receptor is also intriguing in this regard (Henkemeycr et al., (1994) *Oncogene* 9:1001–1014). Expression was detected in the early nervous system at sites of cell-cell contact, often involving migrating neuronal cells, and in the initial axon outgrowths of the nervous system. These observations suggest functions in the guidance of neuronal migration and in the pathfinding and/or fasciculation of the earliest axons. The presentation of Elf-1 or other EPH receptor ligands in a cell surface form with a phosphatidylinositol linkage could play an important part in determining the spatial specificity of these unique cell-cell interactions that play a critical role in early stages of patterning the developing vertebrate embryo.

EXAMPLE 1

Localization of Ligand(s) for mek4 and sek by RAP In Situ

To search for ligands for the EPH family members mek4 and sek, cDNAs encoding the receptor extracellular domains were inserted into the vector APtag-l (Flanagan and Leder, supra). The resulting constructs encode the receptor extracellular domain, presumed to bind extracellular ligand(s), fused to placental alkaline phosphatase (FIG. 1A). The alkaline phosphatase provides a tag that binds to commercially available antibodies, allowing co-immunoprecipitation procedures. More significantly, it has an intrinsic enzyme activity that can be traced quantitatively by simple chromogenic assays, without purification, radioactive labeling, or the use of secondary reagents. We find that detection using the enzyme activity of AP fusion proteins provides a sensitivity at least comparable to other approaches, such as the use of purified and $^{125}$I labeled reagents.

Figure 1B:
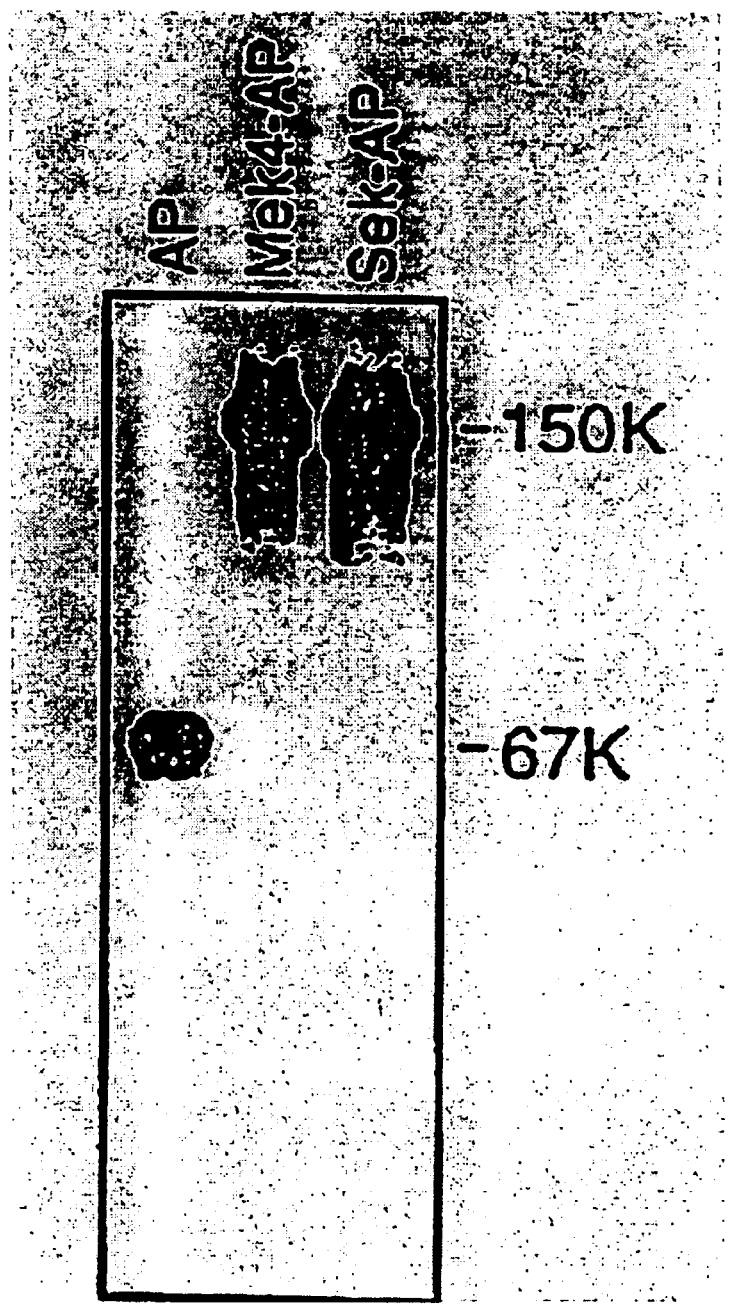
FIG. 1B demostrates that the Mek4-AP and Sek-AP fusion proteins are expressed and secreted into the supernatants of transfected NIH-3T3 cells. Cells were metabolically labeled with $^{35}$S-methionine, then the supernatants were immunoprecipitated with a monoclonal antibody against human placental alkaline phosphatase, separated on a 10% polyacrylamide gel, and autoradiographed. Unfused AP is shown for comparison.

FIG. 1B shows that mek4-AP and sek-AP are secreted proteins, and each was produced as a single major polypeptide with the expected apparent molecular weight of approximately 150 kD. The fusion proteins had alkaline phosphatase enzyme activity, with a specific activity similar to that reported previously (Flanagan and Leder, supra). Individual clones of transfected cells selected for secretion of high alkaline phosphatase activity produced approximately 5 µg/ml of fusion protein in the supematant. For all subsequent experiments described here the supematants could be used as a source of the soluble receptor reagent without purification.

As the mek4 and sek receptors are known to be expressed at high levels in embryonic development, we decided to test whether the mek4-AP and sek-AP reagents could be used to detect their ligand(s) directly in mouse embryos. Whole embryos were treated with receptor-AP fusion protein, washed, and then tested for bound fusion protein using standard histochemical stains for AP activity. Briefly, whole embryos at day 9.5 of development were treated with supernatants containing receptor fusion proteins, or unfused AP as a control, then were washed, fixed and stained for bound AP activity. The thin roof of the fourth ventricle in the hindbrain was punctured to allow exchange of reagents with the lumen of the neural tube, resulting in a slight distortion of the embryos in this region. A characteristic pattern of staining was detected when either mek4-AP or sek-AP was used to test whole-mount preparations of mouse embryos. Areas that appeared to show specific staining include the following: midbrain and anterior hindbrain, branchial arches, dorsal face of the spinal cord, somites, and limb buds. Similar staining was not seen in controls using unfused AP or when other receptor-AP fusion proteins were used. The patterns seen with mek4-AP and sek-AP were similar to one another, with the strongest reactivity in both cases seen in the region of the presumptive midbrain and anterior hindbrain. Reactivity was also seen in other areas, including the region of the somites, the branchial arches, a stripe down the dorsal face of the neural tube posterior to the hindbrain, limb buds, and retina. Strong, specific staining was also seen in embryos at day 8.5 and 10.5 of development. The exact tissues and cell types showing reactivity have not yet been characterized in detail. In addition, it should be noted that the conditions used for these experiments were selected to minimize background staining and the possibility of losing or denaturing the ligand. The short incubation times and the absence of permeabilizing agents may favor staining of structures near the surface of the embryo. Also, as the embryos were not fixed prior to treatment with the receptor-AP reagents, the protocol used here may not be suitable for detecting freely diffusible ligands. However, in other experiments we find that the RAP-in situ procedure can be modified to use fixed embryos, perhaps making detection of soluble ligands feasible. For example, embryos can be pre-fixed in 4% paraformaldehyde at 4° C. overnight, then treated with the AP-tagged protein in 1% Triton X-100.

EXAMPLE 2

Expression Cloning of Elf-1 from Mouse Embryos

The strong reactivity of the presumptive midbrain and anterior hindbrain in the RAP-in situ of mouse embryos suggested that one or more ligands for mek4 and sek is expressed at high levels in this region. We therefore initiated an expression cloning strategy to isolate cDNA for a putative ligand expressed there. The appropriate region of the midbrain and hindbrain was excised from 80 mouse embryos at day 9.5 of development. RNA was prepared and was used to construct a cDNA library in the eukaryotic expression vector CDM8 (Seed and Aruffo (1987) *PNAS* 84:3365–3369). The library was produced as pools of approximately 1,000 independent clones and was screened by a sib selection procedure. DNA from each pool was transiently transfected into a plate of COS cells. The cells were then tested by treating with mixed mek4-AP and sek-AP supernatants, washing, and staining for alkaline phosphatase activity in situ. After screening 36 pools, one positive pool was detected. This pool was readily identifiable by the presence of intense AP staining that was coincident with the surfaces of several individual cells scattered around the plate. The positive pool was subdivided and rescreened, and after a total of three rounds of screening, a single positive cDNA clone, Elf-1, was isolated.

Figure 2B:
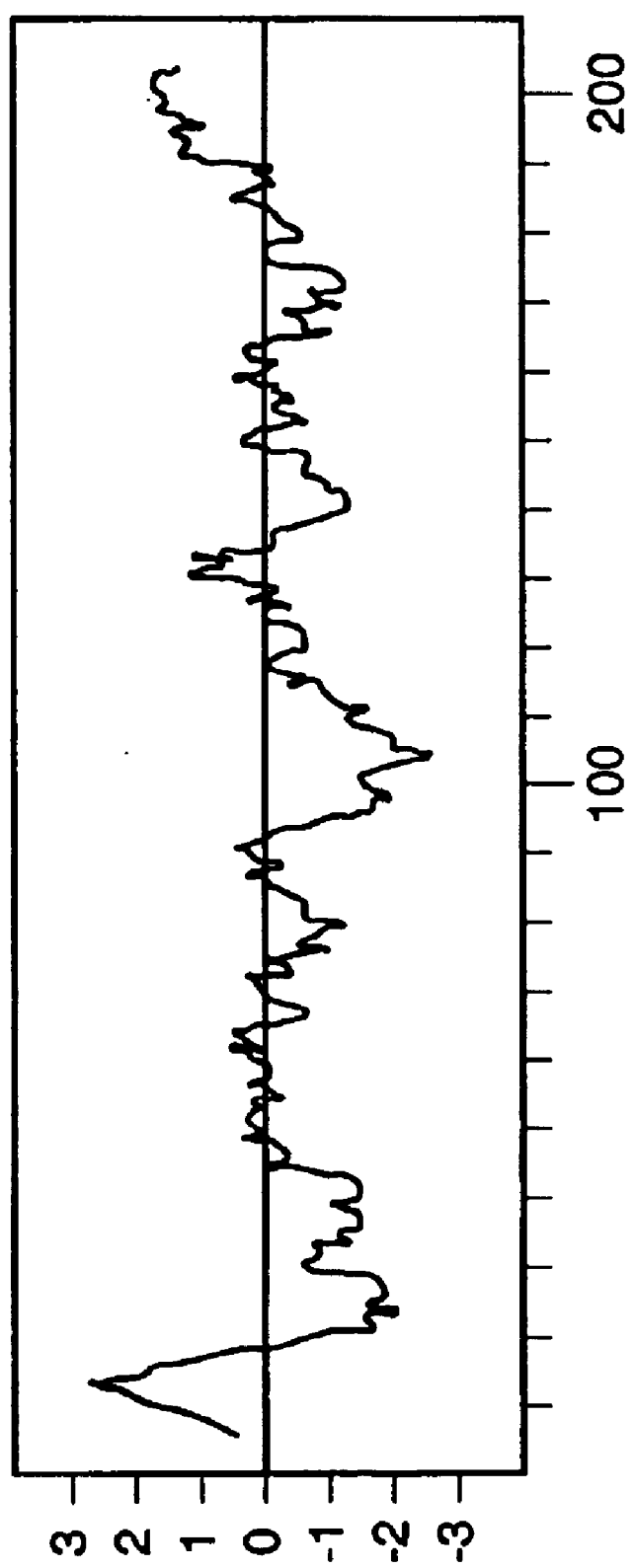
FIG. 2B is a hydrophobicity plot of the predicted Elf-1 polypeptide.

Nucleotide sequencing of the positive cDNA clone revealed a single long open reading frame that could encode a polypeptide of 209 amino acids (FIG. 2A, and SEQ ID Nos: 1 and 2). The open reading frame is followed by a typical 3' untranslated sequence containing a polyadenylation signal and a poly(A) tail. The N-terminus of the deduced protein sequence begins with a methionine residue in a DNA sequence context consistent with a translation initiation site (Kozak, (1987) *Nucl. Acids Res* 15:8125–8148), and is followed by an apparent signal sequence for peptide secretion (von Heijne, (1990) *J Membrane Biol* 115:195–201). The secretion signal is followed by an amino acid sequence containing six cysteine residues and three potential N-linked glycosylation sites. The C-terminus ends with a stretch of fifteen predominantly hydrophobic amino acids (FIGS. 2A and 2B), suggesting the presence of a signal for addition of a phosphatidylinositol glycan tail that could anchor the polypeptide in the plasma membrane (Ferguson and Williams, (1988) *Annu Rev Biochem* 57:285–320).

A search of the Genbank database did not reveal any sequences identical or nearly identical to the polypeptide shown in FIG. 2A. This polypeptide appears to be a novel molecule which we have named Elf-1, for EPH ligand family-1. Two sequences in the database that did show obvious homology to Elf-1. One peptide, called B61, was identified in a screen for mRNAs that could be induced by TNF-αtreatment of endothelial cells (Holzman et al. (1990) *Mol Cell Biol* 10:5830–5838) and was recently shown to be a ligand for the Eck receptor tyrosine kinase (Bartley et al. (1994) *Nature* 368:558–561). Another ligand, LERK-2, has been identified as a ligand for the elk receptor (Beckmann et al. (1994) *EMBO J*13:3757–3762). An alignment of the sequences of Elf-1 and B61 demonstrates an amino acid identity of 45% overall. The sequence conservation is strongest over the N-terminal 145 amino acids of the predicted mature Elf-1 peptide, with a sequence identity of 53%, and conservation of all four cysteines in this part of the molecule. The GAP alignment of Elf-1 and LERK-2 gives an overall identity of 28%. The C-terminal tail shows poor conservation of primary sequence amongts all three proteins and in the Elf-1 protein, could serve primarily as a linker for attachment to the membrane.

The EPH family receptors themselves show a high degree of sequence conservation. In particular the close sequence similarity of their extracellular domains is unusual, generally showing identity in the 40–60% range in pairwise alignments within the family. For comparison, the extracellular domains of the PDGF α and β receptors, which can bind the same ligand, show 30% identity to one another, and 20% identity to c-kit, a member of the same subclass that binds a different ligand. Among the EPH family receptors, the Eck receptor is distant on the phylogenetic tree of the family from mek4 and sek, which are closely related to one another (Maisonpierre et al., (1993) *Oncogene* 8:3277–3288; and Tuzi and Gullick (1994) *Br J Cancer* 69:417421). This makes it all the more noteworthy that Elf-1, LERK-2, and B61 are somewhat related. The similarity of these ligands, particularly of the conserved cysteines, for relatively divergent members of the EPH family suggests that other ligands for EPH family receptors may also prove to have good conservation of primary sequence, but also that some overlap in receptor activation may be possible such that Elf-1 may have slight agonistic, and possibly even antagonistic activity when contacted with cells expressing EPH receptors more distantly related to the hek-related or sek-related receptors.

EXAMPLE 3

Elf-1 is a Cell Surface Ligand for mek4-AP and sek-AP

Figure 3A:
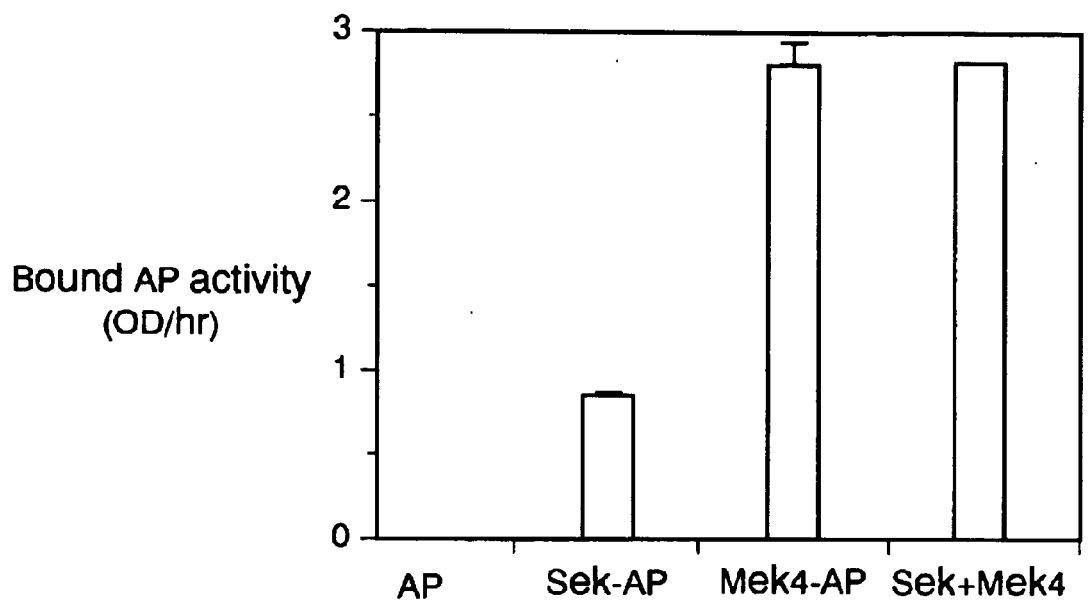
FIGS. 3A–F illustrate quantitative cell surface binding of mek4-AP and sek-AP. Cells were treated with supernatants containing mek4-AP, sek-AP or unfused AP as a control. The cells were then washed, lysed and assayed calorimetrically for bound AP activity.
Figure 3D:
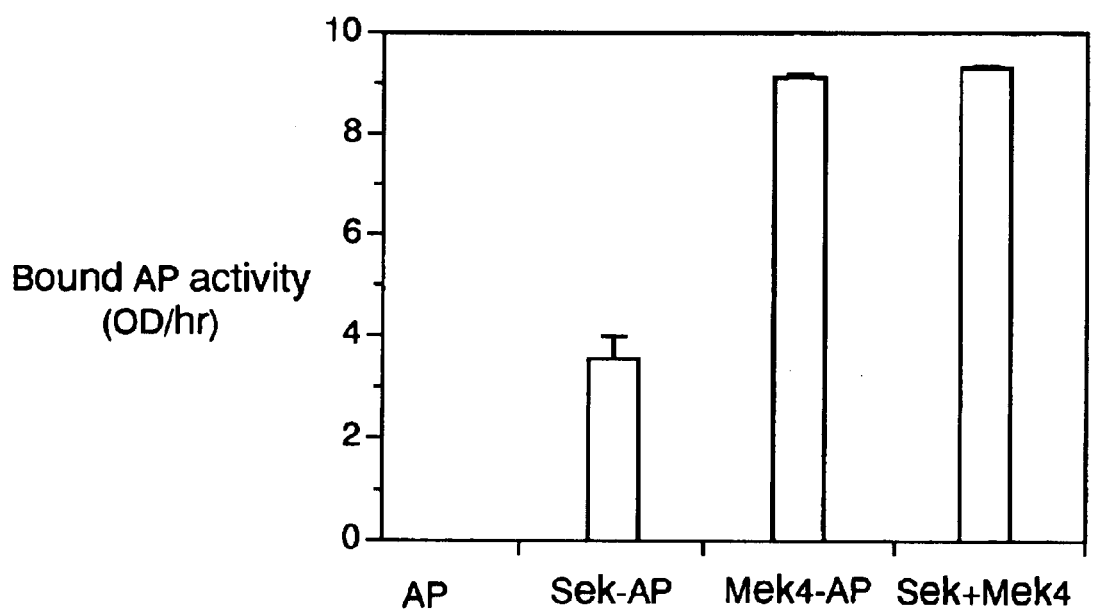
Figure 3B:
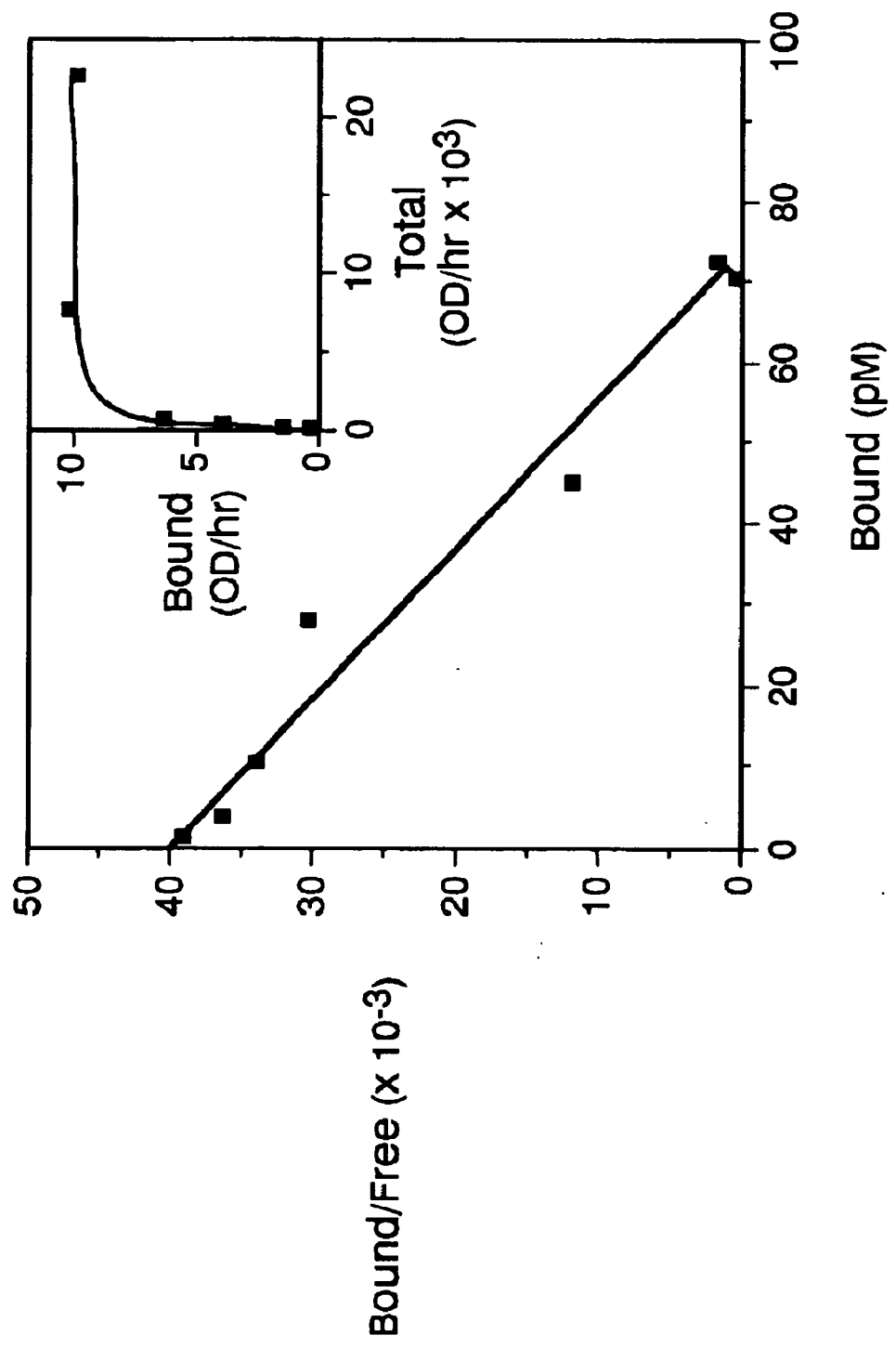
Figure 3C:
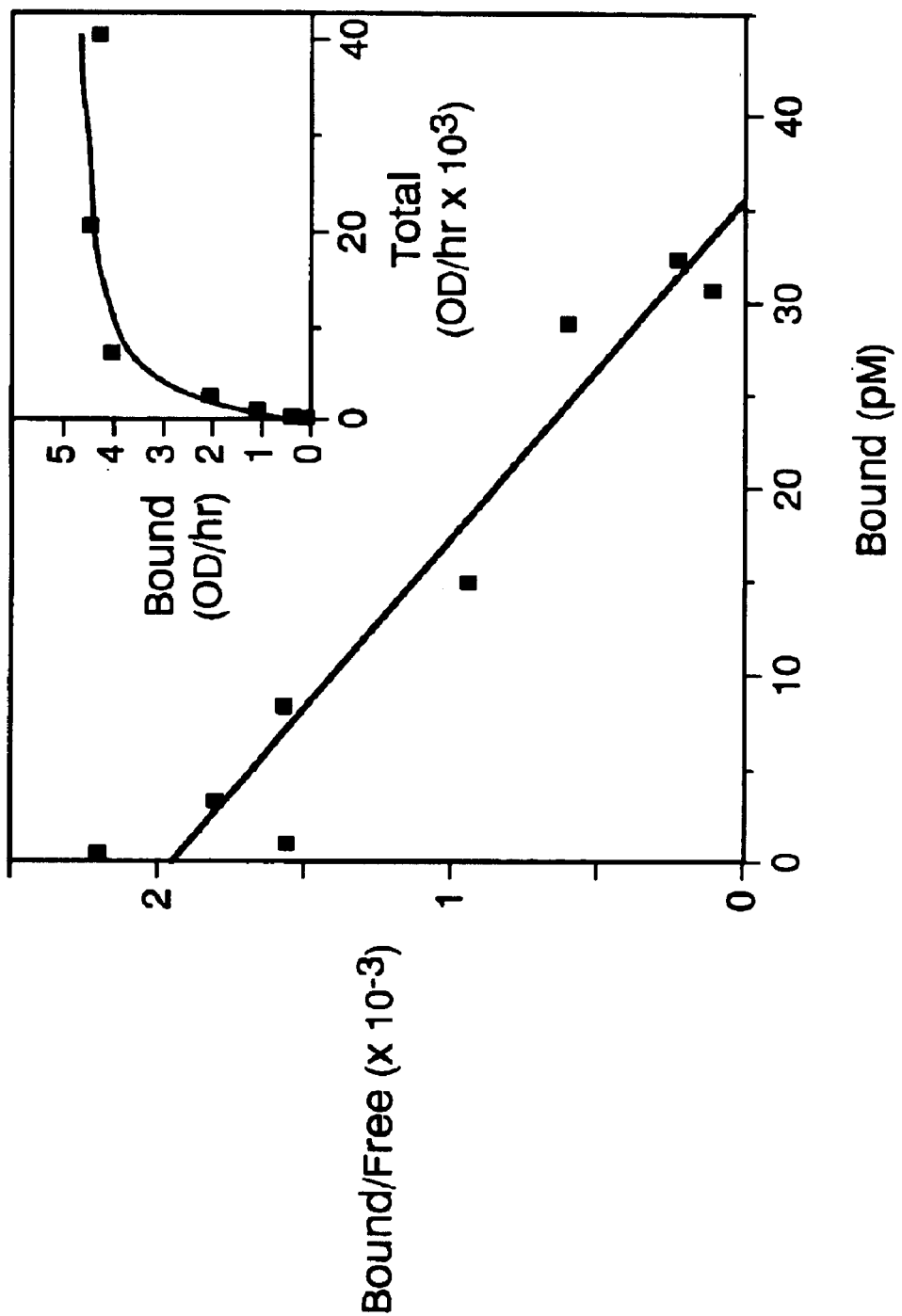

A quantitative analysis of the binding of mek4-AP and sek-AP to cell surface Elf-1 is shown in FIG. 3A–C. After transient transfection of Elf-1 into COS cells, binding of both mek4-AP and sek-AP to the cell surface can be detected, indicating that both of these receptor fusion proteins can bind to Elf-1 on the cell surface (FIG. 3A). When saturating amounts of both mek4-AP and sek-AP are added simultaneously, the total AP binding is not additive, further confirming that they bind to the same ligand (FIG. 3A). A Scatchard analysis of the binding is shown in FIG. 3B and 3C. For both mek4-AP and sek-AP the binding is saturable. Scatchard analyses produced values for the dissociation constants of approximately $10^{-9}$ M for mek4-AP and approximately $10^{-8}$ M for sek-AP (FIG. 3B and 3C).

Figure 3E:
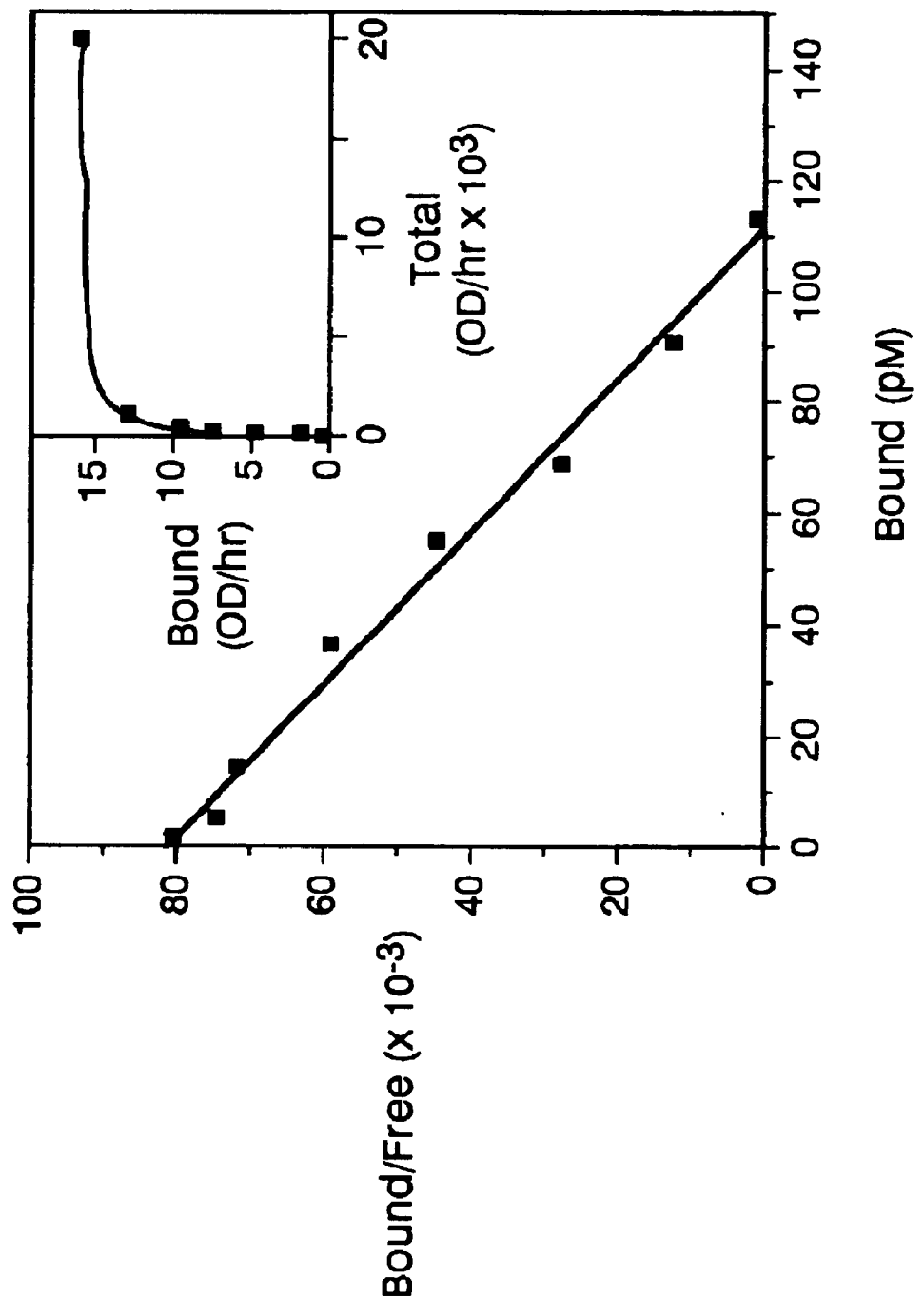
Figure 3F:
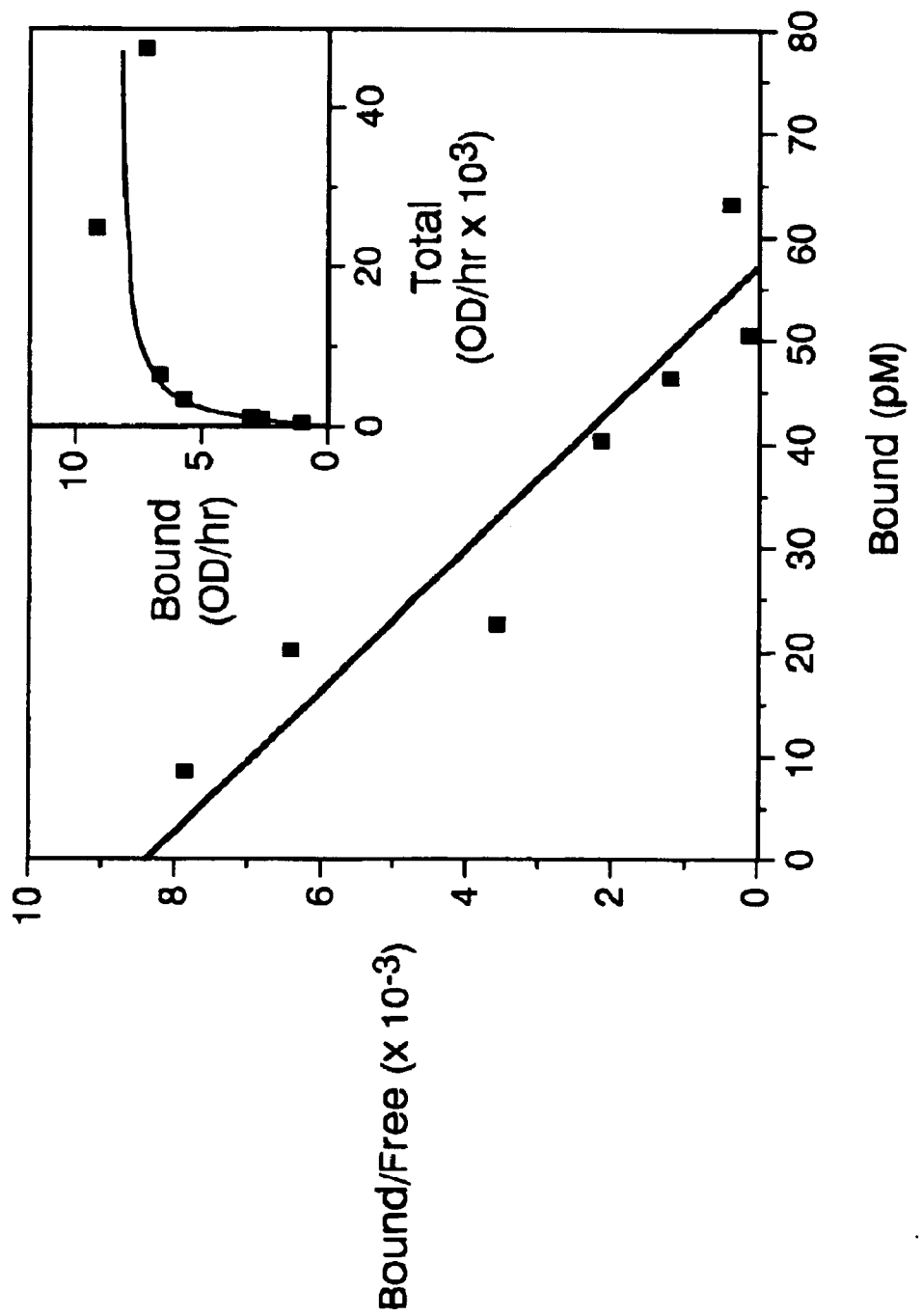

A panel of cell lines was tested with mek4-AP and sek-AP for endogenous expression of a cell surface ligand. Briefly, cells were treated with supernatants containing mek4-AP, sek-AP or unfused AP as a control, each at 1,000 OD/hr/ml. The cells were then washed, lysed and assayed colorimetrically for bound AP activity. Some were found to be negative for binding, while others gave binding that was well above the AP control background. The highest binding was shown by the rat liver stromal cell line BRL-3A, the mink lung fibroblast line Mv1Lu, and two neural crest cell lines, NC7mycblue and NC7EIablue. The BRL-3A cell line was analyzed further. As in the case of COS cells transfected with Elf-1, simultaneous treatment of BRL-3A cells with mek4-AP and sek-AP did not give additive binding of AP activity, indicating that the two fusion proteins bind to the same sites on the cell surface (FIG. 3D). A Scatchard analysis of binding to BRL-3A cells (FIGS. 3E and 3F) indicated binding affinities for both mek4-AP and sek-AP that are similar to those found with Elf-1 in COS cells, consistent with Elf-1 being a ligand expressed on BRL-3A cells. The number of binding sites per BRL-3A cell is approximately 50,000. In situ staining was also used to examine the cell surface binding of mek4-AP and sek-AP to BRL-3A cells, and indicated expression of the ligand over the whole cell surface. It is interesting to note that RAP-in situ staining of the mouse embryo midbrain/hindbrain region was obvious within two minutes, whereas comparable staining of the BRL-3A cells took several hours to develop. This difference of approximately two orders of magnitude suggests that the ligand polypeptide is present at remarkably high levels in the embryo.

The binding affinities measured here were determined for the interaction between a tagged soluble receptor and a membrane bound ligand, rather than the more usual measurement between a membrane bound receptor and a soluble ligand labeled by chemical modification. However, other AP-tagged receptors or ligands have produced measured affinities in line with expected values (for example, Flanagan and Leder, supra; Morrison and Leder, (1992) *J Biol Chem* 267:11957–11963; and Omitz et al., supra). Moreover, in the case of a receptor and a ligand which are both membrane bound in their native state, neither type of measurement may truly reflect the avidity of the interaction in vivo, though both types of measurement can give some indication of the likely strength of this interaction.

The KD of approximately $10^{-9}$ M for the binding of Elf-1 to mek4-AP is within the typical range of affinities for ligands binding to their cognate receptor tyrosine kinases, making it likely that this represents a genuine, biologically significant ligand-receptor interaction. The KD estimate of $10^{-8}$ M for Elf-1 binding to sek-AP is an affinity lower than many known receptor-ligand interactions, though not all. In this context it is worth noting that a similar, or slightly weaker, KD of approximately $2-3 \times 10^8$ M was reported for the interaction of the Eck receptor with its kinase-activating ligand B61 (Bartley et al., supra).

Several additional factors are relevant in considering the potential biological significance of such an interaction. First, the avidity of the interaction between a receptor and a ligand that are both presented at the cell surface is likely to be greatly enhanced by the cooperative effect of highly multivalent ligand-receptor binding between two apposed membranes. Second, our results suggest that Elf-1 is present at very high localized concentrations in the embryo, another factor that would favor interaction with a receptor of moderate affinity. Additional support for the biological significance of the interaction of Elf-1 with mek4 and sek comes from our in situ studies of mouse embryos. RAP-in situ with either mek4-AP or sek-AP detected a pattern of ligand distribution that was subsequently found to be strikingly similar to the pattern of Elf-1 RNA expression. Furthermore, the in situ RNA hybridization results, described further below, indicated that in several regions of the midgestation embryo, mek4 and/or sek are expressed in patterns that are complementary to the areas of Elf-1 expression, providing further evidence in support of interactions between these molecules during development. It is also possible that Elf-1 may bind to other EPH family receptors or that mek4 and sek may have additional ligands.

EXAMPLE 4

Elf-1 Attachment to the Cell Surface is Sensitive to PI-PLC in Cell Lines and Embryos The hydrophobic C-terminus of Elf-1 suggested a signal for covalent linkage to a phosphatidylinositol glycan moiety. Such a linkage could account for the observed association of Elf-1 with cell surfaces. This possibility was tested by treatment with phosphatidylinositol-specific phospholipase C (PI-PLC), an enzyme that cleaves phosphatidylinositol linkages and might therefore be expected to release Elf-1 from the cell surface. mek4-AP and sek-AP binding activity is removed from the cell surface after PI-PLC treatment of either COS cells transfected with Elf-1, or BRL-3A cells. Binding activity of the ligand is not destroyed by this treatment, as co-immunoprecipitation experiments indicated that PI-PLC treatment also results in release of ligand polypeptide into the cell supernatant. It therefore appears that cell surface Elf-1 in transfected COS cells, and the cell surface ligand expressed endogenously in BRL-3A cells, are attached to the cell membrane via a phosphatidylinositol glycan linkage.

The effect of PI-PLC was also tested on embryos. In RAP-in situ experiments, prior treatment of the embryos with PI-PLC resulted in a reduction of mek4-AP or sek-AP staining to background levels. In the embryo too, it therefore appears that the ligand(s) detected by mek4-AP and sek-AP are held in place by an association with cell surfaces via a phosphatidylinositol glycan linkage.

EXAMPLE 5

In Situ Hybridization Analysis of Elf-1 RNA Expression in Mouse Embryos

The RAP-in situ experiments with mek4-AP and sek-AP indicated that these receptors can bind to a ligand in mouse embryos. It was therefore of interest to compare the RAP-in situ results with the expression pattern of Elf-1 determined by RNA hybridization in situ. If Elf-1 is indeed a ligand detected by the RAP-in situ procedure, it would be expected that the RNA hybridization in situ and the RAP-in situ should overlap in at least some areas.

An RNA probe was prepared from the 3' end of the Elf-1 clone and was used to examine mouse embryos by whole mount in situ hybridization. The expression pattern detected by the Elf-1 RNA probe in day 9.5 embryos was similar to that seen in the RAP-in situ experiments with mek4-AP and sek-AP. The strongest expression was again seen in the region of the presumptive midbrain and anterior hindbrain. As in the RAP-in situ experiments, the color development in this region was rapid, being readily visible in less than ten minutes, consistent with a high level of Elf-1 RNA expression. Other areas of RNA expression were also very similar to those seen in the RAP in situ, although no obvious signal was seen with the Elf-1 RNA hybridization probe over the dorsal face of the presumptive spinal cord, where a prominent stripe of reactivity was seen with the mek4-AP and sek-AP reagents.

To obtain further information on the potential roles of Elf-1, mek4 and sek in the embryo, the expression patterns of all three molecules were compared by whole mount in situ hybridization of embryos at days 8.5, 9.5, and 10.5 of development. We present our initial observations here. The sek expression pattern has also been described more extensively elsewhere (Nieto et al. (1992) *Development* 116:1137–1150). In several separate developmental fields of the embryo, the ligand and the two receptors are expressed in patterns that are adjacent and complementary, implying roles for their interactions in patterning of these areas.

These regions include the neural tube, branchial arches, somites and limb buds. Expression of Elf-1 and sek RNA is seen by the earliest time point analyzed (day 8.5). Expression of mek4 RNA was less obvious at this time point, but was present at high levels by day 9.5. In the neural tube, a region of very high Elf-1 expression in the midbrain and anterior hindbrain (metencephalon) was flanked on one side by a region of high mek4 and sek expression near the forebrain-midbrain junction, and on the other side by regions of mek4 and sek expression in the hindbrain. Expression of sek in this region is especially high in rhombomeres 3 and 5, as reported previously (Nieto et al., supra). The expression of mek4 also appears to be highest in different rhombomeres. Elf-1 RNA expression in the somites, branchial arches and limb buds appears in a broad, diffuse pattern at this level of analysis. The sek and mek4 receptors are expressed in these same structures, and within each are restricted to smaller subregions. Thus, in the somites, mek4 is restricted to the dorsal and/or ventral parts, while sek is expressed in each new condensing somite in the day 8.5 embryo, and also in the dorsal part of each somite at later stages. In the limb buds, sek is expressed in a band at the distal tip while mek4 is expressed in a posterior proximal region, as well as in the lateral plate between the limb buds. The expression in the branchial arches is complex, but again mek4 and sek appear in localized subregions.

EXAMPLE 6

Detection of Genomic Elf-1 Genes in Both Mouse and Human Cells

We have performed a genomic Southern blot on both mouse and human cDNA. Six samples of genomic DNA from each species were cut with six different restriction enzymes (XhoI, BamHI, ScaI, XbaI, EcoRI, and NotI). The probe was a 1.1 kb fragment of the Elf-1 clone extending from a PstI site in the middle of the Elf-1 coding sequence to the 3' end of the cDNA. The blots were washed at high stringency (0.1×SSC, 65° C.), and in each sample for both species, a single prominant hybridizing band was detected.

EXAMPLE 7

Elf-1 RNA Expression in the Developing Tectum

In the mouse embryo, as described above, we found that Elf-1 is expressed from the neural fold stage at the start of organogenesis, with the highest levels in the presumptive midbrain. Since the optic tectum (or superior colliculus in mammals) forms a major part of the midbrain, this observation suggested a possible involvement of Elf-1 in the retinotectal projection. To examine this possibility further, we cloned a homolog of Elf-1 from the chicken, a species where the developing retina and tectum are especially prominent, and where the retinotectal projection has been characterized extensively.

Alignment of the mouse Elf-1 sequence with the amino acid sequence deduced from the chick cDNA clone cEl-6 (FIG. 4) indicates an overall amino acid identity of 72% for the mature polypeptides, excluding the predicted secretion signal sequences, rising to an identity of 88% over a core region (residues 61–150 of SEQ ID No. 4) that includes the four cysteines apparently conserved amongst Eph family ligands. In view of the close homology of the mouse and chick sequences, as well as the similarity in RNA expression patterns, described further below, the chick sequence described here is an ortholog of mouse Elf-1.

The distribution of Elf-1 RNA in chick embryos was examined by whole-mount in situ hybridization. The expression pattern is similar to that described in the mouse (see above) with high levels in the midbrain, and other areas of expression including the anterior hindbrain, branchial arches, somites and limb buds. In the chick, the midbrain expression can be seen to be localized to the optic tectum. Tectal expression of Elf-1 RNA is clearly detectable by day 3 of development well before the retinal axons start to arrive in the tectum on day 6 (Lavail et al. (1971) *Brain Res.* 28:391419). Weaker expression is also detected on day 2. Prominent expression of Elf-1 RNA in the tectum continues to be seen on day 4, day 6 and day 8.

Within the optic tectum, Elf-1 RNA expression is not uniform. In particular, it is noteworthy that by day 3, and more clearly on days 4, 6 and 8 Elf-1 RNA is expressed in a gradient, with low levels at the anterior end of the tectum, and high levels at the posterior end. The finding that Elf-1 RNA is not only expressed in the chick optic tectum, but that within the tectum it is expressed in a prominent gradient, further implies a role for Elf-1 in the retinotectal projection, and would be consistent with a function in specifying map topography.

EXAMPLE 8

Mek4 and Sek Receptor RNA Expression in the Ganglion Cell Layer of the Developing Retina Within the developing retina, the cell type that sends axonal projections to the tectum is the retinal ganglion cell (Jacobson, M. (1991). Developmental Neurobiology. (New York, N.Y.: Plenum press). It was therefore of interest to test whether Mek4 and Sek, the known receptors for Elf-1, might be present in the ganglion cells of the developing retina. Consistent with this possibility, in an earlier Northern blot survey of adult tissues, the chick homologs of Mek4 and Sek (also called respectively Cek4 and Cek8 in the chicken) were found to be expressed at highest levels in the adult brain and adult retina (Sajjadi et al. (1993) *Oncogene* 8:1807–13). To examine the cellular localization of expression in the developing retina, cross-sections of chick retinas were hybridized with probes for chick Mek4 and Sek RNA. The results demonstrate a conspicuous expression of both Mek4 and Sek in the retina, with both of them specifically localized to the ganglion cell layer. It also remains possible that other receptors for Elf-1, in addition to Mek4 and Sek, could be expressed in the retinal ganglion cells, especially as the Eph receptors form a large family that may have additional uncharacterized members.

The gradients that are postulated to mediate topographic mapping are formally analogous to morphogenetic gradients that specify position in other fields such as the early Drosophila embryo (St Johnston et al. (1992) *Cell* 68:201–219). However, according to the chemoaffinity theory, topographic mapping is expected to have an added requirement for complementary gradients in two separate fields. Therefore, since Elf-1 RNA is in a gradient in the tectum, we were interested to determine whether one of its receptors might be in a gradient in the retina.

To test this possibility, whole-mount preparations of developing chick retinas were hybridized to chicken Mek4 and Sek probes. In multiple experiments, the distribution of Mek4 hybridization signal was consistently seen in a gradient along the nasotemporal axis, with highest levels near the temporal pole. The distribution of Sek receptor RNA appeared to be uniform across the retina, with no consistent gradation seen in repeated experiments. In retinal cross sections too, where the ganglion cell layer can be seen specifically, Sek expression was seen at comparable levels on the nasal and temporal sides whereas Mek4 expression was seen at higher levels on the temporal side than on the nasal side.

EXAMPLE 9

Detection of Ligand Activity by RAP In Situ of the Developing Tectum

The results of RNA hybridization in situ with the ligand and its receptors suggested that Elf-1 protein might form a gradient in the tectum that could be detected by the Mek4 and Sek receptors in the retinal ganglion cells. To test this more directly we analyzed the tectum by the RAP in situ technique described above, wherein soluble receptor-AP (alkaline phosphatase) fusion proteins were used to detect the distribution of ligand activity directly in tissues. Because this method detects natural ligand-receptor interactions, the information obtained is qualitatively different from in situ RNA hybridization or immunohistochemistry (Cheng et al. (1994) *Cell* 79:157–168). The results show that the Mek4 receptor can indeed detect ligand activity in the tectum. Moreover, the activity is in a gradient, with high levels at the posterior end and low levels at the anterior end. Similar results were obtained by RAP in situ with the Sek receptor as a probe. This ligand gradient is strikingly similar to the gradient of Elf-1 RNA, implying that Elf-1 is a major ligand detectable in the tectum by the Mek4 and Sek receptors.

Many cell-cell communication factors are spatially localized by associations with cell surfaces or the extracellular matrix (Jessell et al. (1992) *Cell* 68:257–270). As set out in the examples above, we found that mouse Elf-1 in cell lines and in embryos appears to be localized to cell surfaces by a glycosyl phosphatidylinositol (GPI) anchor, a feature found in some other members of the Eph ligand family (Bartley et al. (1994) *Nature* 368:558–560) but not so far identified in any other classes of ligands that bind to tyrosine kinase receptors. To determine whether the ligand detected by RAP in situ in the chick tectum may also be localized by a GPI anchor, embryos were treated with phosphatidylinositol-specific phospholipase C (PI-PLC). PI-PLC pretreatment reduced the levels of binding in the RAP in situ protocol essentially to background levels. Though soluble forms of ligand could also exist in the embryo, these results indicate that the ligand detected in the chick tectum by RAP in situ is attached to tectal cell membranes by a GPI anchor.

EXAMPLE 10

Comparison of EPH Receptor Ligands

Figure 5:
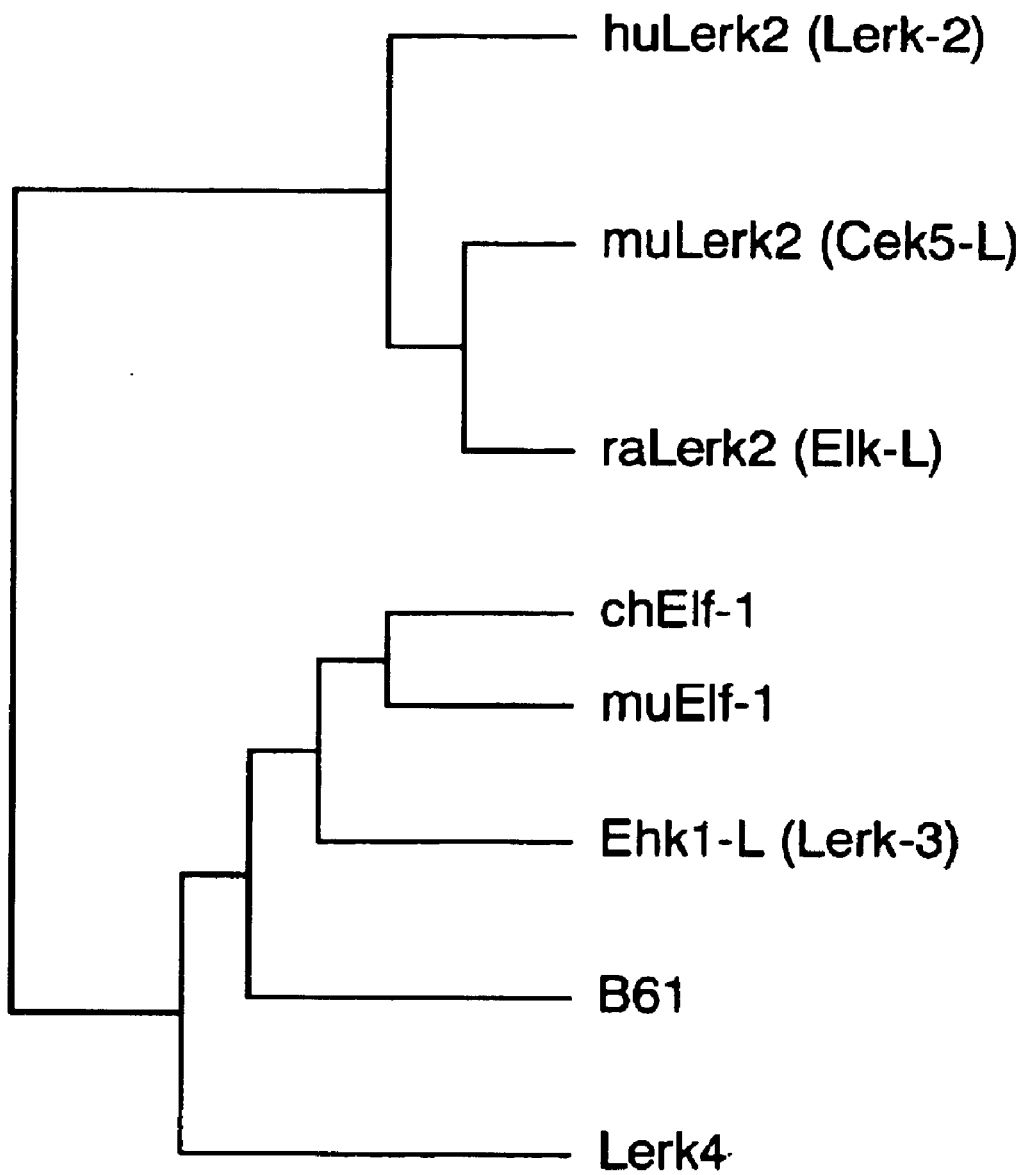
FIG. 5 is a dendrogram illustrating the relative similarity of known EPH receptor ligands.

A multiple sequence alignment was generated with the amino acid sequences for the handful of EPH receptor ligands known, including orthologs. FIG. 5 demonstrates by way of a dendrogam the predicted evolutionary relationship between the ligands. Table 1 below provides approximate amino acid homologies (i.e. percent identity) between each of the ligands. In each instance, the percent homolgy for the whole sequence is given, followed by the percent homology for the core sequence motif.

TABLE 1

|        | B61     | EHK1-L  | LERK-4  | LERK-2  |
|--------|---------|---------|---------|---------|
| ELF-1  | 44 (54) | 48 (61) | 44 (55) | 29 (36) |
| B61    |         | 42 (62) | 39 (44) | 33 (39) |
| EHK1-L |         |         | 44 (54) | 30 (35) |
| LERK-4 |         |         |         | 30 (31) |

Comparison of the mouse and chicken Elf-1 sequences reveals an overall sequence homology of approximately 72 percent, going up to 88 percent within the core sequence motif.

EXAMPLE 11

Generation of Elf-1-AP Fusion Proteins

In order to enhance expression of Elf-1 polypeptides in certain eukaryotic cells, the vector APtag-2 was generated by subcloning the alkaline phosphatase coding sequence and flanking polylinker sequence from APtag-1 (Flanagan and Leder, supra) into a pcDNAI vector (Invitrogen, San Diego). Utilizing Elf-1 cDNA, portions of the Elf-1 coding sequence were inserted into the vector APtag-2 to generate Elf-1-AP fusion proteins. In one experiment, the portion of the chElf-1 cDNA encoding amino acid residues Met-1 through Ser-177 were subcloned into APtag-1 in frame with the alkaline phosphatase gene product. Expression of the construct in NIH 3T3 cells resulted in conditioned media containing an active alkaline phosphatase fusion protein which was observed to retain the receptor binding capabilities of the natural Elf-1 protein.

EXAMPLE 12

Chromosomal Mapping of the Human Elf-1 Gene

Genomic clones of a human Elf-1 gene were isolated by stringency screening (65° C. with 0.2 ×SSP wash) of a human genomic library (ClonTech, catalog number HL1067) with cDNA probes based on the complete coding sequence for muElf-1. Isolated EMLB3 phage clones were confirmed by high stringency Southern hybridization. Purified whole phage DNA was labelled for fluorescent in situ hybridization (FISH) analysis.

FISH analysis was performed using established methods (Demetrick et al. (1994) Cytogenet Cell Genet 66:72–74; Demetrick et al. (1993) Genomicsl8:144–147; Price (1993) Blood Rev 7:127–134; Trask (1991) Trends Genet 7:149–154; and DeMarini et al. (1991) Environ Mol Mutagen 18:222–223) on metaphase spreads from human cells. Suppression with a mixture of sonicated human DNA and cot1 DNA was used to reduce the background. The stained slides were counterstained with propidium iodide (for an R banding pattern) or DAPI and actinomycin D (for a DA-DAPI banding pattern), mounted in antifade medium and visualized by microscopy. The human Elf-1 gene was visualized to map to the region of 1q21.

It is noteworthy that certain pathogenetic abnormalities in humans have been shown to be associated with lesions in the same region of chromosome 1. For example, multiplication or deletion of a region including 1q21, have been observed cytogenetically to be associated with a number of tumors of neural origin, such as cerebral tumors occuring in Kinefelter patients (Casalone et al. (1994) Cancer Genet Cytogenet 74:25–29), chordomas (Mertens et al. (1994) Cancer Genet Cytogenet 74:147–151), primary CNS lymphomas (Itoyama et al. (1994) Cancer 73:455–463), and peripheral neuroectodermal tumors (Douglass et al. (1990) Cytogenet Cell Genet 53:87–90). Moreover, multiple craniofacial anomalies have been associated with an interstitial deletions of chromosome 1, e.g. deletion of q21→q25 (Leichtrnan et al. (1993) Am J Med Genet 45:677–678). Moreover, genes from three other protein families, which are expressed during differentiation of certain tissues, have been mapped to chromosome 1q21 (Volz et al. (1993) Genomics 18:92–99), raising the possibility of genetic linkage with the Elf-1 gene, such as at the level of gross transcriptional regulation.

EXAMPLE 13

Chromosomal Mapping of the Mouse Elf-1 Gene

The mouse Elf-1 gene was mapped utilizing interspecific mouse backcross panels to position the loci (see, for example, Copeland et al. (1991) Trends Genet 7:113–118). The linkage map revealed the mouse Elf-1 gene to be located on chromosome 10, between Col6a-1 and Igf-1. In particular, the muElf-1 gene lies about 2–3 cM distal to Col6a-1, and about 6–7 cM proximal to Igf-1.

Interestingly, mouse mutations that have been mapped to the same general region of chromosome 10 include jittery (ji), mocha (mh), grizzled (gr), Ame's walzter (av), and hesitant (hes), each of which have symptoms which could potentially implicate the muElf-1 gene in generation of the phenotype. For instance, homozygotes for jittery show muscular incoordination, as well as polycystic alterations in the white matter of the brain. The Ame's waltzer mice have typical behavior of the circling mutants, including head-tossing, deafness and hyperactivity. These mice demonstrate development defects in the organ of Corti, with subsequent degeneration of hair cells and spiral ganglion cells.

Experimental Procedures

A. Construction and Expression of AP Fusion Proteins

To produce the mek4-AP and sek-AP fusion constructs, sequences encoding the extracellular domains were amplified by polymerase chain reaction. For mek4-AP the sequence from nucleotide 32 to 1708 (Sajjadi et al., (1991) New Biol 3:769–778; Genbank accession M68513) was amplified from mouse brain cDNA, and for sek-AP the sequence from nucleotide 12 to 1698 (Gilardi-Hebenstreit et al., (1992) Oncogene 7:2499–2506; Genbank accession X65138) was amplified from cDNA of NIH-3T3 cells. Restriction sites at the ends of the amplification primers were cleaved with BamHI and inserted into the BglII site of the vector APtag-1 (Flanagan and Leder, supra) so that each receptor extracellular domain was fused to secreted human placental alkaline phosphatase through a four amino acid linker (Gly-Ser-Ser-Gly).

Similarly, Elf-1-AP fusion proteins were generated by amplifying portions of the muElf-1 sequence using primers which provided BamHI or BgIII restriction sites for subcloning into the APtag-1 vector as above.

Each plasmid was linearized with PvuI, and 2 µg (more can give lower expression) was stably transfected with 0.5 µg of pSV7neo selection plasmid and 20 µg of calf thymus carrier DNA by calcium phosphate precipitation into a 10 cm dish of NIH-3T3 cells. Cells were cloned in 96-well plates during G418 selection and high-expressers were selected by testing supernatants for AP activity in a 96-well plate reader as described (Flanagan and Leder, supra) except that L-homoarginine was omitted from all AP assays here. Clones expressing approx. 1,000 OD/hr of AP activity per ml of supernatant were used as a source of mek4-AP and sek-AP proteins. Cells were grown to confluence, then media conditioned for a further 3 days were centrifuged, 0.45 µm filtered and stored at 4° C. with 20 mM HEPES pH 7.0 and 0.05% sodium azide. AP activities are expressed here as OD units per hour (OD/hr), indicating the rate of hydrolysis of the chromogenic substrate p-nitrophenyl phosphate. One picomole of AP fusion protein corresponds to an activity of approximately 30 OD/hr under the conditions of the assay.

B. RAP In Situ of Mouse Embryos

Embryos from Swiss-Webster mice were transferred to 1.5 ml microfage tubes and rinsed once in HBHA buffer (Hank's balanced salt solution with 0.5 mg/ml BSA, 0.1% $NaN_3$, 20 mM HEPES pH 7.0). The embryos were then incubated in tissue culture supernatants containing RAP fusion proteins, or AP as a control, for 75 min on a rotator at room temperature. They were then washed six times in HBHA buffer, treated for 2.5 min with an acetone/formaldehyde fixative (60% acetone, 3% formaldehyde, 20 mM HEPES pH 7.0), washed three times in HBS (150 mM NaCl, 20 mM HEPES pH 7.0), and then incubated in a 65° C. water bath for 15 min, inactivating endogenous cellular phosphatases but not the uniquely heat stable AP of the fusion proteins. After rinsing with AP buffer (100 mM Tris-HCl pH 9.5, 100 mM NaCl, 5 mM $MgCl_2$), the cells were stained for 5–10 min in the same buffer containing 0.17 mg/ml BCIP and 0.33 mg/ml NBT.

C. Expression Library Construction and Screening

Eighty embryos at day 9.5 of development were obtained from six Swiss-Webster mice. Embryos were rinsed in PBS and the region of the midbrain and anterior hindbrain previously found to stain strongly with mek4-AP and sek-AP by RAP in situ was cut from each embryo under a dissecting microscope. RNA was prepared by the single-step method (Chomczynski et al. (1987) *Anal. Biochem* 162:156–159) and after one round of oligo(dT) cellulose purification the yield was 4 µg. Double stranded cDNA was prepared (Invitrogen kit), inserted into the expression vector CDM8 (Seed et al. (1987) *PNAS* 84:3365–3369) and transfected into *E. coli*. Pools of approximately 1,000 clones were plated on nitrocellulose filters and then replica plated. DNA was prepared from one replica and the other was stored.

To screen the library, DNA of each pool was transiently transfected into a 10 cm dish of COS cells using Lipofectamine as described by the manufacturer (Gibco-BRL). After 48 hr the cells, just at or before reaching confluence, were washed once in HBHA buffer and then incubated in an equal mixture of sek-AP and sek-AP supernatants for 90 min at room temperature. Plates were then washed six times in HBHA buffer, treated for 30 sec with acetone/formaldehyde fixative, and washed twice in HBS. Uniform heating to inactivate endogenous cellular phosphatases is critical and was achieved by incubating plates containing 10 ml HBS in a single layer on a flat shelf in a 65° C. oven for 100 min. Plates were then rinsed with AP buffer and stained for AP activity for 0.5–12 hr in the same buffer containing 0.17 mg/ml BCIP and 0.33 mg/ml NBT. Staining was monitored periodically against a white background under a dissecting microscope.

After identification of a positive pool, the stored library filter was replica plated again, and rescreening was performed with colonies from successively smaller areas of the filter. After a total of three rounds of screening, DNA was prepared from single colonies and a positive clone was identified.

D. Quantitative Cell Surface Binding Assays, Cell Culture, and PI-PLC Treatment

Quantitative cell surface binding assays with mek4-AP and sek-AP were performed essentially as described previously for Kit-AP (Flanagan and Leder, supra; Flanagan et al., supra). Cells in 10 cm plates were washed with HBHA buffer and then incubated at room temperature with supernatants containing mek4-AP or sek-AP fusion proteins or AP as a control. For Scatchard binding analyses the supernatants were concentrated in an ultrafiltration cell (Amicon) and dilutions were made with HBHA buffer. After 90 min, the cells were washed six times with HBHA buffer, lysed, and assayed calorimetrically for bound alkaline phosphatase activity.

Cells were grown in DMEM with 10% bovine calf serum. Cell lines are available from the American Type Culture Collection, except the NC7 lines, established by oncogene-mediated immortalization of explanted mouse neural crest and BMS-12, a stromal line established by passaging of mouse bone marrow.

For experiments to assess phosphatidylinositol linkage, cells or embryos were pre-treated in complete tissue culture medium at 37° C. for 2 hr with 100–300 mU/ml of PI-PLC (Sigma).

E. Co-immunoprecipitation with Receptor-AP Fusion Proteins

Ligand polypeptides were analyzed by co-immunoprecipitation with mek4-AP. Cells in 6-well plates were metabolically labeled with $^{35}$S-methionine as described (Flanagan et al., supra). The supernatants, concentrated to 200 µl on a Centricon-10 (Amicon), and cells, lysed in 200 µl of lysis buffer (1% Triton-X100, 10 mM Tris-HCl pH 7, 1 mM PMSF) were then incubated for 90 min at room temperature with an equal volume of supernatant containing mek4-AP or AP. Labeled ligand polypeptides were then co-immunoprecipitated with the mek4-AP fusion protein using a monoclonal antibody against human placental alkaline phosphatase (Cat. no. MIA 1801, Medix Biotech, Foster City, Calif.) as described (Flanagan et al., supra).

F. In Situ RNA Hybridization of Mouse Embryos

Whole mount in situ hybridization of mouse embryos was performed as described (*In situ hybridization: a practical approach*, D. G. Wilkinson, ed. (Oxford University Press), pp. 75–83) except that post-hybridization washes were done three times in solution 1 and three times in solution 3, without using solution 2 or ribonuclease. RNA probes were prepared by transcription from promoters in the Bluescript (Stratagene) or CDM8 (Seed et al., supra) plasmids. The Elf-1 antisense probe was a 1 kb fragment extending from a unique PstI site to the 3' end of Elf-1. The sek antisense probe was a 0.8 kb fragment from a BsmI site at nucleotide 878 to the transmembrane sequence at nucleotide 1698, and the sense probe was a 0.8 kb fragment from a HindIII site at nucleotide 879 to nucleotide 12 at the 5' end (Gilardi-Hebenstreit et al. (1992) *Oncogene* 7:2499–2506; Genbank accession X65138). The mek4 antisense probe was a 1.1 kb fragment from a BsmI site at nucleotide 564 to the transmembrane sequence at nucleotide 1708, and the sense probe was a 0.8 kb fragment from a HindIII site at nucleotide 897 to nucleotide 32 at the 5' end (Sajjadi et al., (1991) *New Biol* 3:769–778; Genbank accession M68513).

G. Cloning of Chicken Elf-1 Protein, and Chicken EPH Receptors

Chick Elf-1 clones were isolated from a library of day 3 chick embryo cDNA, in the Uni-ZAP XR (Stratagene) phage lambda vector, by hybridizing with a mouse cDNA probe and washing at low stringency (2×SSC, 50° C.). The probe was the 1.5 kb HindIII to XhoI insert of clone Elf-1, a subclone of plasmid E3–3, containing approximately 1.5 kb of the mouse Elf-1 cDNA sequence. The phagemid inserts of the lambda clones were excised and two clones, cEI-1 and cEI-6, were characterized further. Clone cEI-6 has a 2.0 kb insert and encodes a complete amino acid sequence for chick Elf-1, as represented by SEQ ID Nos: 3 and 4. Clone cEl-1 is truncated at the 5' end and has a 1.5 kb insert.

Three separate antisense RNA probes were used for in situ hybridization of Elf-1 RNA. All gave similar results. One was prepared by subcloning into the Bluescript II KS+vector (Stratagene) a 1.0 kb fragment of clone cEl-1 extending from a KpnI site in the 5' polylinker to a unique AccI site in the 3' untranslated sequence. This clone, cEl-1KA, was cut with KpnI and transcribed with T7 RNA polymerase to give a 1.0 kb antisense probe, or cut with SacI and transcribed with T3 RNA polymerase to give a 1.0 kb sense control probe. A second probe was prepared by subcloning a 1.35 kb fragment of clone cEl-6, extending from a KpnI site in the 5' polylinker to the unique AccI site in the 3' untranslated sequence, giving subclone El-6KA. This subclone was cut with StyI and transcribed with T7 polymerase to give a 0.35 kb antisense probe. The third probe was produced by cutting clone cEl-1 with AccI and transcribing with T3 polymerase to give a 0.6 kb antisense probe.

Chick Mek4 and Sek probes were produced by polymerase chain reaction amplification of cDNA sequences from RNA of day 3 chick embryos. In both cases the probes were derived from cDNA subclones encoding part of the extracellular domain of the receptor. Clone cMek4HE, in the Bluescript II KS+vector, extends from a HindIII site at nucleotide 865 to an artificial EcoRI site introduced at nucleotide 1651 of the Mek4/Cek4 cDNA sequence (Sajjadi et al. *New Biol.* 3:769–778 (1991); Genbank accession M68514)). Clone cMek4HE was cut with HindIII and transcribed with T7 RNA polymerase to produce an antisense Mek4 probe. Clone cSekHK, also in Bluescript II KS+, extends from a HindIII site at nucleotide 412 to a KpnI site at nucleotide 1222 of the Sek/Cek8 cDNA sequence (Sajjadi et al. (1991) *New Biol* 3:769–778; Genbank accession Z19059). Clone cSekHK was cut with HindIII and transcribed with T3 RNA polymerase to produce an antisense Sek probe.

H. Analysis of Embryos

Whole mount analyses of Elf-1 expression, by RNA hybridization in situ or RAP in situ, were performed at days 2 to 6 of development on complete embryos, or at days 6 to 11 on the embryonic brain dissected out and freed of the pia mater. Retinal sections were analyzed for Mek4 and Sek expression by dissecting out the eye, removing the lens and vitreous, and preparing 24 μm frozen sections for hybridization. For retinal whole mount analysis, the eye was dissected out, the pigment epithelium removed, the optic cup was fixed and hybridized, and after staining, the retinas were spread out for observation.

RNA hybridization in situ was performed using digoxigenin-labeled probes, and developing with an alkaline phosphatase-conjugated antibody, as described (Wilkinson et al. (1993) *Meth. Enzymol.* 225:361–373) except that post-hybridization washes were three times each in solutions 1 and 3, without solution 2 or RNase. For densitometric analysis of retinal whole mounts, the stained retinas, photographed on Kodak Ektachrome 160T film, were digitized with a Nikon Coolscan transparency scanner, and then profile plots were calculated using the NIH Image program.

RAP in situ analysis was performed essentially as described above, using mouse Mek4-AP and Sek-AP fusion proteins. All tissues were treated with receptor-AP fusion proteins unfixed, except day 6 brain. Because of the fragility of this tissue, day 6 embryos were fixed with 4% paraformaldehyde at room temperature for 90 min, then the brain was dissected out. Embryos were transferred to 1.5 ml microfuge tubes, or embryonic brains to 24 well plates, then were rinsed once in HBHA buffer (Hank's balanced salt solution with 0.5 mg/ml BSA, 0.1% NaN3, 20 mM HEPES pH 7.0), and incubated in tissue culture supernatants containing receptor-AP fusion proteins, or AP as a control, for 75 min on a rotator or orbital shaker at room temperature. They were then washed six times in HBHA buffer, treated for 2.5 min with an acetone/formaldehyde fixative (60% acetone, 3% formaldehyde, 20 mM HEPES pH 7.0), washed three times in HBS (150 mM NaCl, 20 mM HEPES pH 7.0), and then incubated in a 65° C. water bath for 15 min, inactivating endogenous cellular phosphatases but not the characteristically heat stable AP of the fusion proteins. After rinsing with AP buffer (100 mM Tris-HCl pH 9.5, 100 MM NaCl, 5 mM $MgCl_2$), the embryos were stained for 5–10 min in the same buffer containing 0.17 mg/ml BCIP and 0.33 mg/ml NBT.

To assess GPI linkage, before RAP in situ the tissues were pretreated for 1 hr at 37° C. in complete tissue culture medium with or without 100 U/ml of PI-PLC (Sigma).

All of the above-cited references and publications are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

---

We claim:

1. A recombinant polypeptide comprising a polypeptide sequence selected from the group consisting of an amino acid sequence at least 90 percent identical to SEQ ID No. 2, an amino acid sequence at least 90 percent identical to SEQ ID No. 4, a portion of an amino acid sequence at least 90 percent identical to SEQ ID No. 2, and a portion of an amino acid sequence at least 90 percent identical to SEQ ID No. 4, and which polypeptide or polypeptide portion binds to a mek-4 or sek receptor.

2. The recombinant polypeptide of claim 1, which binds to a mek-4 receptor.

3. The recombinant polypeptide of claim 1, which polypeptide sequence comprises a $Cys_4$ motif at least 90 percent identical to a $Cys_4$ motif having amino acids 69 through 159 of SEQ ID No. 2 or amino acids 61 through 150 of SEQ ID NO. 4.

4. The recombinant polypeptide of claim 1, which polypeptide sequence comprises a core sequence motif at least 90 percent identical to a core sequence motif having amino acids 35 through 166 of SEQ ID No. 2 or amino acids 33 through 157 of SEQ ID No. 4.

5. The recombinant polypeptide of claim 1, which polypeptide comprises a mature polypeptide sequence at least 90 percent identical with a mature polypeptide having the sequence of SEQ ID Nos. 2 or 4.

6. The recombinant polypeptide of claim 1, which polypeptide is post-translationally modified to include a phosphatidylinositol moiety, a carbohydrate, or both.

7. The recombinant polypeptide of claim 1, which protein is a fusion protein.

8. The recombinant polypeptide of claim 7, wherein said fusion protein further includes, in addition to said polypeptide sequence, a second polypeptide sequence which functions as a detectable label for detecting the presence of said fusion protein, or as a matrix-binding domain for immobilizing said fusion protein.

9. The recombinant polypeptide of claim 8, wherein said second polypeptide sequence has an enzymatic activity.

10. An isolated or recombinant polypeptide comprising a polypeptide sequence identical with an amino acid sequence set forth in the general formula designated by SEQ ID No. 5 and which polypeptide binds to a mek-4 or sek receptor.

11. The recombinant polypeptide of claim 1, which binds to a sek receptor.

12. The recombinant polypeptide of claim 1 consisting of SEQ ID NO. 2.

13. The recombinant polypeptide of claim 1 comprising SEQ ID NO. 4.

14. The recombinant polypeptide of claim 1 consisting of SEQ ID NO. 4.

* * * * *

UNITED STATES PATENT AND TRADEMARK OFFICE
CERTIFICATE OF CORRECTION

PATENT NO.    : 6,777,536 B1
DATED         : August 17, 2004
INVENTOR(S)   : Flanagan et al.

It is certified that error appears in the above-identified patent and that said Letters Patent is hereby corrected as shown below:

Title page,
Item [63], Related U.S. Application Data, please replace:

"[63] Continuation-in-part of application no. 08/308,814, filed on Sept. 19, 1994, now abandoned." with
-- [63] Continuation-in-part of application no. 08/308,814, filed on Sept. 19, 1994, issued as U.S. Pat. 6,268,476. --

Signed and Sealed this

Sixteenth Day of November, 2004

JON W. DUDAS
*Director of the United States Patent and Trademark Office*

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 1809 base pairs
      (B) TYPE: nucleic acid
      (C) STRANDEDNESS: both
      (D) TOPOLOGY: linear -continued

```
        (ii) MOLECULE TYPE: cDNA (ix) FEATURE:
              (A) NAME/KEY: CDS
              (B) LOCATION: 265..891

(ix) FEATURE:
              (A) NAME/KEY: 5'UTR
              (B) LOCATION: 1..264

(ix) FEATURE:
              (A) NAME/KEY: 3'UTR
              (B) LOCATION: 892..1809

(ix) FEATURE:
              (A) NAME/KEY: sig_peptide
              (B) LOCATION: 255..324

(xi) SEQUENCE DESCRIPTION: SEQ ID NO:1:

GGGAGCCCCC GCGCCCGGGG AACCGCGAGA GCGCCTTGCA GTGCACCGCT CGGGCCTCTG      60

CCCGCGCCGC CGTCGCCGCC GCCGCCGCCG CCGCCGCCGC CGCCTGGTTT CTCGGCGCCC     120

GCGGTCTACG GCGGGGCGC  AGAGGCGGGG CGGAGATCTC CAAGCGCGCG CGCGTCCGCC     180

CGCTCGGCGC GAGGCGGAGG CGGAGACGCG GGGCCAGGCG GCGGCTGGAG AGCGAGGGAG     240

CGAGCGCGCG GCAGCACCGG GGCC ATG GCG CCC GCG CAG CGC CCG CTG CTG       291
                          Met Ala Pro Ala Gln Arg Pro Leu Leu
                            1               5

CCG CTG CTG CTG CTG CTG CCG CTG CGT GCG CGC AAC GAG GAC CCG           339
Pro Leu Leu Leu Leu Leu Pro Leu Arg Ala Arg Asn Glu Asp Pro
 10              15                  20                  25

GCC CGG GCC AAC GCT GAC CGA TAC GCA GTC TAC TGG AAC CGT AGC AAC       387
Ala Arg Ala Asn Ala Asp Arg Tyr Ala Val Tyr Trp Asn Arg Ser Asn
                30                  35                  40

CCC AGG TTT CAG GTG AGC GCT GTG GGT GAT GGC GGC GGC TAT ACC GTG       435
Pro Arg Phe Gln Val Ser Ala Val Gly Asp Gly Gly Gly Tyr Thr Val
            45                  50                  55

GAG GTG AGC ATC AAC GAC TAC CTG GAT ATC TAC TGC CCA CAC TAC GGG       483
Glu Val Ser Ile Asn Asp Tyr Leu Asp Ile Tyr Cys Pro His Tyr Gly
        60                  65                  70

GCG CCG CTG CCC CCG GCT GAG CGC ATG GAG CGG TAC ATC CTG TAC ATG       531
Ala Pro Leu Pro Pro Ala Glu Arg Met Glu Arg Tyr Ile Leu Tyr Met
    75                  80                  85

GTG AAT GGT GAG GGC CAC GCC TCC TGT GAC CAC CGG CAG CGA GGC TTC       579
Val Asn Gly Glu Gly His Ala Ser Cys Asp His Arg Gln Arg Gly Phe
 90                  95                 100                 105

AAG CGC TGG GAA TGC AAC CGG CCC GCA GCG CCC GGG GGA CCC CTC AAG       627
Lys Arg Trp Glu Cys Asn Arg Pro Ala Ala Pro Gly Gly Pro Leu Lys
                110                 115                 120

TTC TCA GAG AAG TTC CAA CTC TTC ACC CCC TTT TCC CTG GGC TTT GAG       675
Phe Ser Glu Lys Phe Gln Leu Phe Thr Pro Phe Ser Leu Gly Phe Glu
            125                 130                 135

TTC CGG CCT GGC CAC GAA TAC TAC TAC ATC TCT GCC ACA CCT CCC AAC       723
Phe Arg Pro Gly His Glu Tyr Tyr Tyr Ile Ser Ala Thr Pro Pro Asn
        140                 145                 150

CTC GTG GAC CGA CCC TGC CTG CGA CTC AAG GTT TAT GTG CGT CCA ACC       771
Leu Val Asp Arg Pro Cys Leu Arg Leu Lys Val Tyr Val Arg Pro Thr
    155                 160                 165

AAT GAG ACC CTG TAT GAG GCT CCA GAG CCC ATC TTC ACC AGT AAC AGC       819
Asn Glu Thr Leu Tyr Glu Ala Pro Glu Pro Ile Phe Thr Ser Asn Ser
170                 175                 180                 185

TCC TGC AGC GGC CTG GGT GGC TGC CAC CTC TTC CTC ACC ACC GTC CCT       867
Ser Cys Ser Gly Leu Gly Gly Cys His Leu Phe Leu Thr Thr Val Pro
```

```
                   190           195           200
GTG CTG TGG TCC CTT CTG GGC TCC TAGTGTCAGG CCGGAGAACA CCAGCCCCAC    921
Val Leu Trp Ser Leu Leu Gly Ser
                   205

CTGGACCCCG TGACCTTTGC CCTCTGACCT GCCACGGCCA CCTCCGAGAC AAAATCCTTG    981

CTGCTTCTCT TTCATGGTGC CGTCCCGCCG GAGGAGGCCA TCCATCCGTC CCTGGGATGC   1041

AACATGGGGT CCCAATGCCT GAGGAGAAGA CCCCCCCCCA AGGCTGACTC GCTTTCACCA   1101

GGCCACCAGG GCCATCCAGT GTTGTTTAAT TACAGTCGGA AAGACTTAAG GTTTTTCTTT   1161

TAATTTAATT TATTCCCTGA CATTGCTGGT GACACTGGGA AGGGAACAAG CCACAGGGAT   1221

GAGGTGAAGC CATCTCTGTC CTTCCTGGAA TACCGGAGAT CCAGGGGCCT CCAGCTGCTC   1281

CTTTCTTCTG TGTCCTGTTA TTTGGGTCCC AGATGGAGCC CACCGCGGAC TTGCCTTGCA   1341

TTCCTCAGGC CAGGCAAGCC TGAGCCAGAA AGGGGGCACG GTGCCAGCCT CTCGGGGACT   1401

CTGGGGGTGC CATCCCCCAC TCTTCTTCCA GCCACTCTCG GGCCCACTC CCACATCATC    1461

TCAGAAACCC TTCAGCCCTC GCAACTCGCC CCTCCGGGCC CCCCCACCAG GCACAACCAT   1521

CCCCGGGGCC AGCCGGGACG TTGTCGGTTT ATTTCTGTAA ATAGAAACCA GCAAGTGTAT   1581

ACTGTGATTT ATTTTAATGT ATTCTTAAGG ACAGAATGGA AATTCTTTAA AAAAAATTTT   1641

TTTTCCGACC TTCAATTCAA GGGGTCATTT ATTTTGGTGG GGGGAGTGGG GTGGACTTTT   1701

TAGGATAGAA GCAACACTTT GCAATAAACT CATTTTTTTT TGTTCCGTTG GAGCCCTCCC   1761

CCTTGATCAT GTGACCTAGT AATGTTTATA ACAAAAAAAA AAAAAAA                1809

(2) INFORMATION FOR SEQ ID NO:2:

(i) SEQUENCE CHARACTERISTICS:
        (A) LENGTH: 209 amino acids
        (B) TYPE: amino acid
        (D) TOPOLOGY: linear (ii) MOLECULE TYPE: protein (xi) SEQUENCE DESCRIPTION: SEQ ID NO:2:

Met Ala Pro Ala Gln Arg Pro Leu Leu Pro Leu Leu Leu Leu Leu
 1               5                  10                  15

Pro Leu Arg Ala Arg Asn Glu Asp Pro Ala Arg Ala Asn Ala Asp Arg
                20                  25                  30

Tyr Ala Val Tyr Trp Asn Arg Ser Asn Pro Arg Phe Gln Val Ser Ala
            35                  40                  45

Val Gly Asp Gly Gly Tyr Thr Val Glu Val Ser Ile Asn Asp Tyr
        50                  55                  60

Leu Asp Ile Tyr Cys Pro His Tyr Gly Ala Pro Leu Pro Pro Ala Glu
65                  70                  75                  80

Arg Met Glu Arg Tyr Ile Leu Tyr Met Val Asn Gly Glu Gly His Ala
                85                  90                  95

Ser Cys Asp His Arg Gln Arg Gly Phe Lys Arg Trp Glu Cys Asn Arg
            100                 105                 110

Pro Ala Ala Pro Gly Gly Pro Leu Lys Phe Ser Glu Lys Phe Gln Leu
        115                 120                 125

Phe Thr Pro Phe Ser Leu Gly Phe Glu Phe Arg Pro Gly His Glu Tyr
    130                 135                 140

Tyr Tyr Ile Ser Ala Thr Pro Pro Asn Leu Val Asp Arg Pro Cys Leu
145                 150                 155                 160

Arg Leu Lys Val Tyr Val Arg Pro Thr Asn Glu Thr Leu Tyr Glu Ala
```

-continued

```
                165                  170                  175
Pro Glu Pro Ile Phe Thr Ser Asn Ser Ser Cys Ser Gly Leu Gly Gly
            180                  185                  190

Cys His Leu Phe Leu Thr Thr Val Pro Val Leu Trp Ser Leu Leu Gly
        195                  200                  205

Ser
```

(2) INFORMATION FOR SEQ ID NO:3:

(i) SEQUENCE CHARACTERISTICS:
        (A) LENGTH: 783 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 86..685

(ix) FEATURE:
        (A) NAME/KEY: 5'UTR
        (B) LOCATION: 1..85

(ix) FEATURE:
        (A) NAME/KEY: 3'UTR
        (B) LOCATION: 686..783

(ix) FEATURE:
        (A) NAME/KEY: sig_peptide
        (B) LOCATION: 86..148

(xi) SEQUENCE DESCRIPTION: SEQ ID NO:3:

```
GACGGTATCG ATAAGCTTGA TATCGAATTC GAGGACCGGG TACCATGACG CCGCCGCCCG      60

CTGAGCCGCT CCGCTCCGCC GGACG ATG CCG CGC TGG GAG GCG GCC GCG CTG      112
              Met Pro Arg Trp Glu Ala Ala Ala Leu
                1                  5

CTC GCC GCG ATC GTC GGC GTC TGC GTG TGG AGC GAC GAC CCC GGC AAA      160
Leu Ala Ala Ile Val Gly Val Cys Val Trp Ser Asp Asp Pro Gly Lys
 10              15                  20                  25

GTG ATC TCG GAC CGC TAC GCC GTC TAT TGG AAC CGC AGC AAC CCC AGG      208
Val Ile Ser Asp Arg Tyr Ala Val Tyr Trp Asn Arg Ser Asn Pro Arg
             30                  35                  40

TTC CAC CGC GGG GAT TAC ACC GTG GAG GTG AGC ATC AAT GAC TAC CTG      256
Phe His Arg Gly Asp Tyr Thr Val Glu Val Ser Ile Asn Asp Tyr Leu
                 45                  50                  55

GAC ATC TAC TGC CCT CAC TAC GAG GAG CCG CTG CCC GCC GAG CGC ATG      304
Asp Ile Tyr Cys Pro His Tyr Glu Glu Pro Leu Pro Ala Glu Arg Met
             60                  65                  70

GAG CGC TAC GTC CTC TAC ATG GTC AAC TAC GAG GGC CAC GCG TCC TGC      352
Glu Arg Tyr Val Leu Tyr Met Val Asn Tyr Glu Gly His Ala Ser Cys
 75                  80                  85

GAC CAC CGG CAG AAG GGC TTC AAA CGT TGG GAG TGC AAC CGG CCC GAC      400
Asp His Arg Gln Lys Gly Phe Lys Arg Trp Glu Cys Asn Arg Pro Asp
 90                  95                 100                 105

TCC CCC AGC GGA CCC CTC AAG TTC TCA GAG AAG TTC CAG CTC TTC ACC      448
Ser Pro Ser Gly Pro Leu Lys Phe Ser Glu Lys Phe Gln Leu Phe Thr
                110                 115                 120

CCC TTC TCT TTG GGC TTC GAG TTC CGT CCC GGC CAC GAG TAT TAC TAC      496
Pro Phe Ser Leu Gly Phe Glu Phe Arg Pro Gly His Glu Tyr Tyr Tyr
             125                 130                 135

ATC TCT GCG TCT CCC CCG AAC GTG GTG GAC AGA CCC TGC CTC AAG CTG      544
Ile Ser Ala Ser Pro Pro Asn Val Val Asp Arg Pro Cys Leu Lys Leu
```

```
          140             145            150
AAG GTT TAC GTT CGG CCG ACG AAC GAT TCC CTC TAT GAG TCC CCA GAG     592
Lys Val Tyr Val Arg Pro Thr Asn Asp Ser Leu Tyr Glu Ser Pro Glu
        155                 160                165

CCC ATC TTC ACC AGC AAC AAC TCG TGC TGC AGC CTT GCA GTG CCG CGT     640
Pro Ile Phe Thr Ser Asn Asn Ser Cys Cys Ser Leu Ala Val Pro Arg
170             175                 180                 185

GCC GTG CTG GTG GCC GCG CCG GTC TTC TGG ACT CTG CTG GGC TCT         685
Ala Val Leu Val Ala Ala Pro Val Phe Trp Thr Leu Leu Gly Ser
                190                 195                 200

TAGTGCCGCG GGACGGACGG ACGGGACGGG TGACGGGTGA CGGCTTCAGC ACCACCACGG   745

GACAGAGCTG GGGCTGCACC ACTGCCAGGA GCCCCACT                           783

(2) INFORMATION FOR SEQ ID NO:4:

(i) SEQUENCE CHARACTERISTICS:
        (A) LENGTH: 200 amino acids
        (B) TYPE: amino acid
        (D) TOPOLOGY: linear (ii) MOLECULE TYPE: protein (xi) SEQUENCE DESCRIPTION: SEQ ID NO:4:

Met Pro Arg Trp Glu Ala Ala Ala Leu Leu Ala Ala Ile Val Gly Val
 1               5                  10                  15

Cys Val Trp Ser Asp Asp Pro Gly Lys Val Ile Ser Asp Arg Tyr Ala
            20                  25                  30

Val Tyr Trp Asn Arg Ser Asn Pro Arg Phe His Arg Gly Asp Tyr Thr
        35                  40                  45

Val Glu Val Ser Ile Asn Asp Tyr Leu Asp Ile Tyr Cys Pro His Tyr
    50                  55                  60

Glu Glu Pro Leu Pro Ala Glu Arg Met Glu Arg Tyr Val Leu Tyr Met
65                  70                  75                  80

Val Asn Tyr Glu Gly His Ala Ser Cys Asp His Arg Gln Lys Gly Phe
                85                  90                  95

Lys Arg Trp Glu Cys Asn Arg Pro Asp Ser Pro Ser Gly Pro Leu Lys
            100                 105                 110

Phe Ser Glu Lys Phe Gln Leu Phe Thr Pro Phe Ser Leu Gly Phe Glu
        115                 120                 125

Phe Arg Pro Gly His Glu Tyr Tyr Tyr Ile Ser Ala Ser Pro Pro Asn
130                 135                 140

Val Val Asp Arg Pro Cys Leu Lys Leu Lys Val Tyr Val Arg Pro Thr
145                 150                 155                 160

Asn Asp Ser Leu Tyr Glu Ser Pro Glu Pro Ile Phe Thr Ser Asn Asn
                165                 170                 175

Ser Cys Cys Ser Leu Ala Val Pro Arg Ala Val Leu Val Ala Ala Pro
            180                 185                 190

Val Phe Trp Thr Leu Leu Gly Ser
        195                 200

(2) INFORMATION FOR SEQ ID NO:5:

(i) SEQUENCE CHARACTERISTICS:
        (A) LENGTH: 179 amino acids
        (B) TYPE: amino acid
        (D) TOPOLOGY: linear (ii) MOLECULE TYPE: peptide
```

```
    (v) FRAGMENT TYPE: internal (xi) SEQUENCE DESCRIPTION: SEQ ID NO:5:

Asp Arg Tyr Xaa Val Tyr Trp Asn Arg Ser Asn Pro Arg Phe Xaa Xaa
1               5                   10                  15

Xaa Xaa Xaa Gly Asp Xaa Xaa Xaa Tyr Thr Val Glu Val Ser Ile Asn
            20              25                  30

Asp Tyr Leu Asp Ile Tyr Cys Pro His Tyr Xaa Xaa Pro Leu Pro Xaa
        35              40              45

Ala Glu Arg Met Glu Arg Tyr Xaa Leu Tyr Met Val Asn Xaa Glu Gly
    50              55              60

His Ala Ser Cys Asp His Arg Gln Xaa Gly Phe Lys Arg Trp Glu Cys
65              70              75                      80

Asn Arg Pro Xaa Xaa Pro Xaa Gly Pro Leu Lys Phe Ser Glu Lys Phe
            85          90                      95

Gln Leu Phe Thr Pro Phe Ser Leu Gly Phe Glu Phe Arg Pro Gly His
            100             105                 110

Glu Tyr Tyr Tyr Ile Ser Ala Xaa Pro Pro Asn Xaa Val Asp Arg Pro
        115             120             125

Cys Leu Xaa Leu Lys Val Tyr Val Arg Pro Thr Asn Xaa Xaa Leu Tyr
    130             135             140

Glu Xaa Pro Glu Pro Ile Phe Thr Ser Asn Xaa Ser Cys Xaa Xaa Leu
145             150             155             160

Xaa Xaa Xaa Xaa Xaa Xaa Leu Xaa Xaa Xaa Pro Val Xaa Trp Xaa Leu
            165             170             175

Leu Gly Ser
```